US006722395B2

(12) United States Patent  
Overbeck et al.

(10) Patent No.: US 6,722,395 B2
(45) Date of Patent: Apr. 20, 2004

(54) DEPOSITING FLUID SPECIMENS ON SUBSTRATES, RESULTING ORDERED ARRAYS, TECHNIQUES FOR ANALYSIS OF DEPOSITED ARRAYS

(76) Inventors: James W. Overbeck, 112 Martins La., Hingham, MA (US) 02043; Peter T. Flowers, 1275 Brook Rd., Milton, MA (US) 02186; Jean I. Montagu, 76 Walnut Pl., Brookline, MA (US) 02146; Myles L. Mace, 124 Farm St., Dover, MA (US) 02003; Peter Honkanen, 1 School St., Arlington, MA (US) 02174

( * ) Notice: Subject to any disclaimer, the term of this patent is extended or adjusted under 35 U.S.C. 154(b) by 0 days.

(21) Appl. No.: 09/862,177

(22) Filed: May 21, 2001

(65) Prior Publication Data

US 2002/0083998 A1 Jul. 4, 2002

Related U.S. Application Data

(63) Continuation of application No. 09/500,548, filed on Feb. 9, 2000, now Pat. No. 6,407,858, which is a continuation of application No. 09/501,099, filed on Feb. 9, 2000, now Pat. No. 6,428,752, which is a continuation-in-part of application No. PCT/US99/00730, filed on Jan. 13, 1999, which is a continuation-in-part of application No. 09/122,216, filed on Jan. 24, 1998, now Pat. No. 6,269,846, and a continuation-in-part of application No. 09/079,324, filed on May 14, 1998, and a continuation-in-part of application No. 09/006,344, filed on Jan. 13, 1998, now abandoned.

(51) Int. Cl.$^7$ ................................................ B05C 1/00
(52) U.S. Cl. ..................... 141/1; 141/279; 422/100; 436/180; 118/243; 118/263; 427/256
(58) Field of Search .................. 141/1, 130, 279; 222/583; 422/100; 436/180; 118/401, 243, 263; 427/256

(56) References Cited

U.S. PATENT DOCUMENTS 2,868,020 A    1/1959    Williams, Jr. ................. 73/432

(List continued on next page.)

FOREIGN PATENT DOCUMENTS

EP    0 373 203    6/1990

(List continued on next page.)

OTHER PUBLICATIONS

Castellino, Alexander M.; "When the Chips are Down"; *Genome Research*; vol. 7, No. 10; (1997), pp 943–946.

(List continued on next page.)

*Primary Examiner*—Gregory L. Huson
*Assistant Examiner*—Peter deVore
(74) *Attorney, Agent, or Firm*—Philip L. McGarrigle; Alan B. Sherr; Ivan D. Zitkovsky

(57) ABSTRACT

For depositing fluid dots in an array, e.g., for microscopic analysis, a deposit device, e.g. a pin, cooperating with a fluid source defines a precisely sized drop of fluid of small diameter on a drop carrying surface. Transport mechanism positions the device precisely over the receiving surface and drive mechanism moves the deposit device toward and away from the surface. By repeated action, minute drops of fluid can be deposited precisely in a dense array, preferably under computer control. The drop-carrying surface shown has a diameter less than 375, preferably less than 300, preferably between about 15 and 250 micron, and is bound by a sharp rim that defines the perimeter of the fluid drop. The deposit device is compliant in the direction of deposition motion, e.g. by overcoming resistance of a resilient member. When depositing, the deposit device is laterally constrained to a reference position, e.g. by flexure mounting or the deposit device is mounted to displace from its mounting upon engagement with the receiving surface, and is subject to a lateral force or turning moment that engages the device with a lateral reference surface. A mobile-fluid storage device resupplies the deposit device along the array, e.g. in the immediate vicinity of the deposit locations. Mobile annular storage rings are lowered and raised to obtain a supply of fluid, or a mobile multiwell plate is used. Cleaning mechanism, sampling plans, and array products on microscope slides and fragile or soft membranes are disclosed as are many types of fluid and uses, e.g., in biotechnology, analysis and process control.

36 Claims, 30 Drawing Sheets

U.S. PATENT DOCUMENTS

| | | | |
|---|---|---|---|
| 3,329,964 A | 7/1967 | Mutschier et al. ............ 346/78 |
| 3,334,354 A | 8/1967 | Mutschier ................... 346/140 |
| 3,356,462 A | 12/1967 | Cooke et al. ............... 422/102 |
| 3,407,018 A | 10/1968 | Miller ........................ 359/896 |
| 3,568,735 A | 3/1971 | Lancaster ................... 141/238 |
| 4,041,995 A | 8/1977 | Columbus ................... 141/275 |
| 4,096,825 A | 6/1978 | Golias et al. ............... 118/221 |
| 4,142,656 A | 3/1979 | Smith et al. ................ 222/325 |
| 4,322,063 A | 3/1982 | Fishbeck et al. ............ 267/160 |
| 4,340,390 A | 7/1982 | Collins et al. ................ 23/230 |
| 4,387,384 A | 6/1983 | Sue ............................. 346/140 |
| 4,434,672 A | 3/1984 | Williamson et al. ..... 73/864.22 |
| 4,441,532 A | 4/1984 | Hrubesh ....................... 141/1 |
| 4,452,899 A | 6/1984 | Alston ......................... 436/46 |
| 4,565,094 A | 1/1986 | Sedgewick ................... 73/432 |
| 4,567,585 A | 1/1986 | Gelbart ........................ 369/97 |
| 4,627,009 A | 12/1986 | Holmes et al. ............. 364/559 |
| 4,635,488 A | 1/1987 | Kremer ................... 73/864.22 |
| 4,656,007 A | 4/1987 | Douchy et al. ............... 422/64 |
| 4,659,677 A | 4/1987 | Glover et al. ............... 436/174 |
| 4,688,908 A | 8/1987 | Moore ........................ 359/393 |
| 4,737,344 A | 4/1988 | Koizumi et al. ............. 422/100 |
| 4,832,474 A | 5/1989 | Yoshinaga et al. .......... 359/393 |
| 4,891,526 A | 1/1990 | Reeds ..................... 250/442.1 |
| 4,981,783 A | 1/1991 | Augenlicht .................... 435/6 |
| 5,051,594 A | 9/1991 | Tsuda et al. ........... 250/442.11 |
| 5,160,378 A | 11/1992 | Tuunanen et al. ............ 134/25 |
| 5,186,982 A | 2/1993 | Blette ......................... 427/256 |
| 5,202,231 A | 4/1993 | Drmanac ................... 422/100 |
| 5,204,268 A | 4/1993 | Matsumoto .................. 436/44 |
| 5,213,764 A | 5/1993 | Kerr et al. .................. 422/100 |
| 5,223,225 A | 6/1993 | Gautsch ...................... 422/100 |
| 5,224,088 A | 6/1993 | Atiya .......................... 369/97 |
| 5,234,530 A | 8/1993 | Freeman, III ............... 156/358 |
| 5,262,128 A | 11/1993 | Leighton et al. ............ 422/100 |
| 5,306,510 A | 4/1994 | Meitzer ....................... 422/65 |
| 5,323,712 A | 6/1994 | Kikuiri ...................... 359/393 |
| 5,337,178 A | 8/1994 | Kung et al. ................ 359/393 |
| 5,338,688 A | 8/1994 | Deeg et al. ................. 436/180 |
| 5,344,666 A | 9/1994 | Levine ...................... 427/2.11 |
| 5,351,925 A | 10/1994 | Druais ....................... 248/325 |
| 5,428,690 A | 6/1995 | Bacus et al. ................ 382/128 |
| 5,436,129 A | 7/1995 | Stapleton ........................ 435/6 |
| 5,443,791 A | 8/1995 | Cathcart et al. ............. 422/65 |
| 5,461,237 A | 10/1995 | Wakamoto et al. ......... 250/548 |
| 5,492,806 A | 2/1996 | Drmanac et al. .............. 435/5 |
| 5,525,464 A | 6/1996 | Drmanac et al. .............. 435/6 |
| 5,540,891 A | 7/1996 | Portmann et al. ........... 422/102 |
| 5,551,487 A | 9/1996 | Gordon et al. ................. 141/1 |
| 5,583,691 A | 12/1996 | Yamane et al. ............. 359/393 |
| 5,607,861 A | 3/1997 | Komatsu et al. ............. 436/50 |
| 5,626,740 A | 5/1997 | Seto et al. .................. 205/789 |
| 5,665,312 A | 9/1997 | Sperber et al. ............... 422/81 |
| 5,700,637 A | 12/1997 | Southern et al. |
| 5,756,050 A | 5/1998 | Ershow et al. .............. 422/100 |
| 5,770,151 A | 6/1998 | Roach et al. ................. 422/63 |
| 5,800,992 A | 9/1998 | Fodor et al. ................... 435/6 |
| 5,807,522 A | 9/1998 | Brown et al. ................. 422/50 |
| 5,834,062 A | 11/1998 | Johnson et al. ............. 427/256 |
| 5,882,930 A | 3/1999 | Baier ........................... 436/49 |
| 5,895,630 A | 4/1999 | Skaborn et al. ............. 422/100 |
| 5,939,022 A | 8/1999 | Franciskovich ............. 422/100 |
| 6,269,846 B1 * | 8/2001 | Overbeck et al. ............... 141/1 |

FOREIGN PATENT DOCUMENTS

| | | |
|---|---|---|
| WO | WO 95/04594 | 3/1995 |
| WO | WO 95/09248 | 4/1995 |
| WO | WO 98/55852 | 12/1998 |
| WO | WO 99/36760 | 7/1999 |

OTHER PUBLICATIONS

Ekins, R.P., et al.; "Multianalyte Immunoassay: The Immunological "Compact Disk" of the Future"; *Journal of Clinical Immunoassay*; vol. 13, No. 4; (1990), pp 169–181.

NORMAG, Northern Magnetics Inc., company brochure.

NORMAG, "Single Axis High Performance Linear Stepper Motors", product description, pp 1.

The Perfect Solution for Your Testing Problem, ©Ostby Barton, (1997); product description, pp 1.

BioRobotics, "The MicroGrid", product description, pp 2.

"Gridding & Replicating Application", Revised: Nov. 1997 *PBA Technology Ltd..*, pp 1–2.

Geysen, H.M., et al.; "Strategies for epitope analysis using peptide synthesis"; *Journal of Immunological Methods*; vol. 102; (1987), pp 259–274.

Graves, David J., et al.; "System for Preparing Microhybridization Arrays on Glass Slides"; *Analytical Chemistry*; vol. 70, (1998) pp 5085–5092.

Kalachikov, S., et al.; Colony Selection with an Automated 383–Pin High–Density Replicating Tool (HDRT); BioRobotics, ©1996 Beckman Instruments, Inc.; pp 1–7.

Lemieux, B., et al.; "Overview of DNA chip technology"; *Molecular Breeding*; vol. 4, (1998); pp 277–289.

Southern et al.; "Molecular Interactions on microarrays"; The Chipping Forecast; *Nature Genetics*; vol. 21, pp, 5–9; Jan. 1999.

Front et al., "Workshop on Methods and Applications of DNA Microarray Technology"; Jan. 11–13, 1998.

"Microfiltration Apparatus"; *Chromatography Electrophoresis Immunochemistry Molecular Biology HPLC*; catalogue M 1987.

Hames et al.; "Nucleic Acid Hybridization; A Practical Approach "; *IRL Press* Oxford England; 1985.

"BioRobotics Latest Developments"; BioRobotics, Beckman Instruments, Inc.; 1997.

Abstracts of papers presented at the 1994 meeting on Genome Mapping & Sequencing; pp. 48, 60–62, 198, 203, 296–297; May 11–15, 1994.

Gilson; "Raising The Speed Limit on Liquid Handling . . . Again!" advertisement p 1.

Pease et al.; "Light–generated oligonucleotide arrays for rapid DNA sequence analysis"; *Proc. Natl. Acad. Sci. USA*; vol. 91, pp. 5022,5026, May 1994.

* cited by examiner

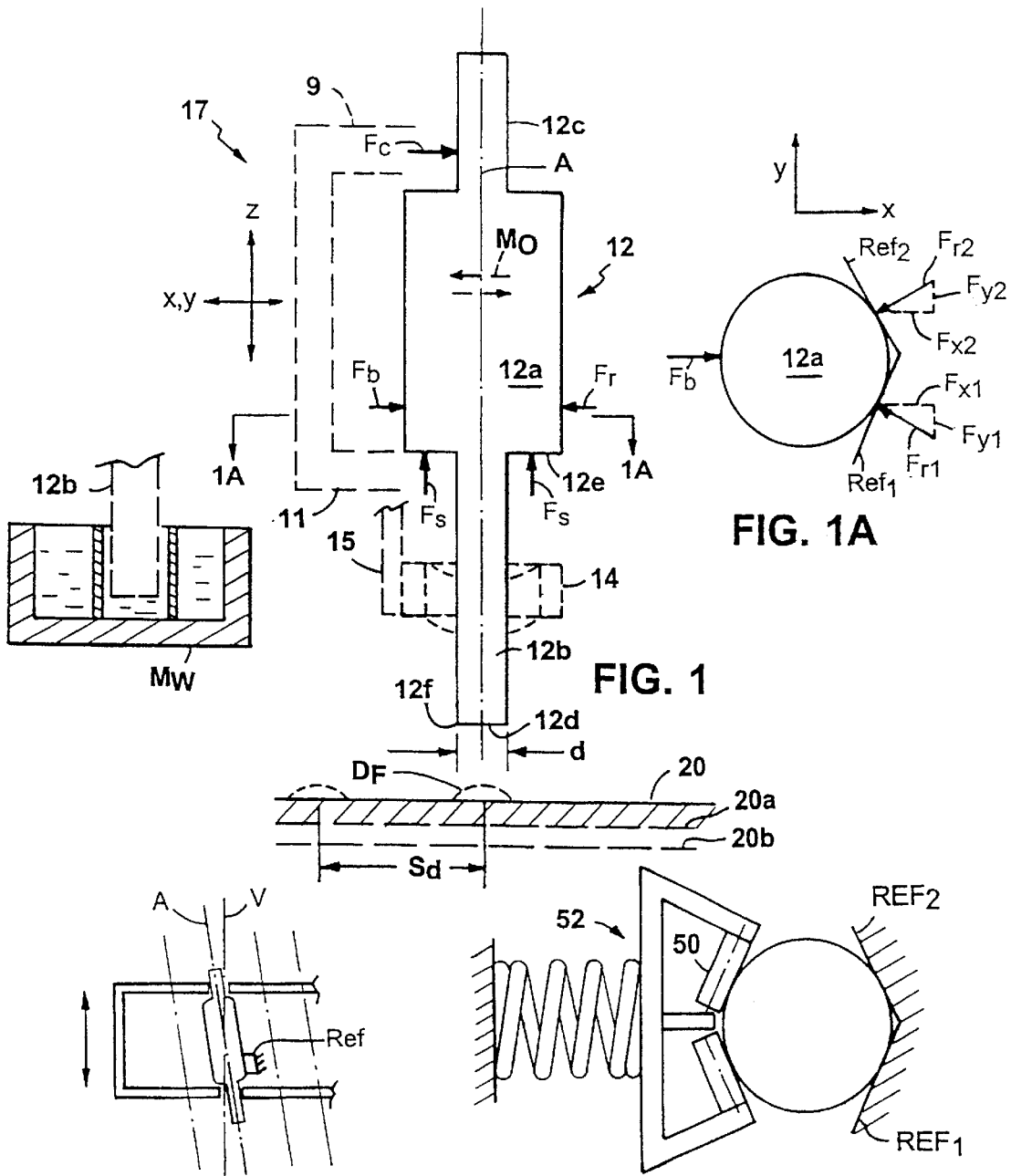

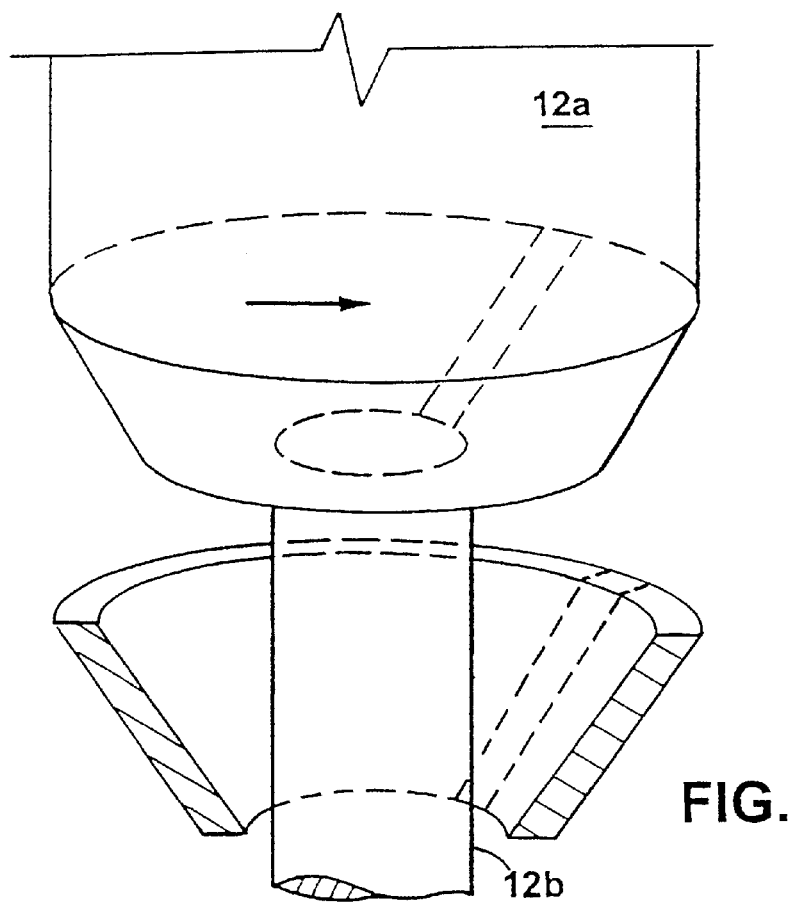
FIG. 1D
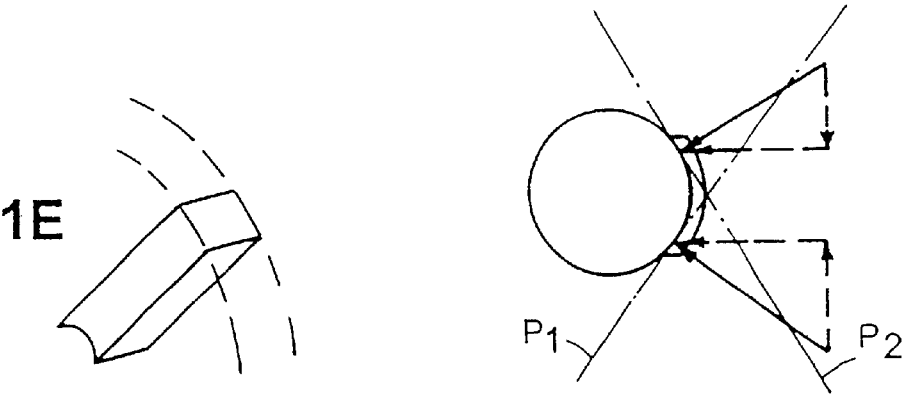
FIG. 1E
FIG. 1F

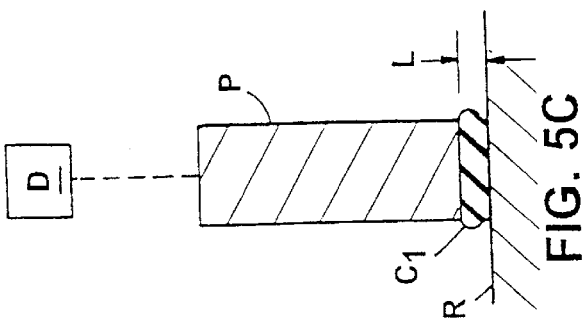
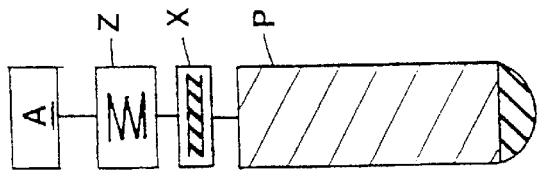
FIG. 5C
FIG. 1G
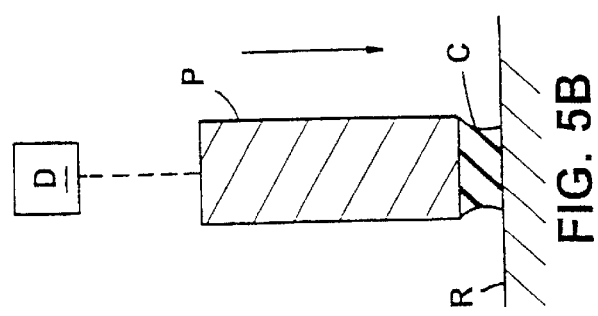
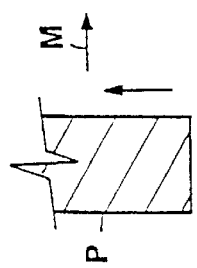
FIG. 5B
FIG. 5E
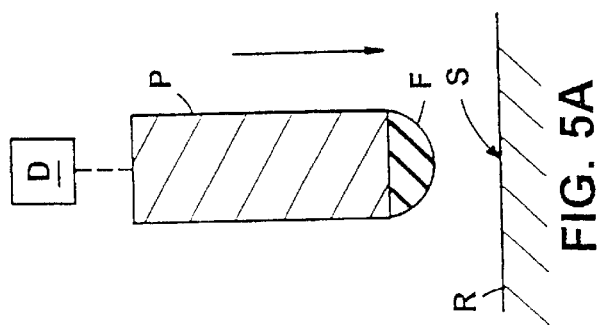
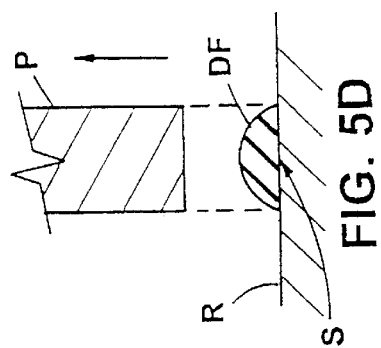
FIG. 5A
FIG. 5D

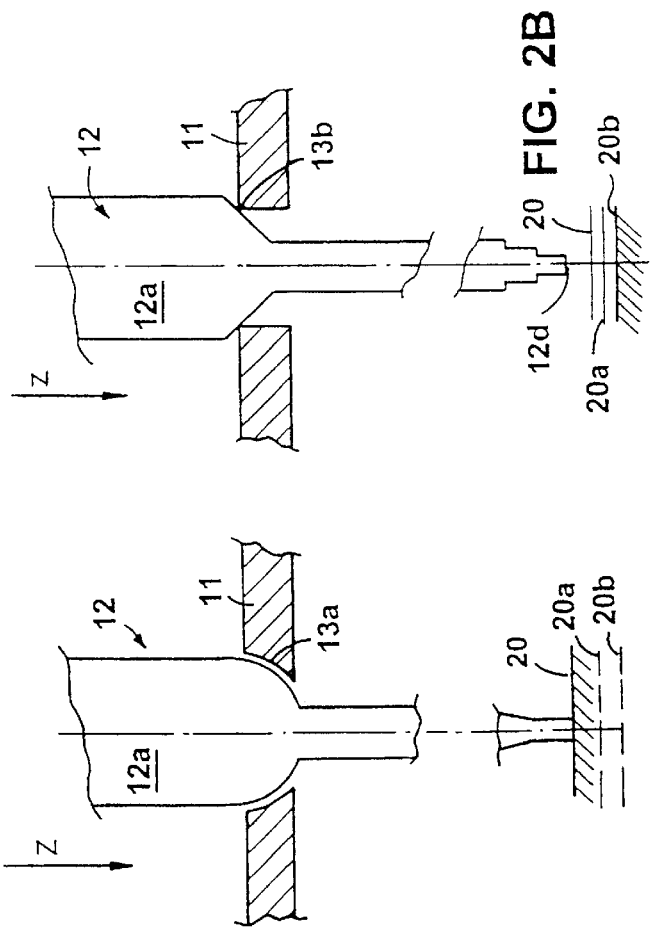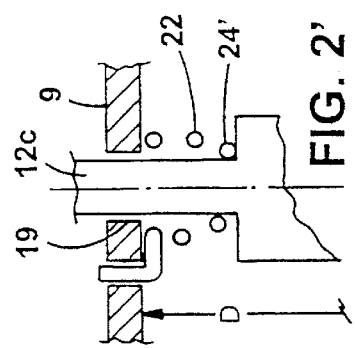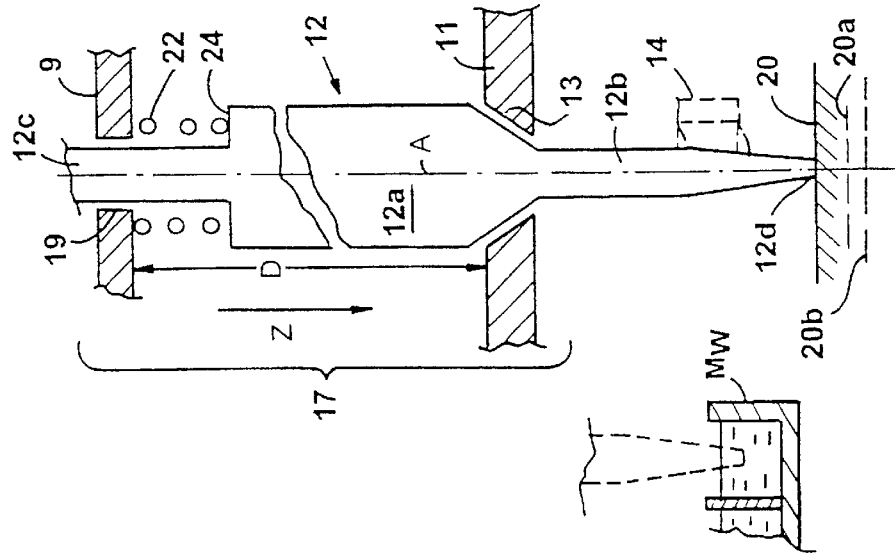

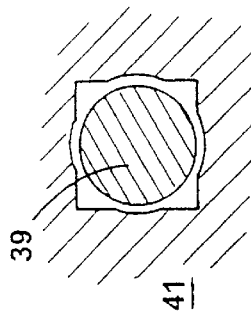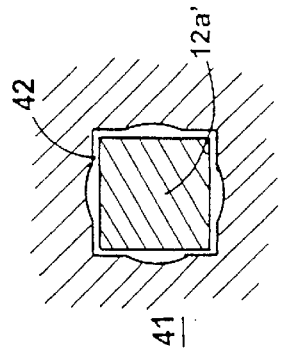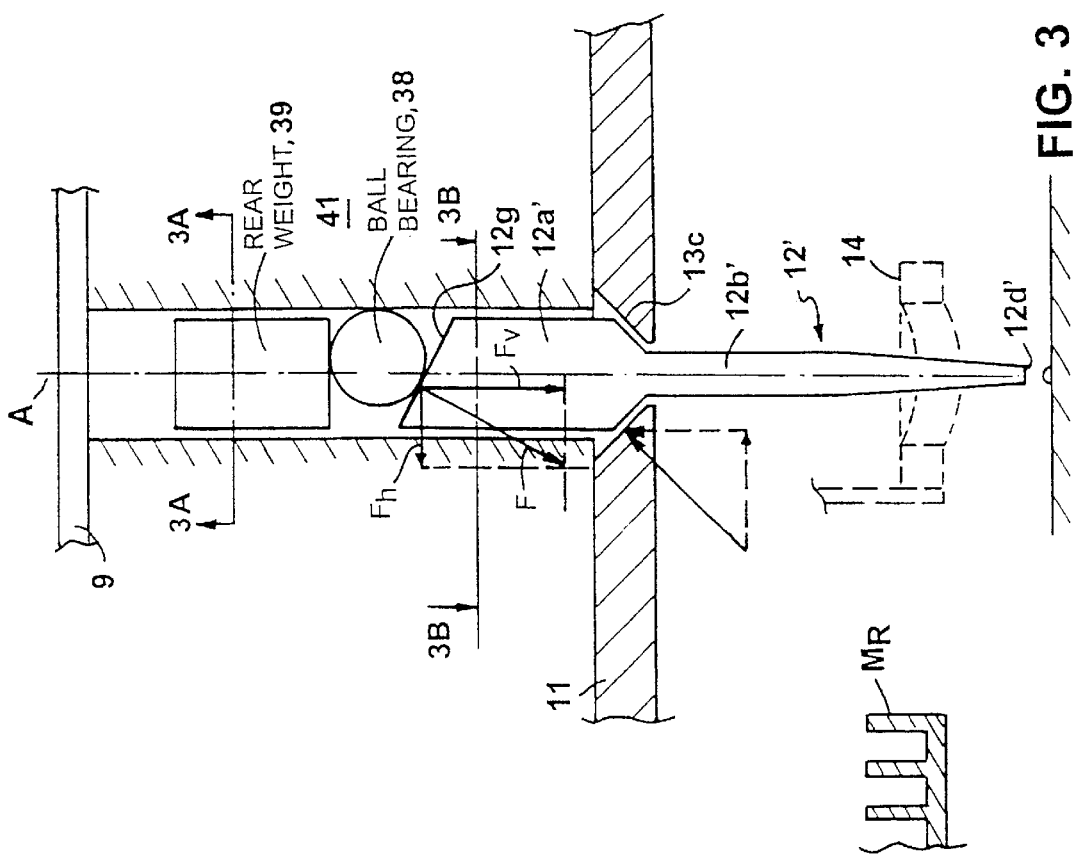

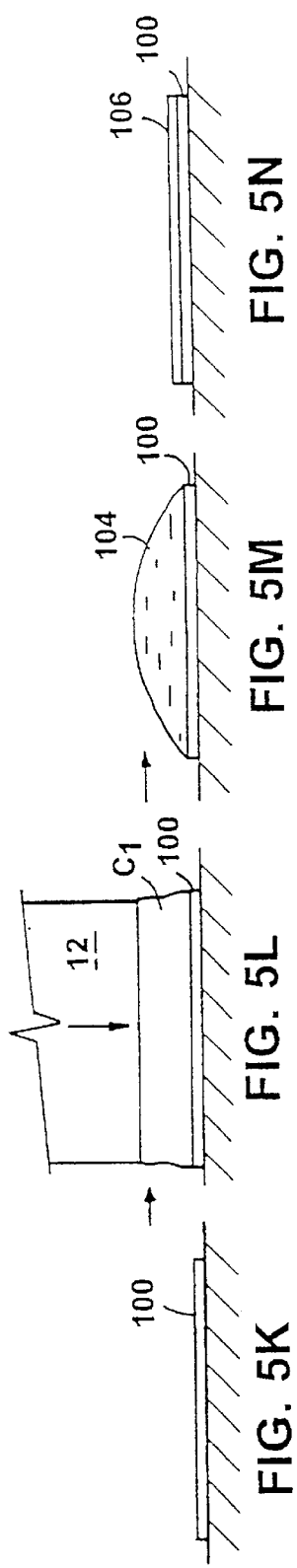
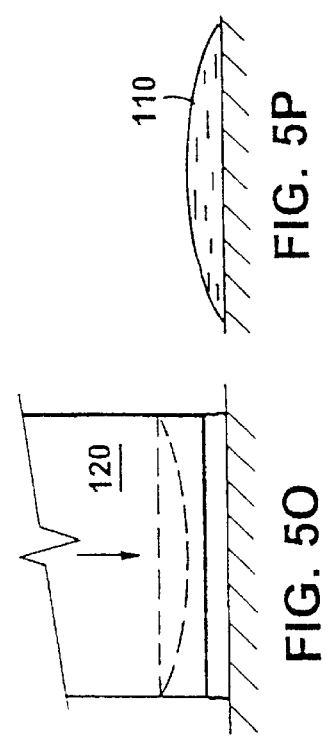
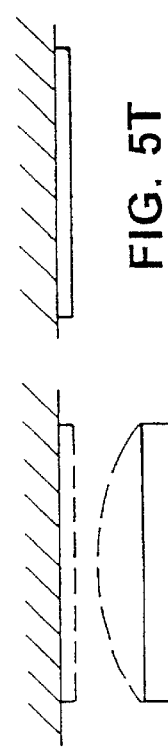
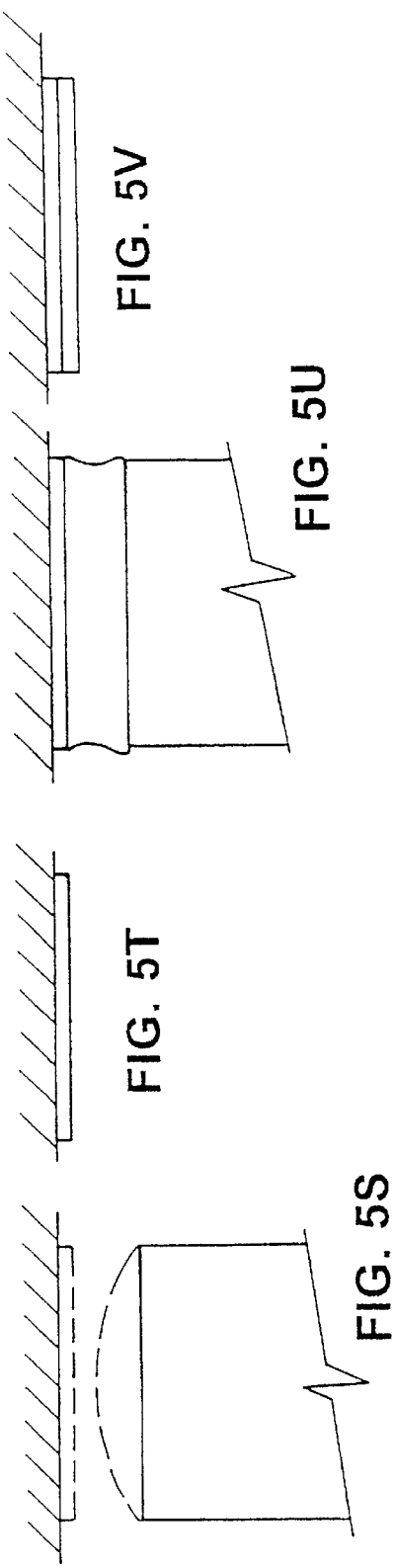

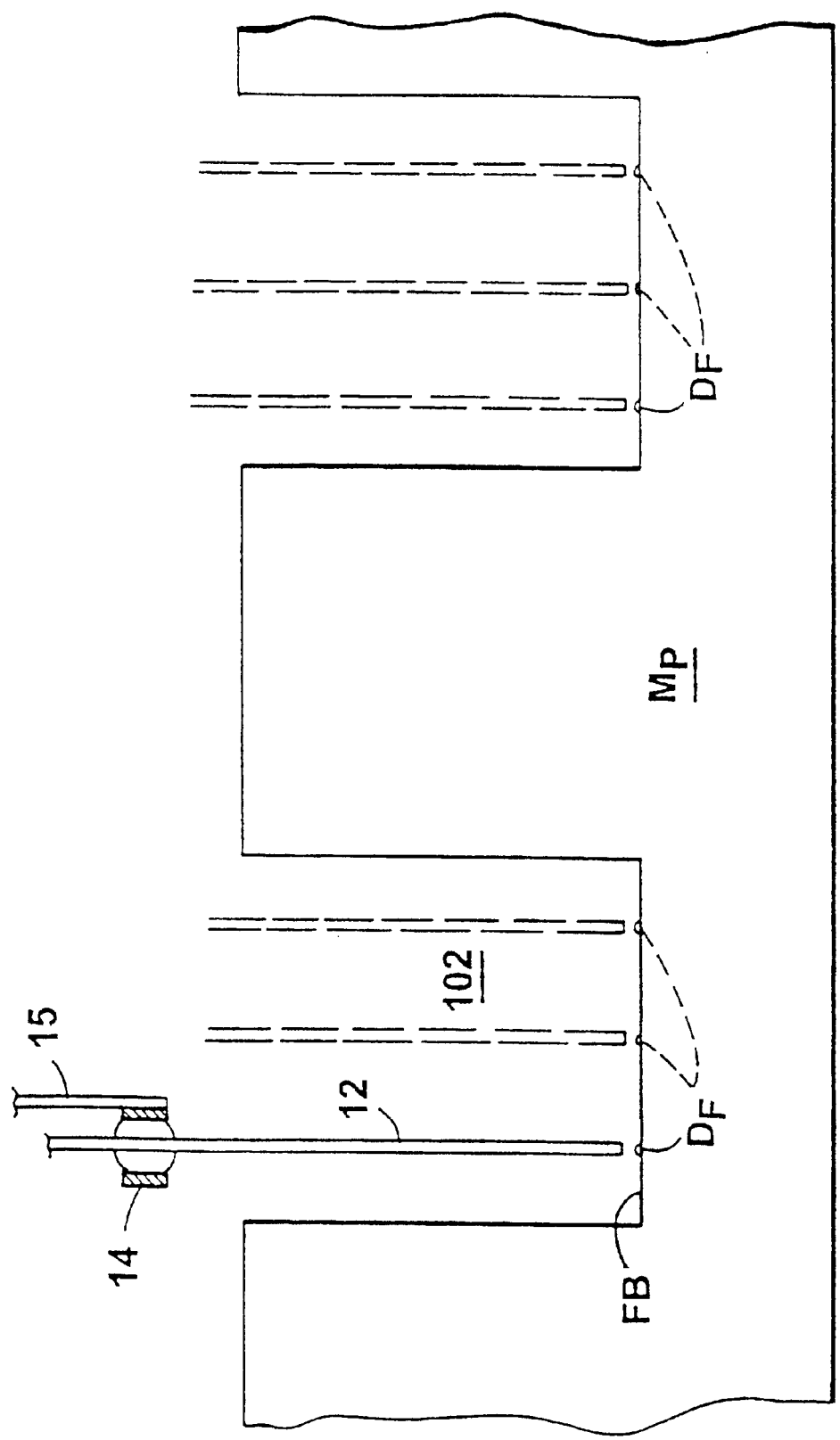

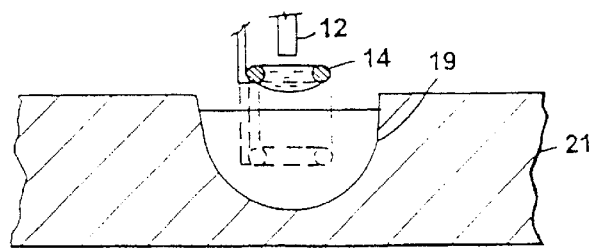
FIG. 9E
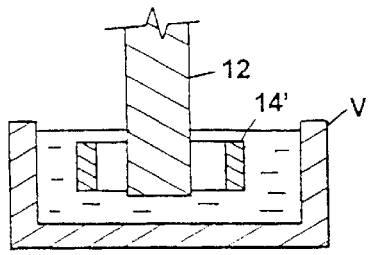
FIG. 9F
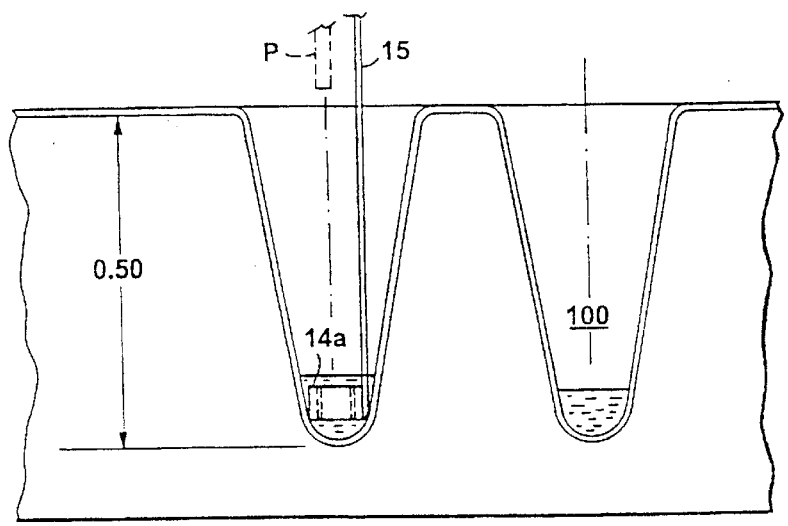
FIG. 9H
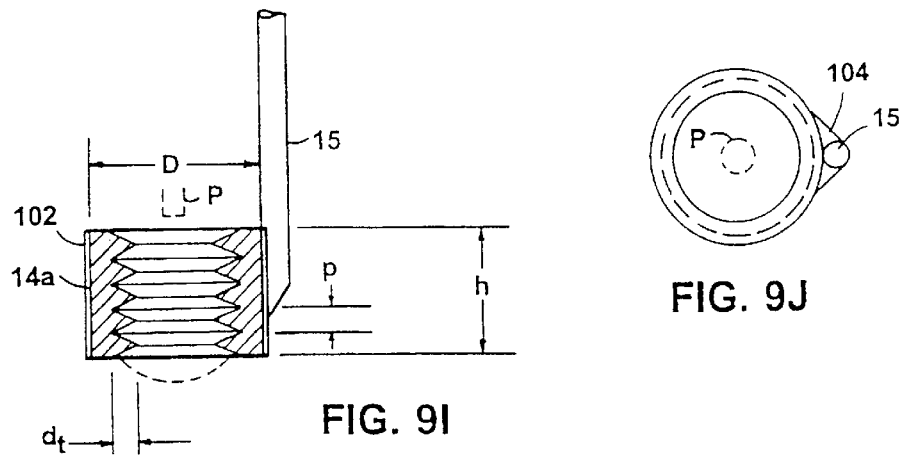
FIG. 9I
FIG. 9J

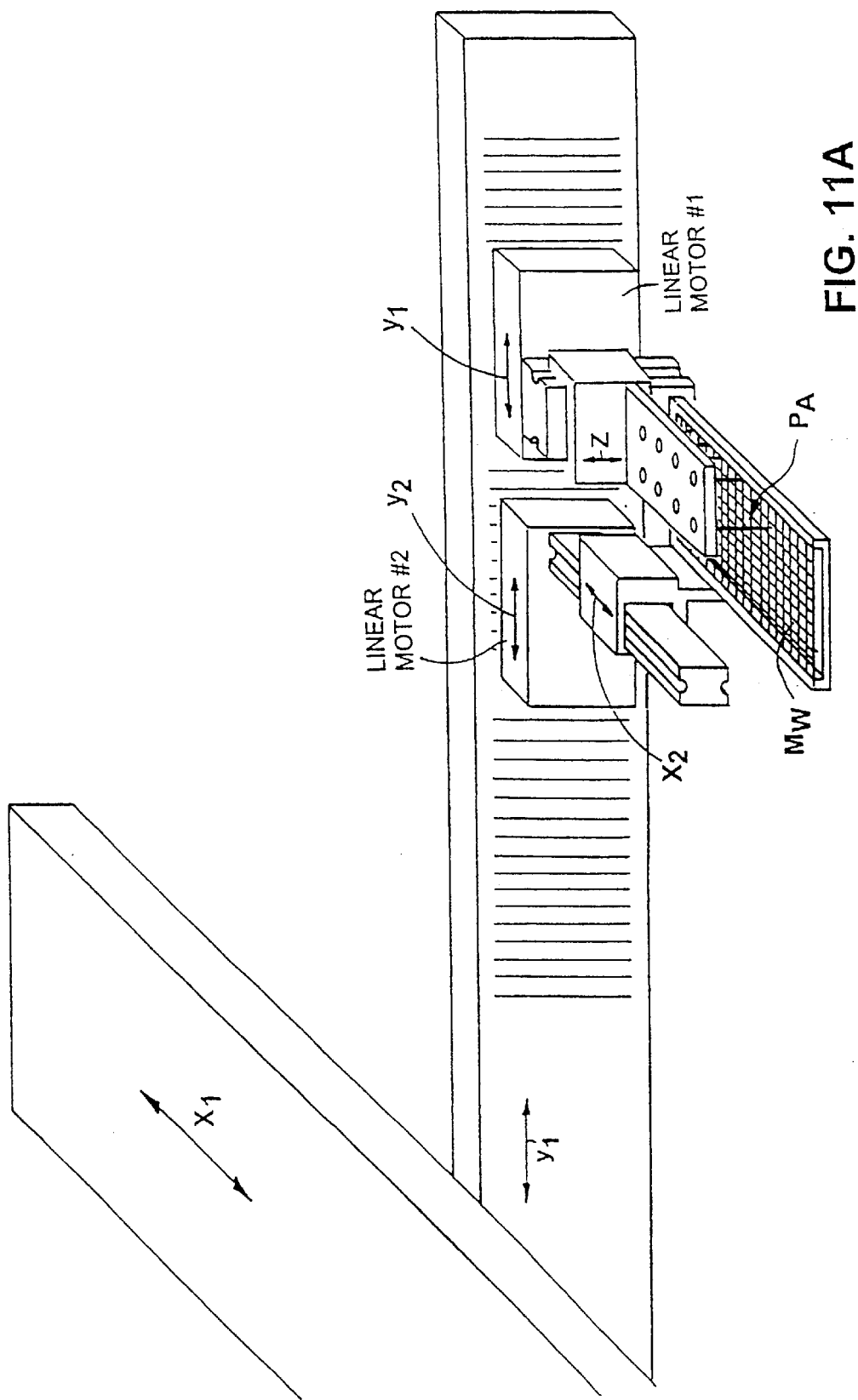

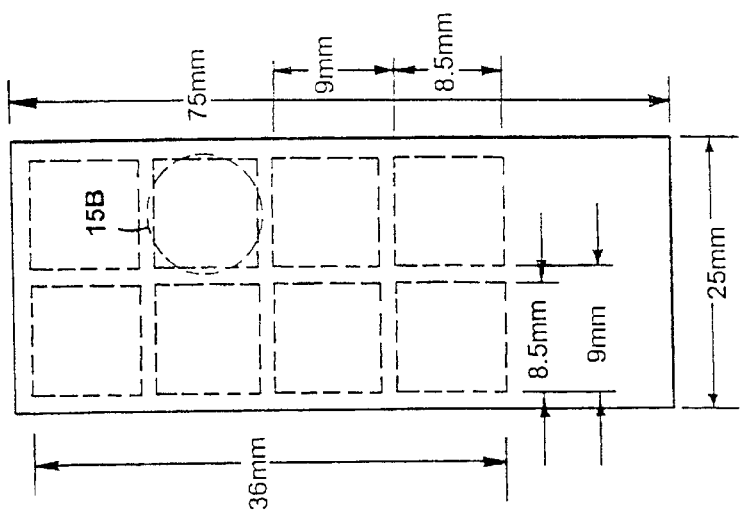
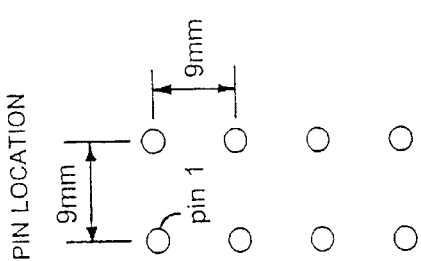

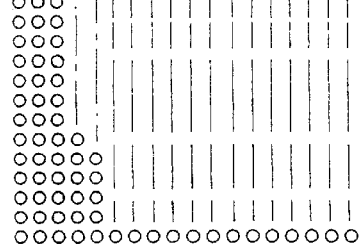
FIG. 16
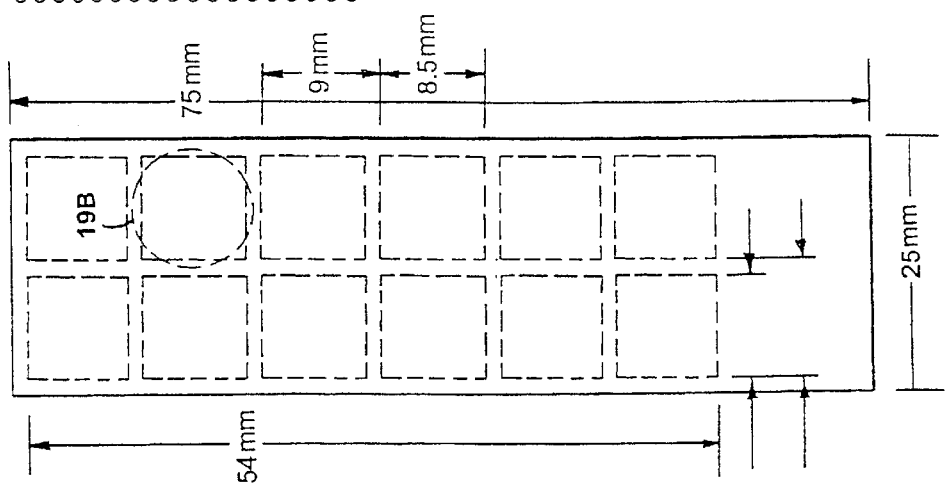
FIG. 19B
FIG. 19
The pin assembly follows the pattern
COL A ROW 1
COL C ROW 1
COL E ROW 1
COL G ROW 1
COL A ROW 7
COL C ROW 7
COL E ROW 7
COL G ROW 7
FIG. 18
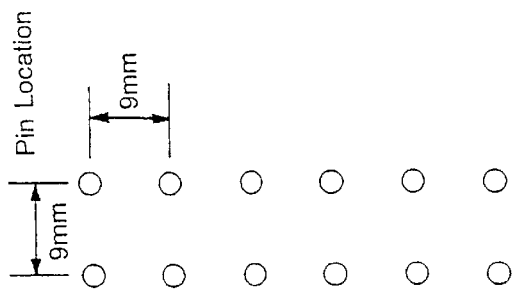
FIG. 17

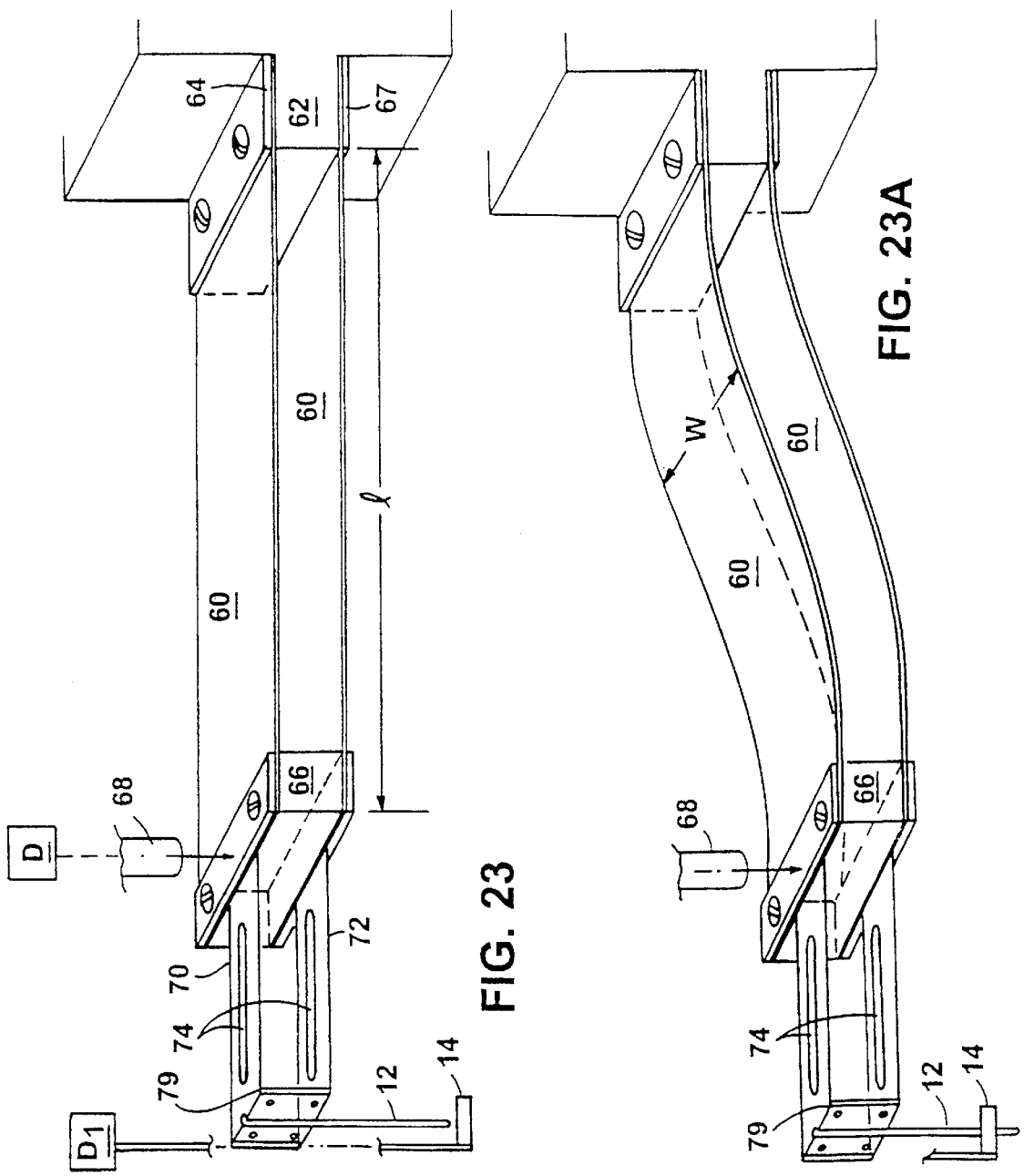

DEPOSITING FLUID SPECIMENS ON SUBSTRATES, RESULTING ORDERED ARRAYS, TECHNIQUES FOR ANALYSIS OF DEPOSITED ARRAYS

This application is a continuation, and claims priority under 35 U.S.C. §120, from U.S. application Ser. No. 09/500,548 filed on Feb. 9, 2000, now U.S. Pat. No. 6,407,858 and U.S. application Ser. No. 09/501,099 filed on Feb. 9, 2000 now U.S. Pat. No. 6,428,752 both of which claim priority from PCT Application No. PCT/US99/00730 filed on Jan. 13 1999; which is a continuation-in-part of U.S. application Ser. No. 09/122,216, filed on Jul. 24, 1998; and a continuation-in-part of U.S. application Ser. No. 09/079,324, filed on May 14, 1998; and a continuation-in-part of U.S. application Ser. No. 09/006,344, filed on Jan. 13, 1998 now abandoned. The disclosure of all of the above-mentioned applications is considered part of, and is incorporated by reference in, the disclosure of this application.

BACKGROUND OF THE INVENTION

The invention relates to the deposit upon substrates of small quantities of fluid in a precise manner and in arrays of desired density and consistency. The invention is useful, for instance, in carrying out reactions, in providing accurate overlays of deposits, and, in particular, in preparing microscope slides and membranes with biological materials.

The invention also relates to array products produced by the novel deposit techniques and to methods of analysis that employ the deposit techniques.

In the field of biochemistry it is desirable to accurately and efficiently deposit tens, hundreds, thousands and tens of thousands of samples of differing compositions on reaction or examination areas. Improvement in the speed of deposition, the precision of the size, shape, quantity and location of the deposits and the control over density of the deposits can lead to important advantages.

In particular, well developed biological analytical technology, and recently developed "Lab on a Chip" or "Gene Chip" techniques require creation of dense arrays of fluorescently labeled micro-organisms and DNA assays in a two dimensional field. It is desirable to place the arrays on a conventional microscope slide, and to create many such slides simultaneously in a manufacturing process.

In important applications, single stranded DNA or PNA or other biological elements in the form of fragments carrying known information are distributed onto the surface of a planar field array containing up to possibly 100,000 objects per microscope slide. The objects of the array represent discriminating sequence information. Different laboratories have targeted the objects of the array to have various spot sizes over a range of the order of 25 to 250 $\mu$m in diameter, depending primarily upon the total number of objects anticipated in the array. The objects of the array are probed with fluorescently labeled fragments of potential complementariTy. When a match occurs between these fragments and hybridization occurs, a positive is scored by observing fluorescence at the site of hybridization. By manipulating the deposition of complementary strands or fragments into the array and scoring "hits", many levels of information can be inferred.

For gene chip technology to proceed to complete fruition, as well as to improve the application of previous analytical techniques, economical instruments have been needed that can rapidly and accurately create the dense array of objects over a large field portion of a glass microscope slide or slide-like member that occupies an area approximately 22 mm wide and 50 mm long of a slide that is nominally 25 mm×75 mm.

In the deposition upon a microscope slide of discrete, minute quantities of a large variety of fluid materials, the volume deposited at a discrete spot typically may be from a few pico liter to a fraction of a micro liter, depending upon the application. The biological material carried in this fluid can range from a few strands of short oligonucleotides in a water solution to a high concentration of long strands of complex proteins. The properties of these fluids vary enormously. Some are akin to water while others are far more viscous, resembling a light oil or honey. The range of fluids that may be employed also exhibits wide differences in evaporative characteristics and in other properties.

Such large range of property variations in fluids of interest has caused great difficulties for any single type of process to operate over a wide range.

Certain processes employing photolithographic techniques have offered excellent positional accuracy of the objects and high dot density but have great limitations due to cost and due to the limited range of biological and chemical techniques and substrates that are applicable. These techniques typically construct short segments of DNA or other molecules by adding single bases, one at a time.

Certain other processes for forming arrays of dots of biological material have utilized piezo micro cylinders to aspirate and jet small volumes of fluid containing the material while others have used processes akin to a fountain pen, comprising a "quill" deposition tool. An assemblage of quills suck up a desired amount of fluid and by tapping a quill upon the receiving substrate, the meniscus holding the fluid in the gap of the quill breaks, due to inertia of the fluid within the suddenly stopped tool, so that a drop of fluid is effectively propelled from inside the quill to the impacted surface.

The development of such techniques has occurred against the background of the quite old technique for forming much larger deposits, of transferring a portion of fluid by a pin or a set of pins that are e.g. dipped in a fixed reservoir containing fluid to be transferred and moving the pins into position to contact a usually soft substrate to form relatively large spots. Some of these instruments are known as "replicators". An example of a product produced by such prior pins would be a 22 cm×22 cm bioassay plate carrying 0.6 mm diameter spots located on a grid 1 mm on center. This spot density is approximately 3 orders of magnitude too low from that needed for current "Gene Chip" applications, and the previously known techniques are impractical for present purposes for a number of other reasons as well.

SUMMARY OF THE INVENTION

One purpose of the invention is to provide a technology adapted to the deposition of very small drops of fluids, e.g. drops that form spots of less than about 375 or 300 $\mu$m diameter, and in important cases much smaller than that, and at correspondingly high densities (as used in this application, the term fluid "drop" refers to a very small quantity of fluid, and not to any particular shape of the fluid volume). The fluids and the resultant dots permissibly exhibit a wide range of properties such as viscosity, evaporative characteristics, surface tension, wettability, surfactant characteristic, dynamic contact angle and free surface energy. These and numerous other objectives are achieved by a number of broad features and preferred embodiments which are individually novel and important and which in many cases cooperate to achieve highly effective results.

According to one aspect of the invention, an apparatus for depositing fluid dots on a receiving surface in an array suitable e.g., for microscopic analysis reaction and the like, is provided, comprising a deposit device and a fluid source which are cooperatively related to enable the deposit device to precisely size a drop of fluid of small diameter on a drop-carrying surface of the device, transport mechanism for positioning the device at a precisely referenced lateral position over the receiving surface and drive mechanism for moving the deposit device, relatively, in deposition motion toward and away from the surface, the apparatus adapted, by repeated action, to deposit the drops of fluid precisely in a desired array, preferably the apparatus being computer controlled.

Preferred embodiments have one or more of the following features.

The drop-carrying surface has a diameter less than 375 micron, preferably less than 300 micron, preferably between about 15 or 50 micron and 250 micron.

The drop-carrying surface is bound by a sharp rim that defines the perimeter of the drop of fluid.

The deposit device is a pin or pin-like structure having an end surface that carries the fluid drop, preferably the pin or pin-like structure having sides that intersect with the end surface to define a sharp peripheral drop-defining rim.

Another broad aspect of the invention is an apparatus for depositing fluid drops on a receiving surface per se, comprising a deposit device and a fluid source which are cooperatively related to provide to a drop-carrying surface of the deposit device a precisely sized drop of fluid, the deposit device being a pin or pin-like structure having an end surface that serves as the drop-carrying surface, the pin or pin-like structure having sides that intersect with the end surface to define a sharp peripheral drop-defining rim.

Preferred pins or pin-like structures have an end surface that is generally flat and side surfaces that are cylindrical and smooth.

In preferred cases the deposit device is mounted for compliance in the direction of the deposition motion when the deposit device engages the receiving surface, preferably the deposit device being compliantly displaceable by overcoming resistance of a resilient member or weight, preferably, when the deposit device is an axially slidable pin or pin-like structure, the means for urging comprises a coaxial spring or a weight acting on the pin or pin-like structure. Also preferably, the drive mechanism for the deposit device is constructed to overtravel beyond a level at which the compliantly displaceable deposition device engages the receiving surface.

In important cases the deposit device, at the time of deposit, is laterally constrained to a reference position, as by the deposit device being mounted on a flexure system that defines the referenced lateral position of the deposit device, or the deposit device is mounted in a manner permitting its displacement relative to its mounting upon its engagement with the receiving surface, at the time of engagement of the device with the receiving surface, the deposit device being subjected to a lateral force or turning moment that engages the deposit device with at least one lateral reference surface, preferably the deposit device being a pin or pin-like structure which is free to slide axially relative to its mounting upon engagement of the pin or pin-like structure with the receiving surface, and which is urged against the lateral reference surface by a spring, a weight such as the weight of the device, an eccentric weight, or the device being tilted, or by electrical or magnetic forces acting upon the pin or pin-like structure, to produce a lateral force or moment toward the reference surface.

In many important cases, the fluid source is a mobile fluid storage device that is movable relative to an array of deposit locations, the fluid storage device being constructed and arranged to resupply the deposit device at various locations along the array.

Another broad aspect of the invention is an apparatus for depositing fluid drops on a receiving surface, comprising a deposit device and a fluid source which are cooperatively related to provide to the deposit device a drop of fluid, transport mechanism for positioning the deposit device over a receiving surface and drive mechanism for moving the deposit device, relatively, in deposition motion toward and away from the receiving surface, the apparatus adapted, by repeated action, to deposit the drops of fluid in a desired array, the fluid source being a mobile fluid storage device that is movable relative to the array of deposit locations, the fluid storage device being constructed and arranged to resupply the deposit device at various locations along the array.

In preferred embodiments employing a mobile storage device, the deposit device and the mobile storage device are constructed to supply drops to the deposit device in the immediate vicinity of the deposit locations for respective drops, preferably the mobile fluid storage device and the deposit device being coupled for transverse motion relative to the array and decoupled for movement of the deposit device toward and away from the receiving surface.

In many cases the mobile storage devices are preferably constructed and arranged to be replenished from a remotely located large reservoir.

In many cases a mobile storage device holds a volume of fluid having a free surface into which the deposit device is lowered and raised to obtain a fluid drop, preferably the mobile storage device being constructed to store a multiplicity of isolated fluid volumes in the wells of a multiwell plate, the apparatus constructed to obtain its fluid from a selected volume of the plate.

In other important cases a mobile storage device defines a generally annular fluid retention surface or ring (the term "annular" or "ring" being used to refer broadly to a member that has opposed or adjacent, surfaces that can hold a mass of fluid between them by surface tension effects, accessible to a deposit device), and the deposit device is constructed to move within the annular retention surface from retracted to extended positions, in the retracted position the drop-carrying surface of the deposit device being retracted from the surface of fluid retained by the annular surface of the storage device, and in the extended position the drop-carrying surface of the deposit device being projected through and beyond the surface of the retained fluid.

Another broad aspect of the invention is an apparatus for depositing fluid drops-on a receiving surface in an array suitable for microscopic analysis, comprising a deposit device and a fluid source which are cooperatively related to provide to a drop-carrying surface of the deposit device a precisely sized drop, and a drive mechanism for moving the deposit device, relatively, in deposition motion toward and away from the receiving surface, the storage device defining a generally annular fluid retention surface, and the deposit device being constructed to move within the annular retention surface from retracted to extended positions, in the retracted position the drop-carrying surface of the deposit device being retracted from the surface of the fluid retained by the annular surface of the storage device, and in the extended position the drop-carrying surface of the deposit device being projected through and beyond the surface of the retained fluid.

In preferred embodiments, a member that defines an annular fluid retention surface is associated with a driver that moves the member relative to the deposit device to a replenishment volume in which the member is immersed to receive a supply of fluid.

In certain preferred embodiments the deposit device is a pin or pin-like structure e.g. having one or more of the features described above, the pin or pin-like structure being mounted within the confines of an annular fluid retention surface and arranged to move axially relative thereto.

Preferably, fluid retaining surfaces of the annular storage device have a hydrophilic surface, e.g. a surface roughness of at least 1000 microinch or a surface energy greater that about 2500 mN/m, preferably the surface comprising tungsten, and preferably, e.g. when cooperating with the annular member to pick up a supply of fluid the drop-carrying surface or tip of the deposit device has a surface of surface energy greater than about 2500 mN/m, preferably the surface comprising tungsten.

The apparatus of any of the aspects and preferred embodiments described preferably include a cleaning system and a control system adapted to control relative movement of the deposit device to a depositing relationship to the receiving surface and a cleaning relationship to the cleaning system.

Another broad aspect of the invention is an apparatus for depositing an array of dots on a receiving surface, comprising a deposit device in the form of a pin or pin-like structure having an end surface capable of precisely defining a small drop of fluid, a source of fluid for the deposit device, mechanism for moving the deposit device relatively over an array of spaced apart deposit locations of a receiving surface, mechanism for repeatedly moving the deposit device, relatively toward and away from the receiving surface to deposit respective drops of fluid at selected deposit locations, a cleaning system, and a control system adapted to control relative movement of the deposit device between a resupply relationship to the source, a depositing relationship to the substrate and a cleaning relationship to the cleaning system.

In embodiments in which the deposit device is associated with a mobile supply device that travels with it, the deposit device and mobile supply device are preferably movable together to the cleaning system in response to the control system, preferably the mobile supply device being an annular member through which the deposit device operates. Preferably the cleaning system has a nozzle for directing a flow of air past the annular structure, preferably a cleaning or drying station comprising a circular nozzle constructed to discharge a conical flow of fluid, preferably compressed air, high pressure liquid, an aerosol or heated air against a deposit device or mobile fluid source, preferably the deposit device being a pin or pin-like structure surrounded by a mobile reservoir in the form of an annular member capable of holding a supply of fluid by surface tension effects, the nozzle flows directed to dislodge retained fluid, to clean or to dry the respective parts; in some uses preferably an circular storage device is associated with a heater, e.g., an induction heater.

In certain preferred embodiments of the various aspects and features described, there are provided a set of at least two of the deposit devices, at least one fluid source for providing a drop of fluid on each deposit device, and mechanism for moving the pins together transversely over an array of spaced apart deposit locations of the receiving surface, preferably there being at least four of the deposit devices comprising a deposit head. Preferably the apparatus includes mechanism for repeatedly moving each deposit device independently, or mechanism for moving each deposit device simultaneously, relatively, toward and away from the receiving surface to deposit respective drops at respective deposit locations on the receiving surface.

For simultaneous actuation, preferably two or more deposit devices are mounted on a common support, driven by a common driver to deposit respective fluid drops on the receiving surface. In cases in which each deposit device is associated with a respective storage ring, the storage rings are also mounted on a common support, driven by a common drive; preferably the spacing of the rings corresponds to the spacing of a multiwell storage plate into which the rings are immersed for resupply. In cases in which the deposit device is lowered directly into fluid and raised to obtain its drop, preferably the spacing of the deposit devices corresponds to the spacing of wells of a predetermined multiwell plate, the multiwell plate being a mobile fluid supply that is constructed to accompany the deposit device across the substrate. In the case of supply rings or direct dipping of the deposit devices, preferably in the spacing corresponds to well-to-well spacing of wells of a 96, 384, 864 or 1536 well plate, or a spacing of 9 mm or a submultiple of 9 mm.

The various apparatus described preferably have one or more of the following features.

The deposit device and its mounting limits the force of engagement of the deposit device upon the receiving surface to less than 1 gram, preferably less than 0.5 gram, preferably to about 0.3 gram.

The deposit device has a natural frequency greater than 10 Hz, preferably greater than 20 Hz.

The motion of the deposit device toward and away from the receiving surface is damped, preferably by friction or by a damping material associated with the support of the deposit device.

The apparatus of any of the foregoing is preferably constructed to mount a number of microscope slides or slide-like structures to serve as the receiving surface, and a control system is constructed and arranged to deposit drops of fluid in selected locations on the slides or slide-like structures, preferably the fluid source comprising a source of biological fluid.

Another broad aspect of the invention is a fluid deposit assembly mounted on a carrier for depositing minute drops of fluid at selected locations upon a receiving surface, comprising a deposit device having an exposed tip, preferably of diameter of 375 or 300 micron or less, constructed and arranged to carry and deposit drops of fluid upon the surface, stable lateral reference surfaces or surface portions exposed for engagement by the deposit device, the surfaces or surface portions constructed and arranged to prevent lateral displacement of the deposit device relative to the carrier when the deposit device is urged thereagainst and means for urging the deposit device against the reference surfaces or surface portions at least at the time that the deposit device approaches the receiving surface to deposit a fluid drop, the reference surfaces or surface portions and the means for urging cooperating to position the deposit tip in a precisely desired position as it contacts the receiving surface.

Preferably, for depositing fluid drops in a dense array of mutually isolated dots, the assembly comprises a fluid source for repeatedly providing a discrete drop of fluid on the tip of the deposit device, mechanism for moving the device relatively over an array of spaced apart deposit locations of a receiving surface, mechanism for repeatedly moving the device, relatively, toward and away from the receiving surfaces to deposit respective dots at respective deposit locations on the surface, preferably the fluid source being a mobile fluid storage device separate from the deposit device, which is generally movable over the array of deposit locations, the fluid storage device being constructed and arranged to resupply the deposit device at various locations with respect to the array.

In certain preferred embodiments of this aspect also, the deposit device is a slidable pin or pin-like structure constructed and arranged to dip into a volume of fluid carried by a mobile storage device, preferably the storage device being constructed to store a multiplicity of isolated fluid volumes, the apparatus constructed to move the supply device relative to the deposit device to select the fluid to be deposited, preferably the storage device being a 96 well plate or a plate having a multiple of 96 wells, and also preferably including at least one driven stage for moving a selected well of a mobile multiwell plate into registry with the deposit device under computer control for enabling motion of the deposit device to dip into and out of the preselected well to provide a drop of the selected fluid to the device.

In other preferred embodiments the mobile storage device is an annular ring as described above.

In embodiments in which the deposit device is a pin or pin-like structure, it is preferably positioned by engagement with a surface of revolution whose axis is disposed at a predetermined relationship to the receiving surface or substrate, preferably the surface of revolution being in the form of a supporting ledge that supports the device from moving in its assembly in the direction toward the receiving surface, but from which the device is free to lift in response to contact of the tip of the device with the receiving surface as the supporting ledge and device are together moved relatively toward the receiving surface for depositing a drop, preferably the surface of revolution having a surface of form substantially matching the form of the portion of the device disposed to engage it, preferably the surfaces being respectively conical, each preferably conforming to a portion of the surface of a right cone.

In certain embodiments a means for urging the deposit device against reference surfaces applies a lateral force or turning moment to the deposit device, preferably the force or turning moment being applied by a spring bearing eccentrically on the device or by a pushing member engaged with a remote end of the deposit device, one of the engaged end and pushing member comprising a surface set at an acute angle to an axis of the device, and the other of the surfaces comprising a convexly curved surface engaged upon the angled surface, preferably the convexly curved surface defined by a confined ball that bears against the inclined surface, preferably by being pushed by a weight.

In embodiments in which the deposit device is in the form of a pin or pin-like structure, a structure prevents rotation of the deposit device about its own axis, preferably the pin or pin-like structure confined in a complementary space that prevents its rotation about its own axis or a detent prevents rotation of the deposit device, preferably the detent comprising part of a coil spring which surrounds and is frictionally secured to the pin or pin-like structure, a protrusion of the spring engaging a stop surface that prevents the rotation, preferably the spring also providing axial compliance to the pin or pin-like structure.

Another broad aspect of the invention is a deposit apparatus comprising a multiplicity of deposit devices as described, mounted for motion together in response to a common actuator, preferably the deposit devices comprising deposit pins or pin-like structures.

Another broad aspect of the invention is an apparatus comprising a mobile fluid storage device separate from a deposit device and generally movable over an array of deposit locations, the fluid storage device being constructed and arranged to resupply the deposit device at various locations with respect to the array, in one case, preferably the mobile fluid storage device being constructed to store a multiplicity of isolated fluid volumes, the apparatus constructed to move the mobile storage device relative to the deposit device to select the fluid to be deposited, preferably the deposit device being a pin or pin-like structure constructed and arranged, under computer control, to dip into a selected volume of fluid carried by the mobile fluid storage device, preferably the mobile fluid storage device being a multiwell plate having 96 wells or multiples of 96 wells, or a spacing of 9 mm or a sub-multiple of 9 mm and preferably the apparatus including a driven stage for moving the fluid storage device into registry with the deposit device under computer control for enabling dipping of the deposit device into a preselected fluid volume; in another case preferably the mobile storage device is an annular ring that retains a supply of fluid by surface tension.

The invention also features the method of use of all the described apparatus in depositing fluid drops, especially the fluids mentioned in the specification.

Another broad aspect of the invention is a method of depositing a biological compound on a substrate or causing biological compounds to interact with another substance at a predetermined position on a substrate, including the step of depositing at least one of the compound or substance in a precisely determined localized spot relative to the substrate by mechanically lowering a compliant deposit device, preferably a compliant pin or pin-like structure, to which a drop of the compound or substance is held by surface tension, toward the substrate until the pin or pin-like structure contacts the substrate or a pre-applied compound on the substrate and thereafter mechanically lifting the deposit device away from the substrate under conditions in which the fluid drop transfers to the substrate or the pre-applied compound on the substrate, preferably the deposit device, when approaching the substrate, applying a force to the substrate of less than about 1 gram, preferably less than 0.5 grams, preferably about 0.3 grams and preferably the drop being less than 300 micron in diameter, preferably less than 200 or 100 micron in some cases preferably superposed drops of both a compound and another substance being successively deposited by the said technique.

Preferably in certain cases the fluid supply of the biological compound or substance to be deposited by the pin or pin-like structure is obtained by dipping the pin or pin-like structure in fluid, or the deposit device is supported above the substrate at the deposit location within a ring holding fluid by surface tension, and the pin is moved through the ring in the manner that a relatively small drop of the fluid supply is held by the end of the pin or pin-like structure by surface tension, preferably in both cases the pin providing a drop-carrying surface bound by a sharp rim that sizes the drop.

Preferably the fluid to be deposited is fluid selected from a group of fluids disposed in a multiwell plate, either a plate which moves across the substrate to be in proximity to the deposit pin or pin-like structure, or a plate visited by an annular supply ring.

Another broad aspect of the invention is a method of producing arrays of fluid dots comprising providing an array of compliant deposit devices according to any of the foregoing claims, the devices preferably being in the form of pin or pin-like structures, the devices having spacings corresponding to the well spacing of a 96 well plate, or a plate having a multiple of 96 wells or a spacing of 9 mm or a submultiple of 9 mm, according to a sampling plan, preferably either dipping mobile annular supply rings into wells of the plate or dipping the devices directly into wells of the plate with which the device is registered to provide fluid drops on the devices and transferring the drops to respective locations in substantially denser arrays on a receiving surface, preferably the drops being deposited on a microscope slide in a pattern of square arrays.

In the various methods, preferably drops of fluid are deposited under computer control, by moving at least one compliantly mounted pin or pin-like structure having a drop-supporting surface of diameter less than about 375 microns, preferably less than 300 microns, preferably less than 250 micron, to a selected position and depositing, with the pin or pin-like structure, a desired material.

In the various methods, preferably the receiving surface is fragile, or soft, preferably the receiving surface is porous or microporous or fibrous, preferably comprising nitrocellulose, nylon cellulose acetate or polyvinylidene fluoride or a gel, preferably the member defining the soft or fragile receiving surface being mounted on a rigid carrier member, either directly or upon an intermediate soft or resilient buffer member.

Preferably the method is employed to deposit a fluid selected from the group of biological fluids described in the specification, preferably the material being a biological probe or a chemical for reaction with biological material, a fluorescing material, an ink, dye, stain or marker, a photoactive material, or a varnish or an encapsulant or an etchant, or a cleaning or neutralizing agent.

Another broad aspect of the invention is the method of depositing a biological fluid with a pin or pin-like structure comprising supporting fluid within a ring by surface tension, and moving the pin or pin-like structure through the ring in the manner that a relatively small drop of the fluid is held by to the end of the pin by surface tension and deposited on a receiving surface.

Preferably an array of deposits formed by any of the described methods is microscopically examined with a wide area scanning microscope.

The invention also features an array product comprising deposited dots of fluid of diameter less than about 375 micron diameter, preferably less than 300 micron, preferably between 15 or 50 and 250 micron, in a dense array in a pattern corresponding to a function of the distribution of wells of a 96 well plate, preferably the dots being spaced from each other in the array less than three times their diameter, preferably less than twice, or about one and one half times the dot diameter the deposits preferably residing upon a glass microscope slide or on a fragile or soft surface, preferably a porous or microporous surface, the surface preferably comprising nitrocellulose, nylon, cellulose acetate, polyvinylidine fluoride or a gel, the fragile or soft surface preferably mounted on a rigid support directly or via an intermediate soft or resilient buffer member.

BRIEF DESCRIPTION OF THE DRAWINGS

In the Figures:

FIG. 1 is a free body diagram of a deposit pin that is laterally constrained by being loaded against a reference surface. FIG. 1 also illustrates alternate mobile sub-reservoirs with which the deposit pin is employed.

FIG. 1A is a cross-section taken on line 1A—1A of FIG. 1.

FIGS. 1B and 1C are views similar to FIG. 1A illustrating other pin loading arrangements.

FIG. 1D is a diagrammatic perspective view of a deposit pin that has a conical surface mated with a complementary seating surface of a support plate, while FIG. 1E is a diagram of a longitudinal segment of the support seating surface and FIG. 1F is a diagrammatic view with vectors that analyze the reaction forces of the support seat in response to lateral biasing applied to the pin.

FIG. 1G is a representation of a spring-mounted and damped deposit pin.

FIGS. 2, 2A, 2B and 3 are diagrammatic side views of combinations of deposit pins and cooperating supports that provide lateral constraint of the pin, FIG. 2' is a preferred alternative arrangement of a portion of FIG. 2, while FIGS. 3A and 3B are cross-sectional views taken on respective section lines of FIG. 3.

FIG. 4 is a perspective view of a deposit pin mounted by a pair of parallel spring flexures by which it is laterally constrained and prevented from rotating about its own axis, the pin acting vertically through a mobile sub-reservoir while

FIGS. 5A–5E depict the action of a deposit pin depositing biological fluid or reagent, with light contact force, on a precisely located position on a receiving surface such as a microscope slide.

FIGS. 5F–5I depict the action of a pin depositing fluid on a fragile, porous or soft membrane or the like.

FIGS. 5K–5N illustrate the process of depositing one deposit upon another in a precisely aligned manner while FIGS. 5O–5R illustrate deposit of a large spot upon which small fluid dots are deposited.

FIGS. 5S–5V illustrate multiple deposits formed by vertically upward deposit motions.

FIG. 6 is a diagrammatic view of depositing dots of fluid on flat-bottomed wells of a multiwell plate.

FIG. 9 is a side view and FIG. 10 a top view of a deposit head, comprising a deposit pin and an annular sub-reservoir through which the deposit pin operates, while

FIG. 9E depicts supply or resupply of the sub-reservoir of FIG. 9.

FIG. 9F depicts cleaning the ring and pin of FIG. 9 at a cleaning station while

FIG. 9H depicts the narrow walls of the wells of a PCR plate and the supply of a sub-reservoir by immersion in a well.

FIG. 9I is a cross-sectional view of a presently preferred annular sub-reservoir device suitable for picking up low viscosity fluids from a narrow main supply as illustrated in FIG. 9H, while FIG. 9J is an end view of the device of FIG. 9I.

FIG. 9K is a magnified view of a pin and ring assembly in which the fluid contact surfaces are specially coated while

FIG. 11 is a perspective view of a multi-pin deposit head mounted for cooperation with a multiwell mobile supply reservoir while FIG. 11A shows the same elements as FIG. 11 in a supply relationship.

FIG. 12 is a diagram of an operable pin pattern of micro deposit pins while FIG. 13 illustrates the initial relationship of the pins to a standard 96 well supply plate.

FIG. 14 defines a useful sampling sequence for the pins of FIG. 12.

FIG. 15 illustrates a pattern of separated squares on a microscope slide which the pins of FIG. 12 can simultaneously address while FIG. 15B shows details of a square;

FIGS. 16, 17, 18, 19 and 19B are views similar, respectively, to FIGS. 12–15B, illustrating an arrangement employing a 12 pin pickup array used with a 96 well supply plate.

FIG. 21 is a perspective view of a particular device employing details of the pin design of FIG. 2, mounted for X,Y and Z travel as an array-forming device while

FIGS. 23 and 23A are perspective views of a combined weak and strong flexure mounting of a deposit pin at respectively different stages during operation.

PREFERRED EMBODIMENTS

Figure 4:
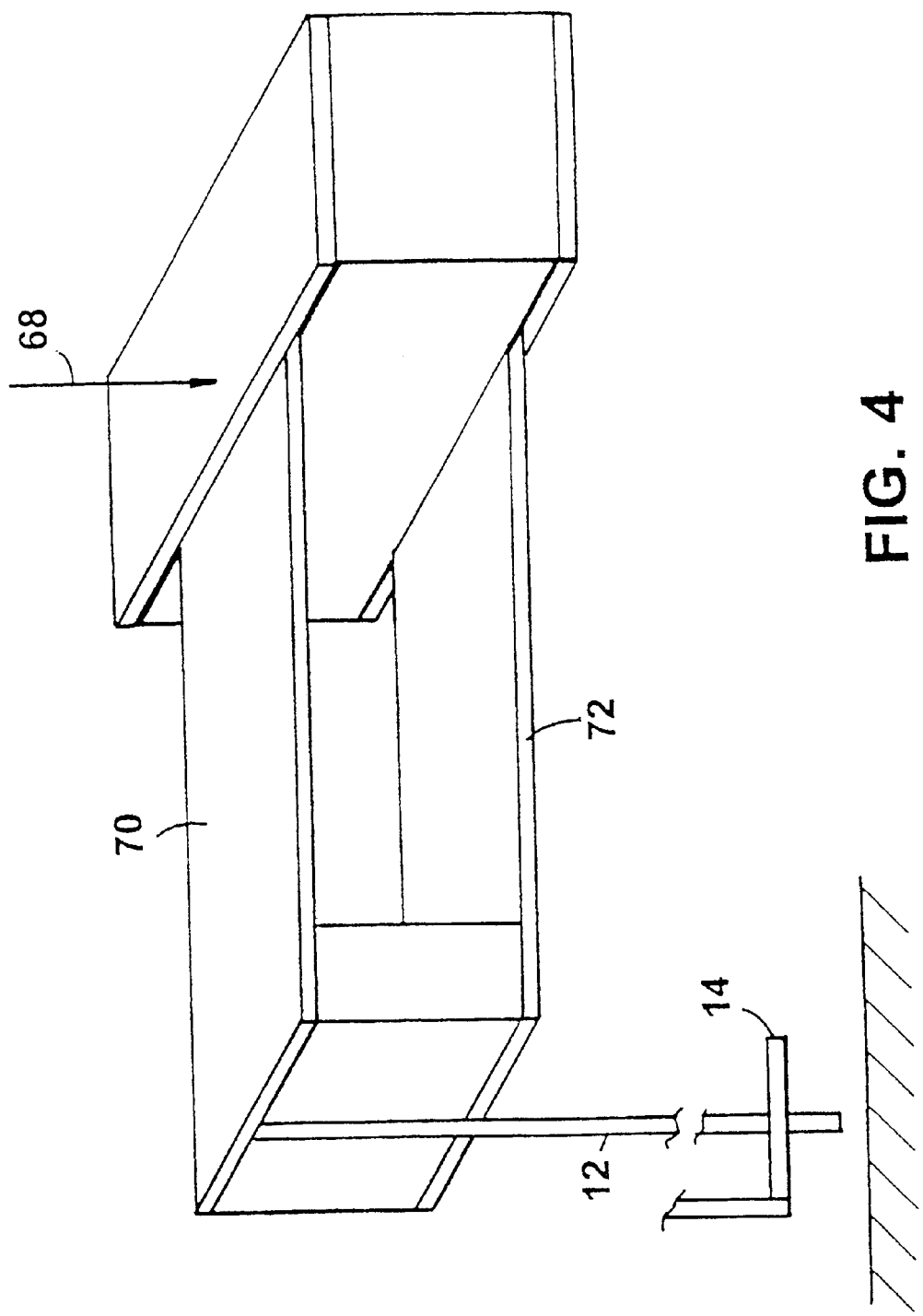

In preferred embodiments a deposit pin of small cross-section is employed with a mobile fluid reservoir to which the pin is repeatedly exposed, the pin being sized and shaped to define and retain on its tip a drop of fluid from the reservoir, the drop containing only enough material to deposit a single dot.

The volume of the drop is typically determined by pin cross-section dimensions, shape and surface characteristics of the tip of the pin as well as by the viscosity and surface tension of the fluid to be deposited and the techniques by which the tip is supplied.

By providing the tip of the deposit pin with a sharply defined rim, it is found during repeated action that fluid drops of consistent volume are defined by the tip when all other factors remain constant.

Presently we prefer that the rim of the tip of the pin be "square", i.e. that, in profile, the end surface of the tip of the pin be substantially at a right angle to the side surface of the pin, and that the pin side surfaces be smooth. Preferably the pin is round in transverse cross-section, though it may be of other shapes. Under certain circumstances, as when depositing on porous substrates that readily receive the fluid, the end surface of the pin may also have a surface-tension enhancing surface to optimize the fluid acquisition capability of the pin. For example it may have a roughened surface, surface roughness of at least 1000 microinch, or be composed of high surface energy material, (surface energy greater than 2500 mN/m), such as tungsten.

It is found that arrays of fluid dots between about 20 microns to 375 microns can be deposited using biologic fluids of conventional concentrations, by employing deposit pins that have, in their tip regions, a wire or wire-like geometry of diameter (true diameter or cross-section dimension) between about 0.001 inch (25 microns) and 0.015 inch (375 microns). The smaller tips, i.e. tips smaller than 0.012 inch (300 microns) are referred to here as "microtips". A preferred range of tip sizes is between 50 microns and 250 microns.

In preferred embodiments, at least at the time of engagement of the pin against the receiving surface, precise positioning of the pin is achieved by lateral constraint of the pin to a reference position. The pin is also axially controlled, preferably by a compliant mounting, to limit the maximum deposit force to preferably less than 1 gram, in preferred cases less than 0.5 gram, e.g. 0.3 grams. The lateral constraint ensures that the deposited drop is precisely located while the "soft landing" assists in achieving a well-defined deposit, in protecting the end geometry of the pin to preserve its drop-sizing function over long usage, and in protecting fragile substrates that may define the receiving surface.

With these provisions, tightly packed arrays of deposited dots of fluid can be achieved, i.e. arrays with center-to-center spacing between dots of less than three times the dot diameter, often only twice or one and one half times the dot diameter.

FIG. 1 is a free body diagram of a deposit pin 12 having a microtip that is laterally constrained to a reference position by application of forces (see FIG. 1A). This achieves precise X,Y positioning of the tip at the time of its engagement with the receiving substrate 20. Tip 12d has sharp rim 12f, and is round in cross-section, of diameter d in the range greater than about 15 microns and less than about 375 microns, preferably less than 300 microns, preferably in the range between about 15 or 50 microns and 250 microns. It is capable of defining and depositing upon substrates micro dots of fluid of generally corresponding dimension in the tightly packed arrays.

In the embodiment of FIGS. 1 and 1A the deposit pin is carried on support 17. The pin, though laterally constrained at the time of engagement with the substrate, is mounted to be axially compliant, free to be displaced upwardly relative to the support when the pin encounters the substrate. When the support is lifted from the substrate the pin is free to return to its seat. The pressure applied to the substrate by the pin can be determined by the weight of the pin alone, or as supplemented by a spring or added weight. Preferably the pins are secured against rotation to ensure repeatability of position despite possible variations in shape of the pin due to manufacturing tolerances.

The details of preferred laterally referenced pins axially displaceable from their support are described later with reference also to FIGS. 1B to 1F and to FIGS. 2–2B, FIG. 2' and FIGS. 3–3B. With the mountings shown, the movements occur accurately over a wide range of ambient conditions.

Figure 4A:
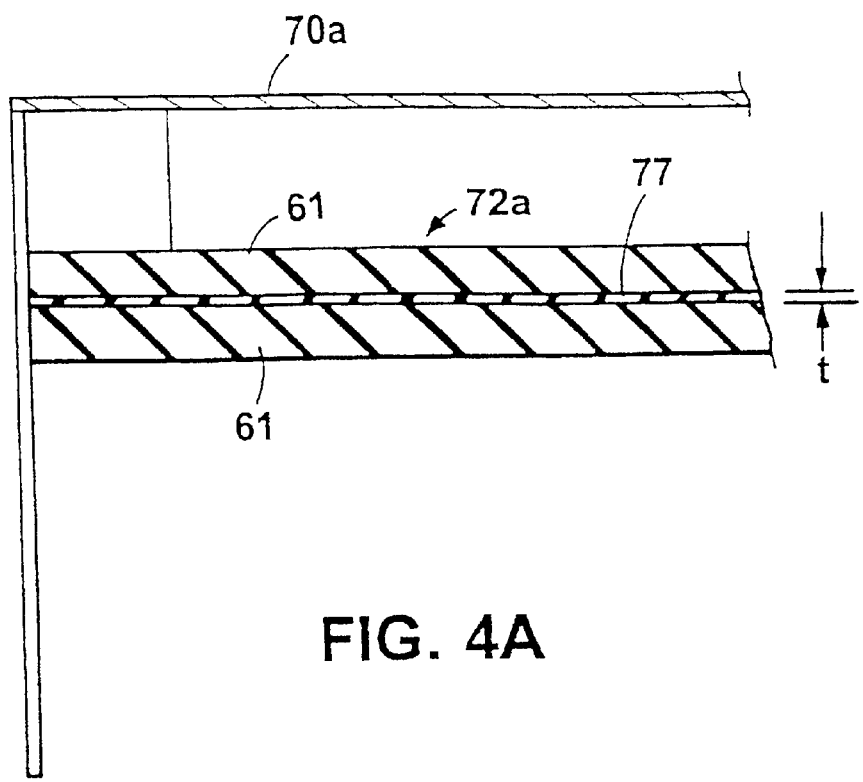
FIGS. 4A and 4B are partial cross-sectional views of other deposit pin mounting constructions employing pairs of spring flexures.
Figure 4B:
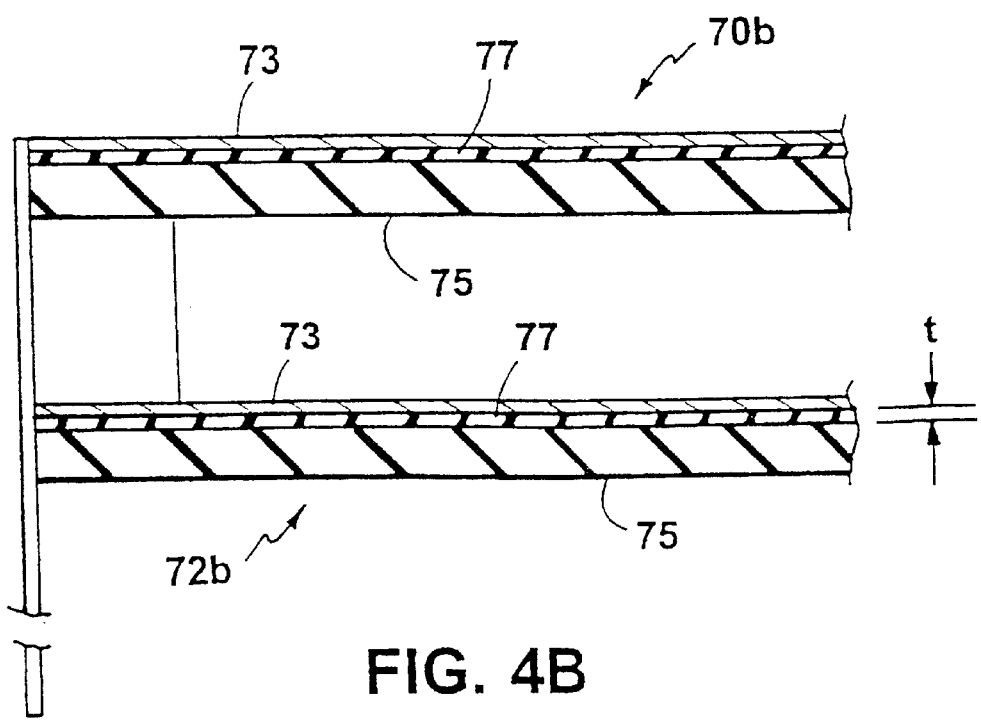

Another laterally referenced pin mounting arrangement is shown in FIG. 4, see also FIGS. 4A and 4B. Pin 12 is supported by a pair of spaced apart, parallel, planar, cantilevered flexures 70, 72 that extend perpendicular to the direction of the desired compliant motion of the pin, to provide a parallelogram type of mounting that laterally constrains the pin to a reference position to enable landing of the pin at a precise location on the substrate. A soft landing occurs due to compliance provided by the flexures. To deposit precise arrays of dots as small as 25 micron (0.001 inch) diameter, an element of spring metal in at least one of the flexures 70, 72 ensures that the deposit pin returns to its original vertical position after each deposit.

Provision of a suitable mounting and drive of the deposit pin, as illustrated in the FIGS. 1–4, enables a low and predictable contact force upon the receiving substrate (the "soft landing") despite variations in the height of the substrate, e.g. due to variations in thickness of microscope slides or slide-like members upon which the fluid dots are applied. Superior results can be obtained by controlling the deposit pin force upon the substrate to less than the order of one gram, or 0.5 gram, preferably about 0.3 gram.

While vertical reciprocation of a deposit pin is presently preferred, other motions can be employed.

The deposition systems described have long-term dimensional stability, being immune from temperature, humidity and other ambient changes. The systems enable spotting of, e.g., a full set of 40 microscope slides with 10,000 spots per slide, a process that may require a few hours to a few weeks, depending upon the number of pins operating simultaneously in one head. The instrument may operate unattended for many hours at a time.

For high speed operation, the system also preferably has a natural resonant frequency higher than 10 Hz, e.g., 20 Hz, which is achieved by employing a pin of low mass and a suitable support.

To operate at high speed, e.g. such as a drop formation/drop deposit cycle of 0.1 second, in addition to having a natural frequency higher than 10 Hz or 20 Hz, the pin mounting system has a provision for damping the motion of the moving pin element, preferably by an amount close to critical damping. This damping prevents the pin from bouncing and degrading the spotting process and enables the pin to be moved quickly away after each deposit action. In preferred embodiments, damping is obtained concurrently with providing very high compliance of the pin support. The general principle of combined compliance and damping is illustrated in FIG. 1G. The actuator A acts through a highly compliant support spring Z, buffered by a damping device X, the moving assembly having a natural frequency in excess of 10 Hz. Where sliding action of weighted pins is employed, friction of the sliding surfaces can be employed to provide damping.

In embodiments that employ cylindrical deposit pins moving axially normal to the deposit surface, with spring mounting systems in which the weight of the pin is insignificant or counter balanced, it is observed that a spring support system for the pin with stiffness of less than 5 gram per millimeter deflection, measured at the pin, produces good results for cases in which the amount of pin deflection is a few tenths of one millimeter. In one particular case, a spring system having a spring deflection ratio of 3 gram/mm, deflected about 0.2 mm, resulted in deposition of dots of fluid of excellent, repeatable quality over a range of microscope slides.

Use of the deposit pins to deposit biological fluid or reagent on a rigid substrate is illustrated in the sequence of highly magnified, diagrammatic FIGS. 5A–5E while FIGS. 5F–5I illustrate use of the pins to deposit fluid dots upon a delicate, soft or porous membrane and the like.

In FIG. 5A, the deposit pin P is seen supporting a drop F of fluid obtained e.g. from a mobile sub-reservoir MW (FIG. 1) or sub-reservoir ring 14, (FIGS. 1, 4). The pin moves under control of driver D toward a selected target point S on receiving surface R. In the case of dipping into sub-reservoir MW, surface tension effects hold fluid drop F in substantially semi-spherical form on the sharp-rimmed tip of the pin, see FIG. 7. When the tip is plunged through fluid held in sub-reservoir ring 14, the drop F is normally shallower, less rounded, see FIG. 9. Surface R, when a microscope slide, is typically impermeable and non-wettable such as silene-coated glass.

In FIG. 5B, the pin has advanced sufficiently toward the receiving surface R that contact of the fluid drop with the surface has occurred. The drop has been forced to distort to a generally cylindrical shape, C.

In FIG. 5C, the pin P has advanced toward surface R to level L. The fluid cylinder $C_1$ is of expanded form, in which its boundary has been stretched, but it remains as a coherent fluid mass between and in the immediate vicinity of the receiving surface and the tip of pin P. The system for driving the pin limits the further movement of the pin toward the receiving surface R in the manner that the maximum force exerted by the pin upon the substrate is limited, as described.

In preferred mechanical systems, the pin is compliantly mounted and responds to resistance force transmitted to the pin by the fluid or mechanical contact with the substrate, so that the tip of the pin stops despite overtravel of the driver.

In other systems, based upon position detection, the driver is stopped in response to a position sensor at the desired level. In hybrid systems, combinations of compliant or mechanical limiting systems and positional detection can be employed.

In FIG. 5C the fluid cylinder $C_1$, is shown expanded relative to its base in FIG. 5B. The degree of expansion and the curvature of the fluid wall is determined by the degree of wettability of surface R and the surface tension characteristics of the fluid, as well as by the force applied by the pin.

In FIG. 5D, the pin P has moved away from surface R, leaving drop DF at target point S. The drop DF may contract in base diameter. The degree of such contraction or of expansion is determined by the wettability of the receiving surface and surface tension characteristics of the fluid. When surface R is hydrophobic, the deposited fluid drop may contract as it dries, while with wettable, fibrous, or porous surfaces, it may expand; in either event, the size of the deposited dot is determined principally by the size of the tip of pin 12.

In FIG. 5E the pin P, substantially devoid of fluid, moves away from receiving surface R, with a component of lateral movement, M. It is rapidly resupplied and proceeds to the next target point. The pin P is resupplied in important cases from a mobile local sub-reservoir that accompanies the pin across the substrate, e.g. the movable reservoir MW of FIG. 1 or the annular supply ring 14 of FIG. 1 or FIG. 4. The deposit cycle is then repeated at another lateral (X,Y) position to which the pin is moved.

Instead of placing deposits on a rigid, smooth substrate, the substrate may be a porous or microporous membrane or a delicate film such as nitrocellulose, cellulose acetate, polyvinylidine fluoride (PVDF) or nylon, or it may be an agar gel or other gel. The particular substrate can be selected in accordance with the nucleic acid, protein or other transfer procedure being employed, and can be the same as or take into consideration the substrates previously used in development of historical reference data with which the results of the present experiment are to be compared. The compliance of the pin protects such fragile substrates from damage.

Action of a deposit pin in depositing biological fluid or reagent on a delicate, soft or porous substrate is illustrated in highly magnified FIGS. 5F–5I. A delicate, relatively soft membrane $D_M$ is supported directly on a rigid support $R_S$.

Figure 5F:
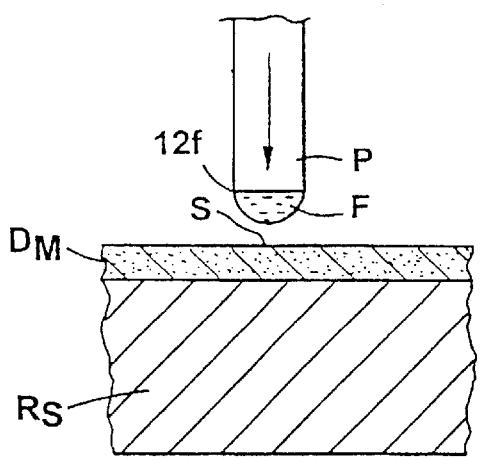

In FIG. 5F, as in FIG. 5A, the tip of deposit pin P having a sharp rim 12$f$ supports a precisely sized drop F of fluid specimen or reagent obtained from a mobile sub-reservoir, and moves toward a preselected deposition point S.

Figure 5G:
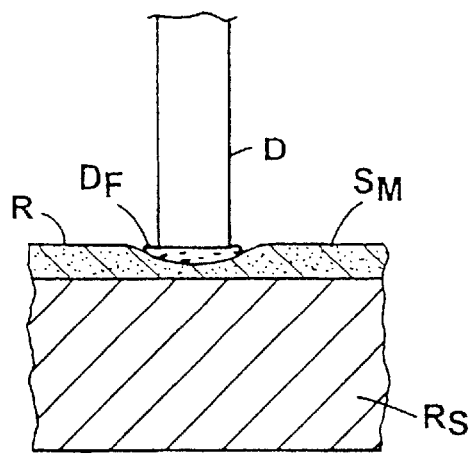

In FIG. 5G, the pin has advanced sufficiently toward the receiving surface R that the fluid drop contacts the surface. The slight pressure of pin P slightly deforms membrane $S_M$ as illustrated in FIG. 5G, but axial compliance of the pin prevents damage to the relatively soft substrate. Depending upon the porosity or softness of the membrane and any capillarity, the fluid may migrate slightly to the sides, but the size of the deposited dot of fluid is principally determined by the size of the pin's tip.

In other cases, a protective buffer member, not shown, which may be soft or resilient may be interposed between deposit pin and substrate. In some cases where the buffer member is significantly compliant, compliance of the deposit pin itself may be omitted in those conditions where a degree of compliance is required.

Figure 5H:
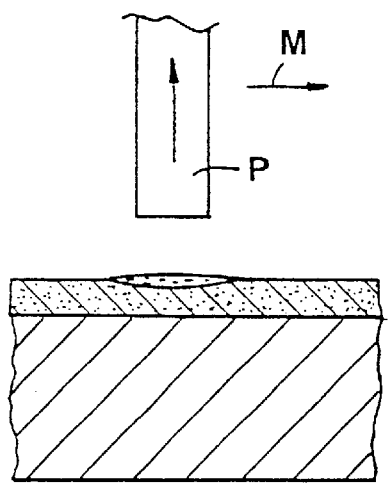

In FIG. 5H the pin P, substantially devoid of fluid, moves away from the receiving surface with a component M of lateral movement, and proceeds to the next target point. Because of the light contact pressure, the shape of the tip and the presence of the intervening fluid, no particles of the substrate remain on the tip. Upon relief of the slight deposit pressure, the membrane begins to recover its original conformation.

Figure 5I:
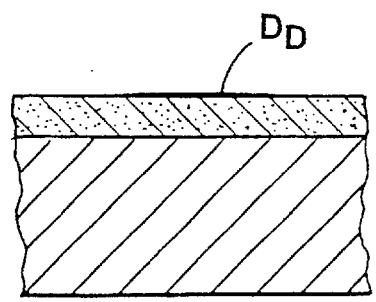

In a short while, as shown in FIG. 5I, the delicate membrane substantially recovers its conformation and the fluid has dried, leaving dried deposit $D_D$ of substantially the size of the tip of the deposit pin.

Figure 5J:
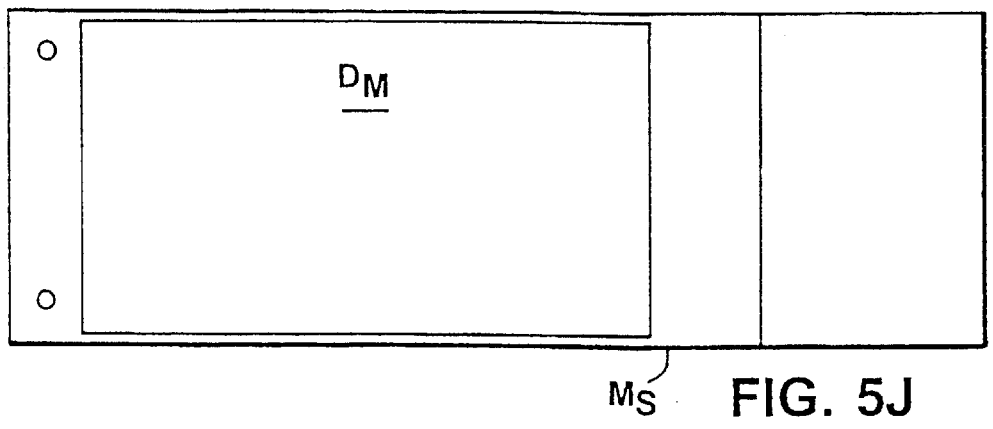
FIG. 5J shows a rigid slide carrying a membrane upon which an array of dots can be deposited.

FIG. 5J depicts a glass microscope slide or slide-like member $M_S$ carrying a delicate membrane, $D_M$, e.g. a thin layer of microporous nitrocellulose film formed by casting, such as is available from Grace Bio-Labs Inc. under the trademark Oncyte® Film Slides. The process just described may be employed to deposit microarrays of fluids on such microporous film. Although the deposit-receiving surface is not rigid itself, by virtue of a rigid backing, the delicate membrane can be automatically processed, scanned, etc. by available robotic equipment that engage the rigid frame.

High density arrays of individual deposited dots as depicted in FIGS. 5A–5D and 5F–5I are achieved by repeated deposit action of one or more deposit pins, with selected fluids being deposited at selected precise locations under computer control as further described below.

FIGS. 5K–5N depict diagrammatically, in magnified scale, the depositing of one deposit upon another in a precisely aligned manner, made possible by the positional accuracy of the systems being described. FIG. 5K shows a deposit 100, as produced by techniques previously described employing a deposit pin, or by some other technique that achieves a known position. FIG. 5L shows deposit pin 12 having been indexed into precise alignment with dot 100, and lowered to engage fluid drop $C_1$ with it. FIG. 5M shows the deposited second drop 104 still in fluid state while FIG. 5N shows dried second dot 106 deposited upon dot 100.

In similar fashion FIGS. 5O–5R illustrate deposit of a relatively large spot of fluid using large deposit pin 120 and subsequent deposit of small drops using a smaller deposit pin 12 having a microtip. The large drop on the pin 120, in FIG. 5O, forms a large deposited drop 110, FIG. 5P, which dries to form a large dried spot 112, FIG. 5Q. Subsequently, small drops 114 are deposited in selected precise locations upon the large spot 112, FIG. 5R, which can be identified to computer memory and employed at the time of microscopic examination to correlate the results.

FIGS. 5S–5V illustrate the possibility, with selected receiving substrates and fluids, of conducting the operation of FIGS. 5K–5N in inverted fashion. Similarly the other deposit actions described may also be performed with inverted motions, or at other angles.

Referring to FIG. 6, a deposit device comprising deposit pin 12 and sub-reservoir ring 14 supported by rod 15, is used to deposit dots of fluid on the flat bottom $F_B$ of a conventional well of a microtiter plate $M_P$. A number of precisely located deposits of fluid $D_F$ can be made, taking advantage of the long length and small diameter of the deposit pin 12, which enables reaching the bottom of the well at precisely spaced locations. For instance, a series of probes may be bound as dots to the bottom of a well at known, recorded positions, a fluid containing the analyte may be used to fill a well, and subsequent to a reaction or incubation interval, the bottom of the well may be scanned by a microscope, or otherwise examined, to determine which deposited probes matched the analyte fluid. By pre-preparation of such a plate with known sets of probes, many fluids or many probe actions with a given fluid may be assessed.

Details of preferred embodiments that laterally constrain the pin to a reference position and facilitate highly accurate X,Y positioning of a microtip during each deposit will now be described.

Referring to FIG. 1, deposit pin 12 comprises a relatively large body 12$a$ and a lower portion 12$b$ of reduced dimension that leads to deposit tip 12$d$ having sharp rim 12$f$. The pin also has an upwardly extending guide portion 12$c$.

Large body 12$a$ provides a downwardly-directed annular surface 12$e$ that is engaged upon a support, to receive support force $F_s$ that bears the pin's weight.

The assembly is constructed to enable a lateral bias force $F_b$ to urge pin 12 against a pair of reference surfaces $Ref_1$ and $Ref_2$ which lie at an angle to each other as viewed in horizontal cross-section, FIG. 1A. These reference surfaces are arranged to resist movement of the pin in X and Y coordinates by applying reaction forces that have X and Y components. The combined X components of the forces provide resistance force $F_r$ that balances bias force $F_b$. The reference surfaces are constructed to leave the pin free to move axially along axis A (Z direction), as by sliding, to provide axial compliance to the tip 12d when the substrate is encountered.

In certain practical embodiments, for mounting the pins, two vertically spaced horizontal plates 9 and 11, shown in dashed lines, are joined to form carrier 17 that moves in X,Y and Z directions for carrying the pin through deposit, cleaning and resupply motions. The upper plate 9 is at a selected distance from the lower plate and applies a constraining force $F_c$ to constrain the angle of the pin, and hence the position of its tip 12d, within selected tolerance.

Lowering carrier 17 causes the precisely positioned tip 12d to engage substrate R, whether the substrate be found at level 20, 20a or 20b in the design range. Upon engagement with the substrate, the pin stops. Further downward movement of the carrier 17 occurs with the compliant pin remaining stationary above its seat, while reverse movement of the carrier causes the pin to reseat on its support. In this way the vertical movement of the carrier need not be controlled with high accuracy, and proper contact with the substrate can occur over a range of tolerances in the height of the substrates.

The lateral bias force $F_b$, for laterally constraining the pin to a reference position, can be applied to deposit pin 12 in numerous ways that permit axial movement of the pin relative to its carrier 17 when the pin encounters the substrate. FIG. 1B illustrates application of lateral bias force by miniature spring-loaded bearings that urge the pin toward an inside corner defined by reference surfaces $Ref_1$ and $Ref_2$, but leave it free to move axially. FIG. 1C illustrates tilting the longitudinal axis A of the pin relative to the vertical, in a manner that the weight of the pin applies to itself a slight turning moment that biases the pin against reference surfaces $Ref_1$ and $Ref_2$ but leaves it free axially.

Other techniques include introducing bias by an eccentric load or by other loading techniques. Magnetic attraction can also be employed to draw the pin to a defined corner or a particular arc of a conical seat, using permanent magnets or electromagnets. Likewise, electrostatic forces can be employed, e.g. by imparting a charge to a region of one of the members relative to the other and employing a dielectric layer to prevent discharge so that the attraction persists at the time of approach of the deposit pin toward the substrate. The vertical effect of such loading techniques can be sufficiently small to be overcome by axial force on the pin, to enable axially compliant motion of the pin.

FIGS. 1D, 1E and 1F show that tangent planes $P_1$ and $P_2$ to a segment of a conical seat (FIG. 1E) against which a pin is urged effectively define two reference surfaces set at an angle to one another, that act in the manner as explained to resist lateral movement of pin 12 in both X and Y directions. The same is true for other surfaces of revolution that define seating surfaces. Preferential seating upon a given segment of the seating surfaces may be achieved by the loading techniques previously described.

FIGS. 2, 2A and 2B, show embodiments that employ a surface of revolution for supporting the pin in a laterally constrained manner.

Fluid deposit pin 12, (associated with a fluid supply such as mobile multiwell plate MW or associated supply ring 14), is constrained between upper and lower plates 9 and 11 of carrier 17. Carrier 17 moves in the direction of arrow Z for supply and deposit actions. In each case of FIGS. 2, 2A and 2B, an enlarged portion of the pin 12a rests normally in a seat 13, 13a or 13b in plate 11 which bears the weight of the pin. The pin is free to be displaced relatively upwardly from its seat, as shown, upon contact of tip 12d with substrate 20.

When the pin 12 rests in its seat, the X,Y position of tip 12d of the pin is defined by the degree of perfection of the pin 12, the relative distance to the upper supporting plate 9, the clearance between upper portion 12c of the guide pin and the guide hole 19 in plate 9, and, as indicated above, a preferred feature in the system that applies a definite (though permissibly slight) lateral bias of the pin to a given side of the engaging structure. For this purpose, in FIG. 2, compression spring 22 is disposed between upper plate 9 and upwardly directed ledge 24 of pin 12. The spring is fixed in position and applies its downward force with slight and predictable asymmetry relative to center axis A, to bias the pin to a given side, to ensure repeatable positioning of the pin on the same region of its seat on plate 11. Spring 22 is sized and arranged to also provide compliant pressure of tip 12d of the pin on the substrate 20, taking into consideration also the mass of the pin.

In the arrangement of FIG. 2', the lower part of spring 24' tightly engages about the pin to secure it rotationally, while an upper leg 22a of the spring extends into a hole in plate 19, to serve as a stop. In this way the rotational position of the pin is secured so that variation in its shape will not introduce variations in position during repeated actions.

The sizing and nature of the spring can be selected to provide a high natural frequency for the system. In the various embodiments thus far described, the pins are axially slidable relative to their supports and friction contact produces a desirable degree of damping of the motion during rapid reciprocation. In other cases, damping material may be associated with the spring or other mounting of the device.

In the arrangements of FIGS. 2A and 2B the pin is also biased laterally, e.g. by use of spring 22 or 22', by angling the long axis of the pin a few degrees from vertical (with the axes of all adjacent pins being parallel when an array of pins is employed), etc.

The pins of FIGS. 2, 2A or 2B in cylindrical form are readily formable to a suitable degree of perfection. The distance D (FIG. 2) is readily selectable, considering that, for a given clearance allowance between the hole of the upper plate and upper pin portion 12c, increase of distance D decreases the possible disturbance of the pin from its nominal orientation due to manufacturing variation, etc. Thus, while the bottom plate 11 of these embodiments defines the vertical level of the tip of the pin 12d, the top plate 9 is located sufficiently above plate 11 that its spacing and the angles produced establish the lateral position of the tip of the pin within desired tolerances for precise deposit of dense arrays on the substrate 20.

It is seen from FIGS. 2, 2A and 2B that the driven pin carrier structure 17 travels downwardly sufficiently to ensure that tip 12d can reach the lowest level 20b of the range of permissible levels. As in previous embodiments, the tip 12d is axially compliant in the sense that the pin can yield in position so that, when encountering the substrate, it exerts only a controlled light pressure on the substrate before it lifts from its seat.

In FIG. 3, the enlarged part 12a' of pin $12^1$ and seat 13c have complementary conical surfaces normally engaged unless the tip 12d' is engaged with the substrate (but shown disengaged for purposes of illustration). The upper end surface 12g of the enlarged body portion 12a' is sloped in a selected direction as explained further below and a rigid ball bearing 38 bears on the sloped surface at a point offset from central axis A. A weight 39 rests upon ball 38, being housed by a bore in spacer block 41 upon which the upper and lower plates 9 and 11 are affixed. The spacer block is advantageously of a low-friction engineering plastic such as Delryn. The weight 39 is of selected size to adjust compliance to the degree desired for the deposit tip 12$d'$ and to apply a slight turning moment $M_o$ to the pin toward a portion of the conical seat, (see FIG. 1), via the eccentrically located ball.

As seen in the cross-section of FIG. 3A, weight 39 is of cylindrical configuration, free to rotate about axis A with turning of the ball to avoid applying undue drag. The main body 12$a'$ of the pin, however, is of square cross-section and is disposed in square channel 42 in spacer block 41 of like configuration. This prevents pin rotation so that orientation of the upper end face 12$g$ and top 12$d'$ remain constant. The slope of surface 12$g$ relative to axis A and the flats of the square section of the pin are cooperatively related to cause engagement with square channel 42. This is accomplished by sloping surface 12$g$ toward a corner of the square channel. Thus deposit tip 12$d'$ resides at a constant, precisely defined lateral position by cooperation of eccentric weight 39, the segment of the conical seat against which the pin is urged by the weight, and by the prevention of pin rotation. By use of a selected weight (instead of a spring), the spotting force upon the substrate is constant over the range of possible heights of the receiving substrate, which can enhance repeatability of spot size over that range.

Such lateral arrangements are important when employing microtips in arrays that require precise positioning such as high density arrays.

The features previously discussed, i.e. lateral reference of the pin, axial compliance, stability, high natural frequency, and damping can also be simultaneously achieved by flexure mounting of the deposit pin as shown in FIG. 4A. Two similar and highly compliant planar flexures 70$a$, 72$a$ have similar elasticity, but one of them, flexure 70$a$, is made of a highly stable material, e.g. metal spring, while the other flexure, 72$a$, provides good damping properties.

The stable flexure 70$a$ is preferably manufactured by photo etching a thin metal sheet, such as 0.002-inch thick stainless steel, which exhibits high stability and low rigidity but has poor damping properties. The other flexure 72$a$, preferably equally compliant, is provided with desired damping properties, and is less stable. The second flexure 72$a$, for instance, is constructed as a bonded sandwich of two identical photo-etched thin plastic sheets 61 such as 0.005 inch thick polyamide resin, e.g. Kapton® from dupont. An energy absorbent bonding agent, e.g., of thickness t of 0.002" provides a damping layer 77 between these resin sheets. The bonding agent may be a thin coat of rubber cement such as available from 3M as ID #62-60065-4826-1 or 3M double sided tape #927.

In an alternate construction shown in FIG. 4B, flexures 70$b$, 72$b$ are identical, each being a sandwich of one metal layer 73 and one resin layer 75 bonded together by rubber damping layer 77. Compliance similar to that of FIG. 4A is achievable with the selection of material of appropriate thickness, such as either a stainless steel layer 0.0016 inch thick or a copper-beryllium layer 0.0022 inch thick, bonded by the damping layer to a polyamide layer 0.005 inch thick.

The physical properties of the flexures can also be tailored to the particular need by change in geometry of the flexures. An example is the provision of cutouts.

In manufacture, a large-area bonded sandwich of all three materials may be fabricated and the shape of the flexures can then be produced by photo etching the desired outline and any cutouts.

Figure 24:
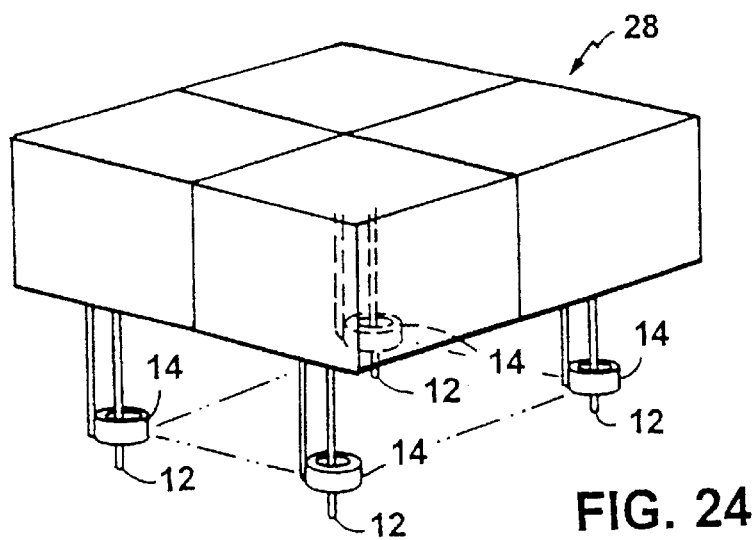
FIG. 24 shows a ganged deposit system having four independently operable deposit pins.
Figure 24C:
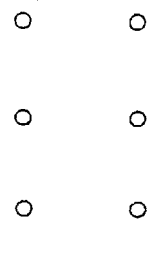
FIG. 24C is a plan view of an array of dots producible by the system of FIGS. 24A and 24B.
Figure 24B:
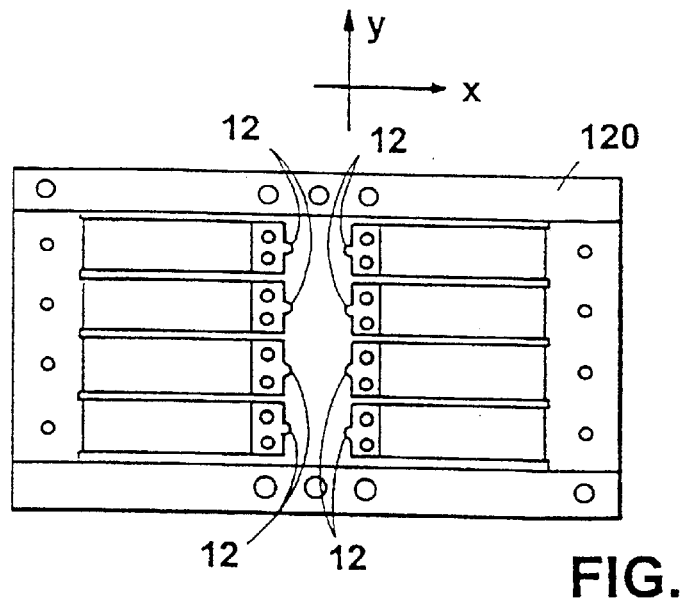
FIG. 24A is a partial perspective view and FIG. 24B is a plan view of a ganged deposit system having a number of flexure-mounted deposit pins driven by a single driver and a corresponding number of sub-reservoir rings driven by a single driver.
Figure 24A:
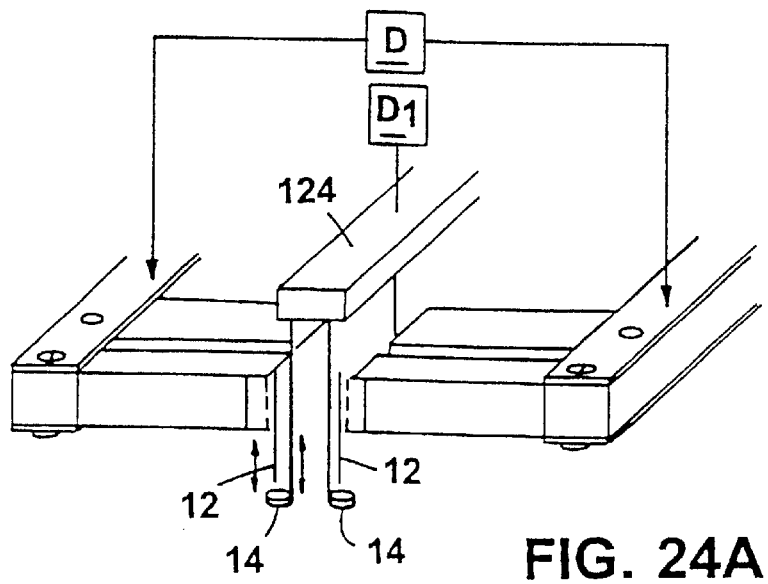

In a cluster of deposit pin assemblies of the type shown in FIGS. 4, 4A and 4B, such as shown in FIGS. 24A and B described below, with 9 mm spacing of pins to correspond with the spacing of wells in a 96 well plate, the flexure elements are preferably 8 mm wide and 22 mm in length, and two or more of the pin and flexure assemblies are mounted in parallel, side by side, at 9 mm pin spacings. Preferably two sets of such assemblies, disposed head-to-head as described below, are employed at 9 mm pin-to-pin spacings, so that an X,Y array of pins is achieved.

B. Mobile Fluid Reservoirs and Interaction with Deposit Pins

For making a succession of deposits of the same fluid, as when preparing a number of microscope slides or membranes or providing redundant deposits on a single substrate, a mobile sub-reservoir, periodically re-supplied from a stationary central supply, travels with a deposit device to be near the deposit locations.

Figure 7:
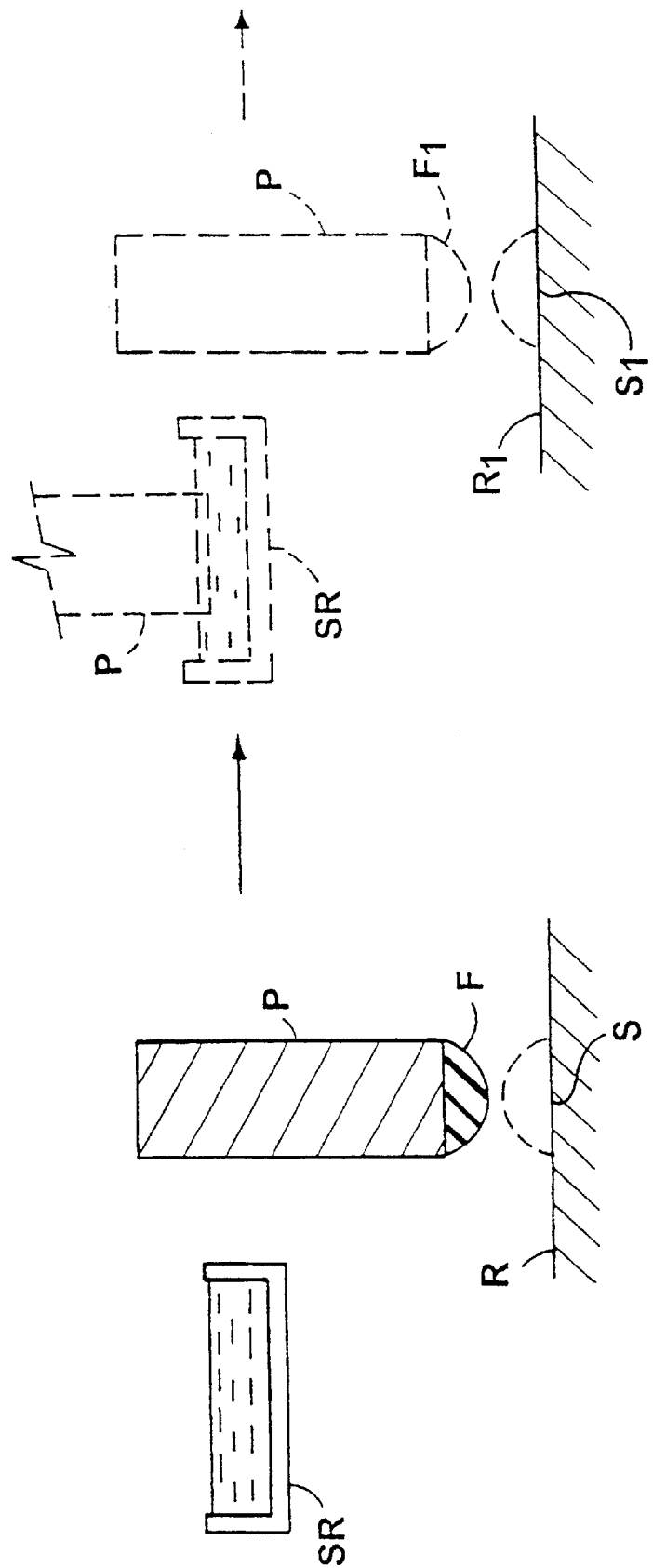
FIG. 7 depicts a mobile sub-reservoir that travels from one deposit position to another with a separate deposit device illustrated as a deposit pin.

As illustrated in FIG. 7, a deposit head comprises the deposit pin P of FIGS. 1 or 4, and the sub-reservoir SR which is sized to contain sufficient sample to enable deposit of a number of dots before being resupplied.

After deposit of drop F at target S, e.g. on a microscope plate R or a plate carrying a delicate or soft membrane, the assembly proceeds to plate $R_1$, pin P is resupplied with drop $F_1$ by being dipped into and raised from the accompanying sub-reservoir SR, the new drop is then deposited at target point $S_1$ at plate $R_1$, and so on.

Figure 8:
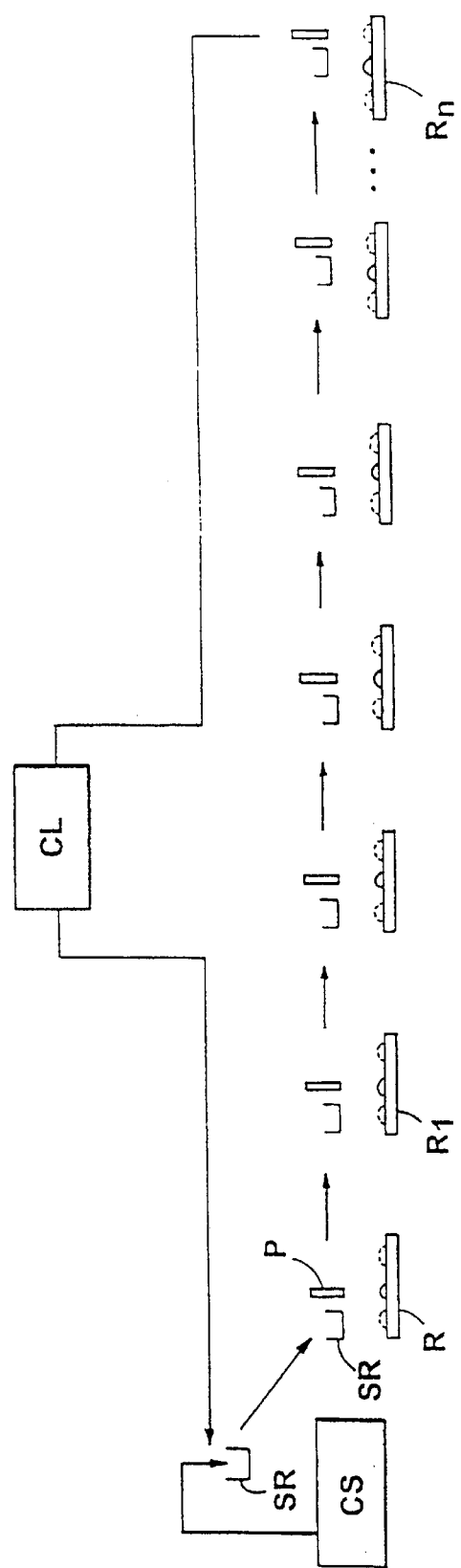
FIG. 8 depicts a system employing the action depicted in FIG. 7, combined with a cleaning station and a central supply of fluid specimen.

The system is especially useful for preparing a number of microscope slides or membranes as illustrated in FIG. 8. The central fluid supply CS advantageously is a multiple well plate as conventionally used in microbiology, such as a 96 well plate. Cleaning and drying stations CL are also provided. The deposit sequence includes moving the assembly of deposit device and mobile sub-reservoir under computer control through cleaning and drying stations CL, thence to central supply CS at which the sub reservoir SR is supplied with a selected fluid sample, e.g. from a selected well of a 96 well plate. Then the group moves over a series of receiving surfaces $R-R_n$, for deposit of fluid dots at selected locations on each, also under computer control. This sequence is repeated a number of times, with controlled selection of different fluid samples (from, e.g., different wells of the central supply CS) for respectively different locations on the plates R or other receiving surfaces. Data that correlates locations with respective specimens is recorded in memory and used in subsequent scanning or reading.

The technique of using a deposit tool that accurately sizes each individual drop, such as the deposit pin with square rim profile at its microtip, combined with a mobile local sub-reservoir that accompanies the tool and carries a volume sufficient to supply a sequence of deposits, has a number of important advantages. The technique, based on small motions, saves time in avoiding repeated travel to a central supply; it avoids evaporation losses of long travel, so that the drop created can be very small and the deposited array very dense; and the dots can be kept consistent in size and concentration or biological content across the array of dots being deposited. The time overhead involved in cleaning, transporting and picking up the specimen is kept small so that, overall, deposits can be made very fast, inexpensively and of desired small size.

In this way a large number (for instance ten to one hundred) identical microscope slides or membranes can readily be prepared by repeated motions over an array of the slides or membranes. Each substrate can carry dots of many different fluids based upon resupply of the sub-reservoir from different wells of a number of multiple well plates introduced to the system.

The sub-reservoir and the deposition device are decoupled, in being movable relatively to one another for resupply and for deposit, as well as being coupled or at least coordinated, to move laterally over the receiving surface to produce the series of deposits. The sub-reservoir can move into a resupply position, e.g. by immersion into a well, or under a suitable pipette. It can be made to hold sufficient fluid in excess of that required for the sequence of deposits, or to expose a sufficiently limited evaporative area, that concentration of the substance of interest in the fluid is not substantially affected by evaporation during the multiple deposit sequence.

Thus we have described deposit devices constructed to precisely define a single fluid drop of desired size, obtained from a mobile sub-reservoir, deposit the drop at a precisely positioned, discrete location and return by local movement to the sub-reservoir for another drop. In the preferred embodiment of FIGS. 7 and 8 an axially reciprocable deposit pin, as illustrated in FIG. 1, is employed for this purpose in conjunction with an accompanying sub-reservoir in which the pin is directly dipped. Alternatively, a probe that dips into a local sub-reservoir as by coordinated rotational or translational motions of a wire or pin, can accomplish this action, as can other designs.

Figure 10:
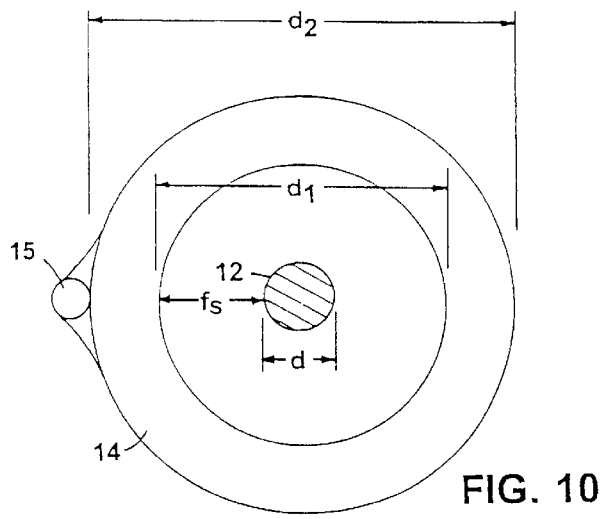
Figure 9:
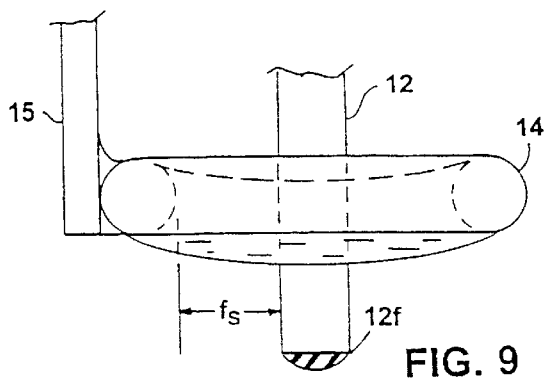

Referring now to FIGS. 9 and 10, another preferred mobile sub-reservoir is an annular ring 14 which, as depicted, holds fluid between its interior opposed surfaces by surface tension effects.

Deposit pin 12, having a sharp rim 12f at its tip, of diameter d selected to produce the desired size of the deposited dot, is mounted in axi-symmetric relation to sub-reservoir ring 14. Ring 14 has an internal diameter $d_1$ significantly larger than the pin diameter such that fluid space fs exists between the pin and the inner surfaces of the ring. As shown in FIGS. 9E and 10, the outer diameter $d_2$ of ring 14 is sized smaller than the well 19 of a central supply plate, 21, so that the ring can be immersed in it for supply.

Figure 9A:
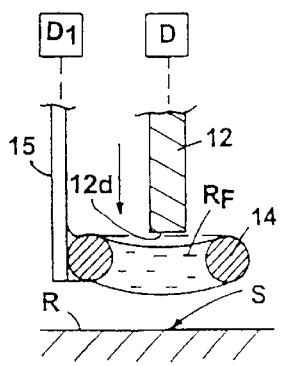
FIGS. 9A–9D depict a sequence of stages of the deposit action of the head of FIG. 9.
Figure 9B:
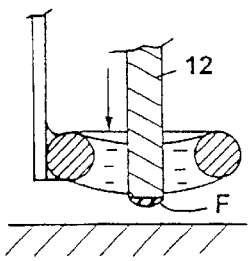
Figure 9C:
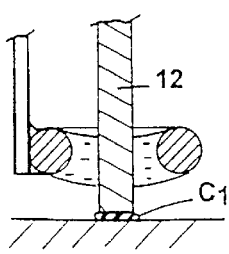
Figure 9D:
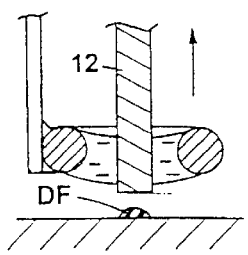

During the deposit sequence of FIGS. 9A–9D the ring 14 is held stationary by its support rod 15 while the deposit pin 12 is moved by an associated driver D through a sequence of vertical positions. In the start position, the end 12d of pin 12 is drawn above the lower surface of the retained fluid $R_f$ held by surface tension effects between the internal surfaces of ring 14. This is shown in FIG. 9A. (The pin, for illustration, is shown withdrawn fully above the retained fluid $R_f$, although that is not necessary.)

Comparing FIG. 9A with FIG. 9, by downward movement of the pin tip from above the lower surface of the retained fluid $R_f$ (FIG. 9A), to below that surface (FIG. 9), the tip of the pin, with its sharply defined rim, picks up from the retained fluid $R_F$ a precisely sized volume of fluid as drop F. The drop is then deposited in the sequence shown in FIGS. 9C and 9D.

At the resupply position of FIG. 9E, the annular ring 14 is moved downwardly by its support rod 15 for immersion in the well of the supply plate while the pin 12 remains stationary at a higher elevation, FIG. 9E, or it may assist in the resupply action, see FIG. 9L, described below. The ring is moved by associated driver $D_1$, FIG. 9A.

Figure 9G:
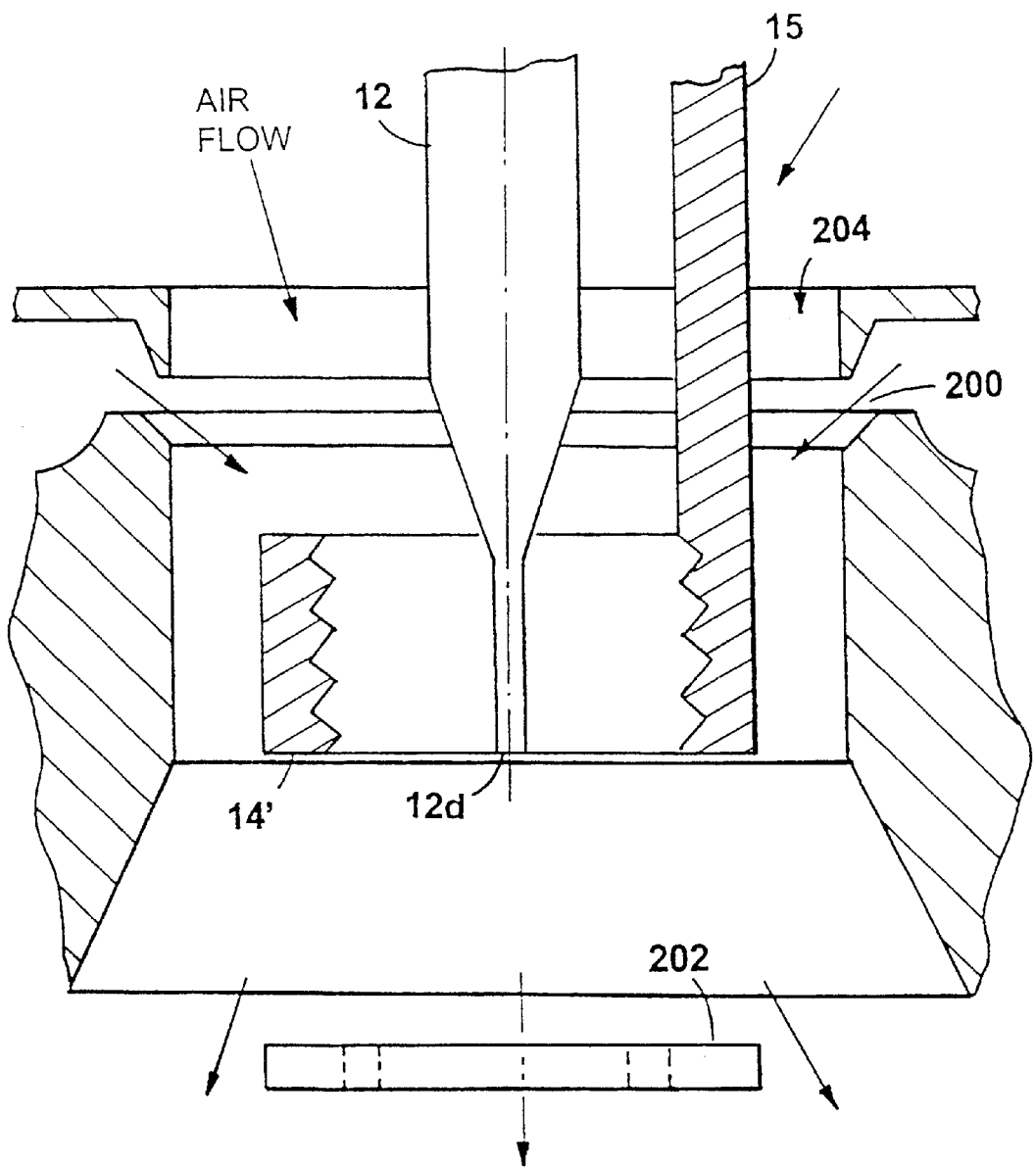
FIG. 9G depicts a station for removing liquid, washing and drying the pin and ring.

At cleaning and drying stations, FIGS. 9F and 9G, the lower surfaces of the pin 12 and ring 14' are shown vertically aligned (the ring here shown as a cylindrical ring).

At washing station, FIG. 9F, the ring and pin may both be subjected to reciprocation in the vat of cleaning solution in the same or opposite vertical directions to assist the cleaning process. The wash station may be an ultrasonic bath.

The multipurpose station illustrated in FIG. 9G is sized to receive deposit pin 12 and supply ring 14. It has an annular nozzle 200 directed inwardly against the pin and ring to subject the parts to a conical flow from fluid sources such as compressed air, pressurized liquid and aerosols. The flow is directed past the parts 12, 14 to a trap having disposable filter 202 that intercepts material being removed from the parts. The trap may be associated with a vacuum pump. As shown, nozzle 200 is associated with a secondary air path 204 to enable nozzle flow to induce a flow of secondary air when desired.

The system of FIG. 9G is useful to remove sample liquid from the parts, to effect cleaning, and to dry the parts. For example the pin and ring are first exposed to one or more simultaneous or successive fluid currents or blasts of continuous or pulsed flow that blow remaining sample fluid from the parts and into the trap. Subsequently, a fluid stream of liquid or air may expose the parts to cleaning fluids such as liquid streams or aerosols containing water-borne detergent. This is followed by rinsing with pure water from the nozzle. Following washing, an air current from the nozzle, supplemented by induced air flow 204, can dry both pin and ring, in which case the air streams may be heated.

Supply from wells of 96 well plates, for deposit of the restricted amounts of fluid that result from PCR (polymerase chain reaction) present a particular problem. Referring to FIG. 9H, wells 100 are made to hold extremely small volumes of fluid, typically 2 to 10 micro liter (1 micro liter=1 cubic mm). These wells are typically coneshaped with the top diameter about 6 mm and the bottom shaped as a semisphere about 2 mm in diameter. Liquids, even of low viscosity, for instance water, are so held by surface tension in such a well that volumes up to 15 micro liter can be held against gravity when the plate is inverted. Smaller amounts of such liquids to supply a sub-reservoir ring are difficult to extract from the narrow wells due to the aggregate effects of surface tension, gravity, inertia and vacuum.

For removing liquid from such wells a supply ring 14 is provided with a special fluid retentive surface. One example is the provision of internal surface roughness of at least 1000 micro inch. This causes the central region of the ring effectively to have superior hydrophilic properties, i.e. a better "grip" on the fluid by surface tension effects. This permits the uplift of a suitable volume of fluid from a container of approximately mating shape. The exterior surface of the ring may also be provided with a fluid retentive surface to supplement surface-tension effects of the ring, to compete with the retentive properties of the well.

Surface roughness of the internal or exterior surface can be obtained by sanding, broaching or by machining the part on a lathe with a tool or a tap. The ring can also be manufactured from suitably coarse particulate material that is sintered or molded with a binder. Likewise a durable coating can be applied such as formed by carbide particles.

As shown in FIG. 9I, in one preferred embodiment, a cylindrical ring 14A of stainless steel has a height h of 0.050 inch, an inner diameter of 0.060 inches and an outer diameter D of 0.080 inch. It is tapped by a tool having 80 threads per inch, that produces a thread height d and pitch p of 0.012 inch, (the internal diameter is much larger than the diameter of the deposit pin P with which it is used). As shown in FIG. 9H, an annular ring provided with surface roughness in this way is effective to pick up liquid from the conical well of a PCR plate. Despite the desired surface tension effects produced by the internal ring surface, it has smooth surface increments that promote good cleaning.

Also shown in FIGS. 9I and 9J is support rod 15 e.g., of 0.15 inch diameter stainless steel wire, soldered or spot welded at 104a to the exterior of the ring. It drives the ring in its motions, and provides lateral and axial compliance for adapting to any misalignment entering a narrow well.

Figure 9L:
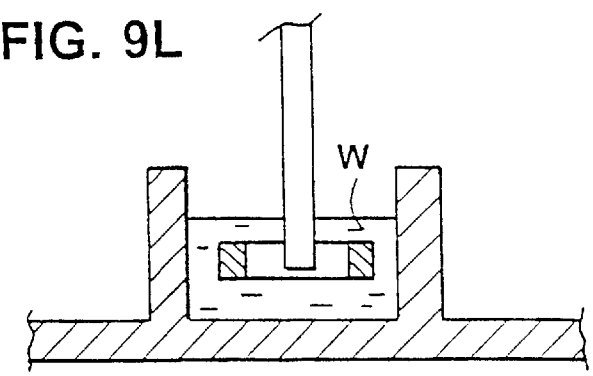
FIG. 9L illustrates on a less magnified scale the immersion of the assembly for pickup of a local fluid supply and FIG. 9M, similar to FIG. 9K, illustrates the fluid load that is picked up by the assembly.
Figure 9K:
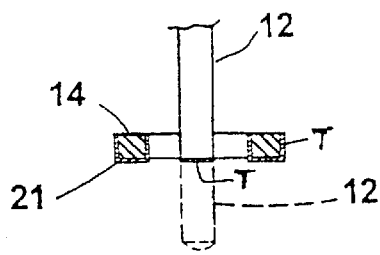

In FIG. 9K is shown a form of pin and ring assembly in which fluid contacting surfaces of both ring 14 and pin 12 are defined by a special substance 21 having a surface energy in excess of 2500 millinewton per meter mN/m), preferably provided by tungsten layers T.

Figure 9M:
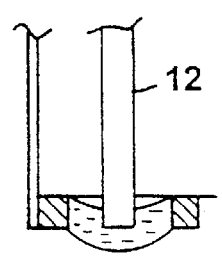

FIGS. 9K and 9L show an advantageous relationship of pin and ring for resupply of the ring. When the ring is immersed in selected well W of a multiwell plate, the pin is present within the confines of the ring, to help the ring pick up the fluid. Their surface tension properties effectively cooperate to compete with the surface tension effects of the walls of the well that resist removal of small quantities of the fluid. In the presently preferred relationship, the bottom tip surface of the pin is substantially aligned with the lower surface of the ring. Withdrawal of the assembly from immersion in well W withdraws a desired amount of fluid, pendent as a large meniscal drop, bounded by the pick up ring, FIG. 9M. This quantity, protected and supported by the ring, is then available for deposit in tiny drops by repeated projection of the pin through the ring, see dotted lines, FIG. 9K.

The sub-reservoir ring may have various advantageous forms such as axially adjacent circular rings, multi-turn helical shapes, closed cylinders, open rectangular rings, open "U" shaped structures, etc. Thus the term "ring" or "annular ring" as used generally refers to any closed or partially closed structure that, through surface tension effects between adjacent or opposed surfaces, supports a volume of liquid in a space through which a deposit device such as deposit pin 12 can operate. The size of the opening or bore of the ring, as well as the size, for instance, of wire or ribbon that forms the cross-sectional shape of the ring is selected in relation to the properties of the fluid (e.g. viscosity and surface tension), the number of deposits to be made from a given fluid charge in the reservoir ring, and the size of the deposit pin that is to move through the ring.

The size and shape of the deposit pins that cooperate with these and other sub-reservoirs also vary depending upon the application. It is possible to employ pins of various transverse cross-section, e.g. square or hexagonal or even rectangular or oval cross-section of equivalent area to round cross-section pins. Especially for small dots, the pins may advantageously have stepped transverse cross-sections, e.g. may have an extremely small cross-section at the deposit end, to size the deposited drop, stepped to a larger cross-section in the main body, for providing structural stability. An example is shown in FIG. 2B.

For implementing the broad concept of a local, mobile supply, other techniques than those shown can be employed. An example is a large dip rod, an enlarged version of a deposit pin, from which a large drop depends, which travels with the pin and is visited by the pin by a suitable motion, such as rotation.

C. Operating Systems

Some advantageous, novel operating systems that implement the foregoing principles will now be described.

Dip & Dot System

The mobile reservoir MW shown in FIG. 1 is shown multi-celled, to represent a multi-well plate. Under computer control, an appropriate X,Y stage brings the chosen fluid resupply well in alignment under the pin. The pin is then controlled to descend, make contact with (dip into) the reservoir fluid and rise, taking a small amount of fluid in the form of a pendant drop.

The pin is raised sufficiently to permit the pin and reservoir to separate e.g. by computer controlled sideways movement of the reservoir, freeing the pin to descend unobstructed to deposit its small fluid drop on the targeted location on the substrate.

With appropriate transport motions of pin and multiwell supply, the process is repeatable at each location where a sample of the selected fluid is desired, the fluid in the proper well being repeatedly brought into alignment with the proper pin for resupply and deposit in the desired location by computer control. Each time a pin is commanded to receive a fluid from a well different from that of its previous command, the pin is moved by computer control to a liquid removal, cleaning and drying station, to prevent contamination.

For efficient operation, a multiplicity of pins may be used, see e.g. FIG. 24, at spacings that match the pattern of wells, enabling each pin to reach inside a separate well of the multiple well reservoir such as a 96 well plate or a 384 well plate, as are known in the field of biochemistry and analytics.

Figure 11:
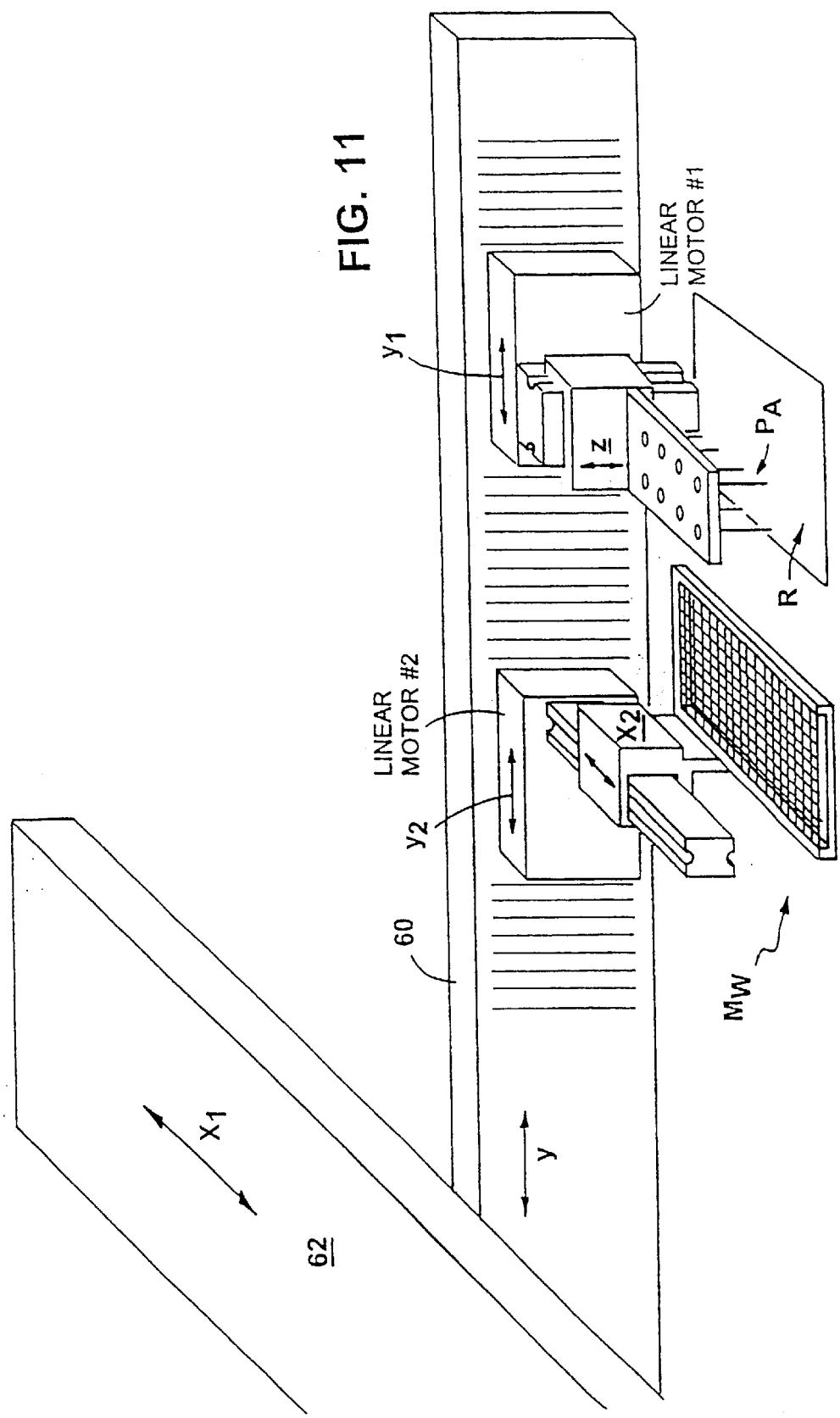

The pin assembly and its driving mechanisms are preferably mounted on a precision XY gantry as they require good positional accuracy. The multiple well plate may be provided with two degrees of freedom in a plane parallel to the deposition plane and can be indexed under the pin assembly on a separate structure. Because of the relatively large size of the wells, the translation assembly for the plate may have lower positional accuracy than that of the pin. In the embodiment of FIGS. 11 and 11A, however, the multi-pin assembly $P_A$ and the mobile multiwell reservoir MW share the same X,Y gantry to advantage.

Rail support 60 of FIG. 11, constructed e.g. to support linear motor movement in the Y coordinate is mounted on an X stage 62, motor not shown. As shown, Y direction linear motors #1 and #2 respectively drive the pin assembly $P_A$ and the multiwell reservoir MW in the Y direction. The reservoir has a secondary linear motor $X_2$ driven by a further driver for X movement of the reservoir relative to the pin assembly. The pin assembly also has Z freedom of controlled movement, driven by a further driver Z.

Under computer control, the multiwell reservoir separates in the Y direction from the pin assembly as shown in FIG. 11, and the Z stage is actuated to cause the pins to form deposits upon substrate R. Then, FIG. 11A, the multiwell reservoir moves under the raised pins into appropriate alignment, employing both $Y_2$ and $X_2$ motions under computer control. By Z motion the pins $P_A$ dip into the commanded wells for resupply. The pins rise again, the multiwell reservoir moves laterally with $Y_2$ motion out of the way and the deposit process is repeated at new targeted X,Y location of the pins on substrate R or $R_1$. While this mobile reservoir technique is useful with pins of any construction, the advantage of high accuracy of the linear motor indexing system is enjoyed when the pins are constrained in space to a highly accurate repeatable position relative to their carrier, either with the high density pin arrangements made possible by the structures described with respect to the various FIGS. 1, 2, and 3 or the flexure mountings that have been described with respect to the FIG. 4.

Multiple Pin Patterns

In the preferred embodiment of FIG. 12, two rows of 4 pins P, preferably constructed according to FIGS. 1–4 are spaced apart in a 9 mm square grid pattern matching the spacing of the wells of a 96 well plate. This permits transport of fluid from all 96 wells, 8 wells at a time to an assembled array of microscope slides, according to the scheme of FIGS. 13 and 14, and directs the composition of 8 spaced apart blocks of approximate dimension each 8×8 mm on each slide, covering in total approximately 18×36 mm sq. Each pin deposits in a respective one of the 8 blocks simultaneously with a single actuation of the Z drive. The head repeats the action on each of the set of slides with the same fluid, and is then cleaned to be ready for fluid from different wells. The same pin may be used to deposit the same fluid at a number of directed positions in a given block, and/or upon the corresponding block of a number of slides each having the set of 8 spaced apart blocks, the deposits on the slides being much closer than the spacing between wells. By following the sequence shown in FIG. 14, all wells may be visited by respective pins. FIG. 15 and the magnified view of FIG. 15B show the array produced by the system and method described on a single slide. (Actually the dot size in practice is much smaller than illustrated and dot density much greater, e.g., with as many as 50,000 or 100,000 dots carried by a single slide.)

In a similar preferred embodiment, shown in FIGS. 16, 17, 18, 19, and 19B a grid of 12 pins has 2 rows of 6 pins each, FIG. 16, again spaced apart in a 9 mm square grid pattern to match the spacing of the wells of a 96 well plate. This arrangement permits the transport of fluid from all 96 wells, 12 wells at a time, and directs the composition of 12 spaced apart blocks of approximate total area 18×54 mm sq. FIG. 19 shows such an array.

With either arrangement, the method is performed under computer control to form a much more densely packed array of fluid dots than that occurring in the multiwell plates, e.g. arrays of 20 micron to 375 micron diameter dots with similar spacing between dots, using all fluids in the plate.

Just as the pins are located on 9 mm centers, the square arrays themselves are distributed on 9 mm centers over the face of the substrate. By following the pickup sequence shown in FIG. 14 (rows 1 through 2, and columns A through H), by repeated samplings, all wells are visited, the pins being conveyed under computer control to the cleaning station, not shown, between change of fluids. The contents of the multiwell plate or a number of plates are thus distributed from the low density distribution of wells in multiwell plates to high density arrays.

Similarly, referring to FIGS. 16–19, again using 9 mm pin spacing, with two rows of 6 pins each, a sequence of samplings from the wells under computer control collects samples from all wells and uniquely distributes them as high density array deposits in 12 squares on the microscope slides or other substrate with array and slide dimensions as shown in FIG. 19.

The benefit of such groups of pins is to create a large number of deposited dots simultaneously on one or many microscope slides or substrates. This can substantially reduce the time and cost required to create high density arrays.

The assemblage of pins on a 9 mm square grid can also be used to transport fluid from plates with well spacing constructed on a square grid that is based on sub multiples of 9 mm, such as plates with 384 wells or 864 wells or 1536 wells, etc. The high accuracy of the computer controlled gantry system enables accurate placement of the selected wells with respect to the pins, and the pins with respect to the receiving substrate.

It is evident that using the same logic, pins can be assembled in denser constructions to fit plates with smaller well spacings.

The denser the array, the tighter the location tolerances for the location of each small dot. The systems of laterally constrained deposit pins described in FIGS. 1–4 are particularly capable of repetitive production of precise high density arrays. Using these principles, the mode of supplying the tips with fluid can be selected in reference to the nature of the fluid as well as other operating parameters. A ring supply mode will now be described.

Pin & Ring System

Figure 20A:
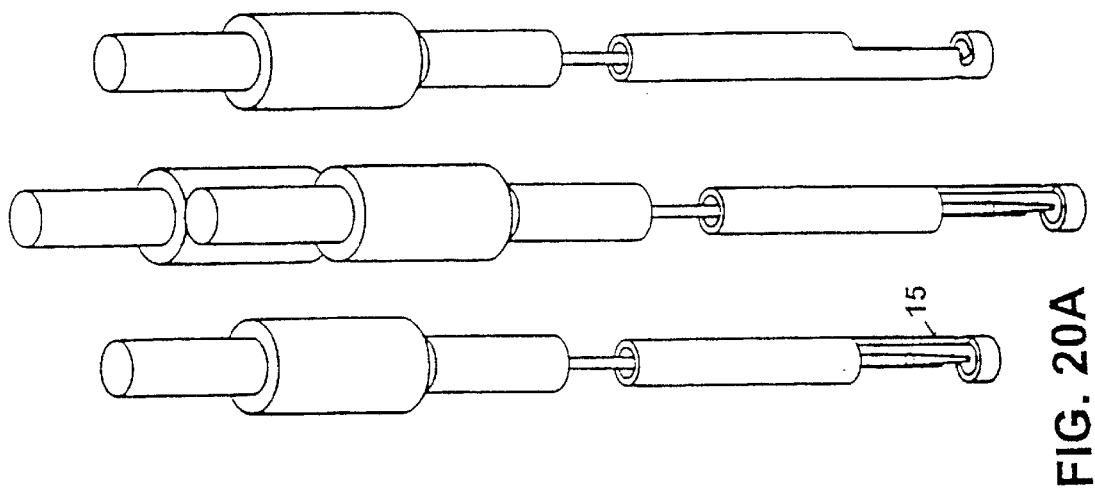
FIG. 20A is a similar view of a group of four such assemblies.
Figure 20:
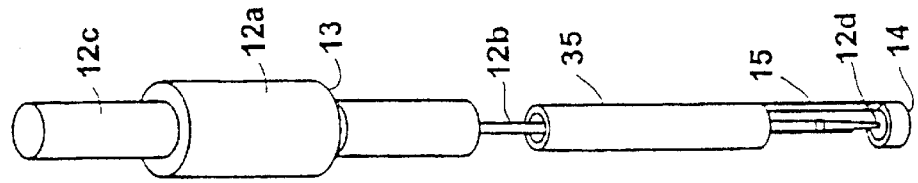
FIG. 20 is a perspective view of an assembled deposit pin constructed according to FIG. 2 combined with a respective supply ring.
Figure 21:
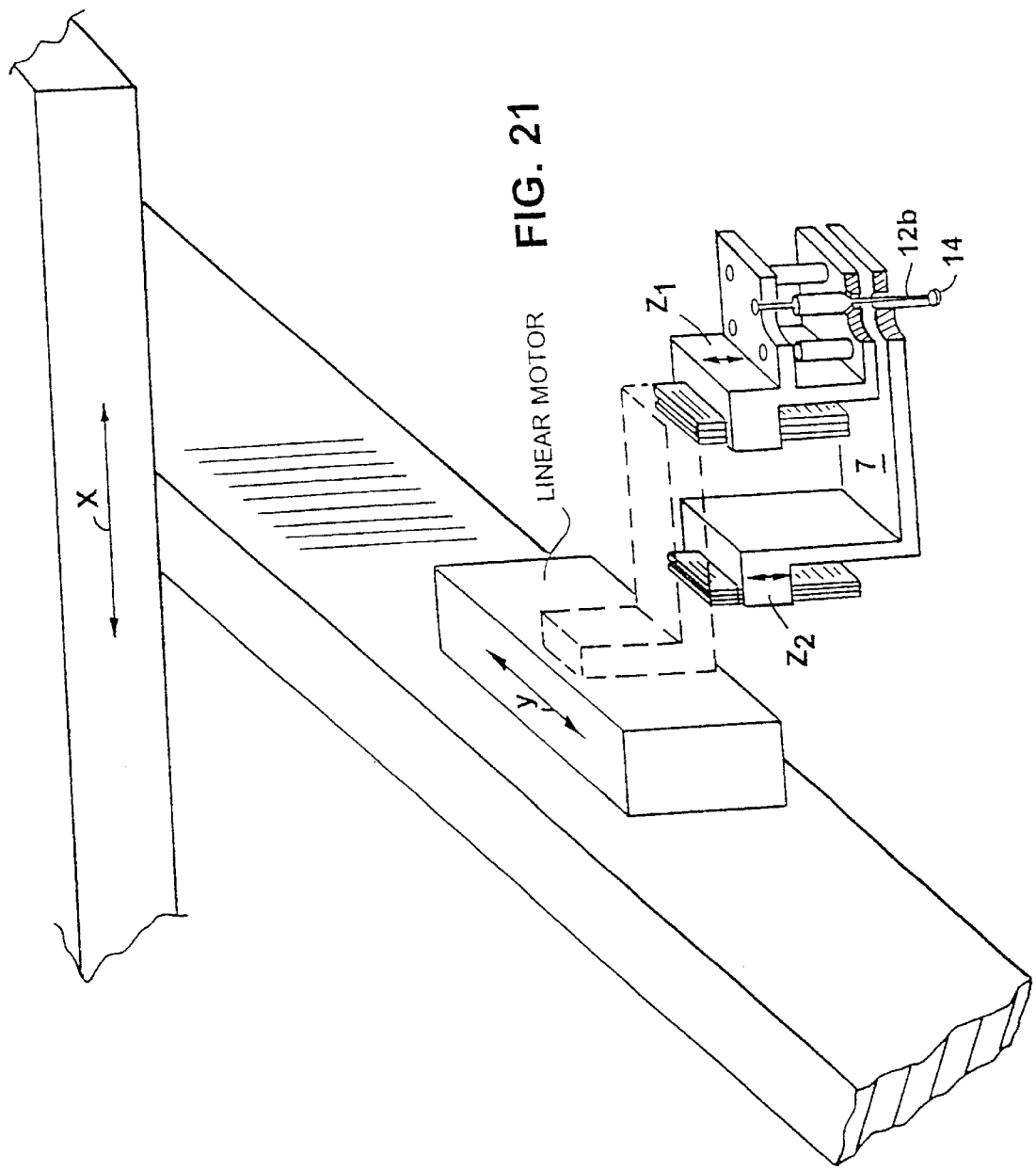
Figure 22:
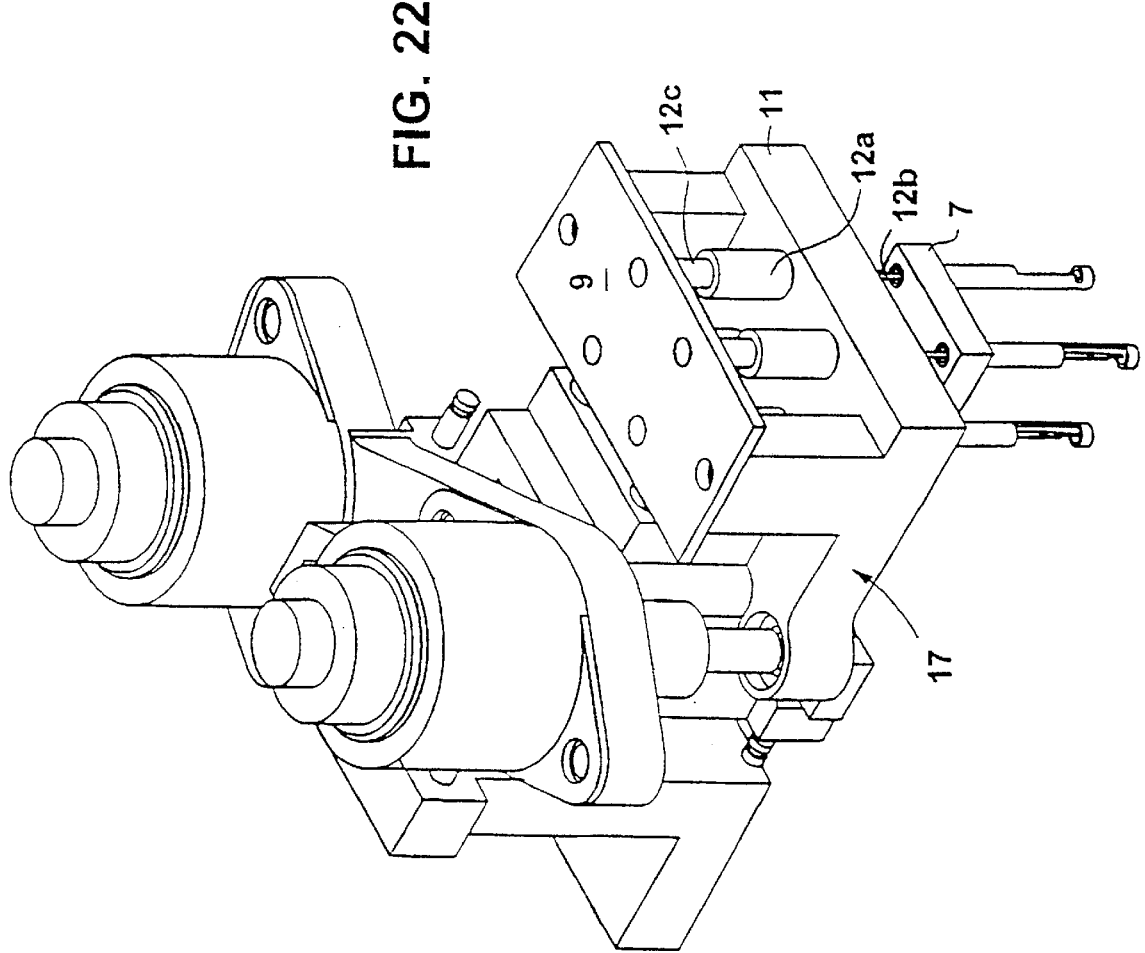
FIG. 22 illustrates an arrayer system, employing a group of assemblies of FIG. 20A or FIG. 21 constructed for commercial use.

The pin assemblies as shown in FIGS. 1–4 can be used with a simple axial ring translation mechanism. As the fluid needs to be picked up from a rather large well, a sufficiently compact arrangement of multiple pins and supply rings is possible. FIG. 20 shows the relationship of a pin and ring without their support or actuation mechanisms. Seen in FIG. 20 are supply ring 14, pin tip 12d, ring body 35 from which a support rod segment 15 extends to the ring 14, pin shaft 12b, the pin seat 13 formed on pin body 12a and pin guide 12g. FIG. 20A shows a set of four such pin and ring assemblies. It is evident that any number can be assembled in this fashion. FIG. 21 depicts a 4 pin and ring assembly where one can see the pin holding structure, according to FIG. 2, and the ring holding structure and their respective linear stepper motors $Z_1$, and $Z_2$ that enable relative vertical motion. The $Z_1$ motion for deposit on a receiving surface preferably involves overtravel, the compliance of the deposit pins relative to the receiving surface ensuring proper deposition over a range of surface heights. The respective supporting linear guide rails for X and Y motion provide a complete array-forming mechanism. FIG. 22 illustrates a commercial realization of the design which attaches to the Y stage linear motor of FIG. 21.

Figure 23B:
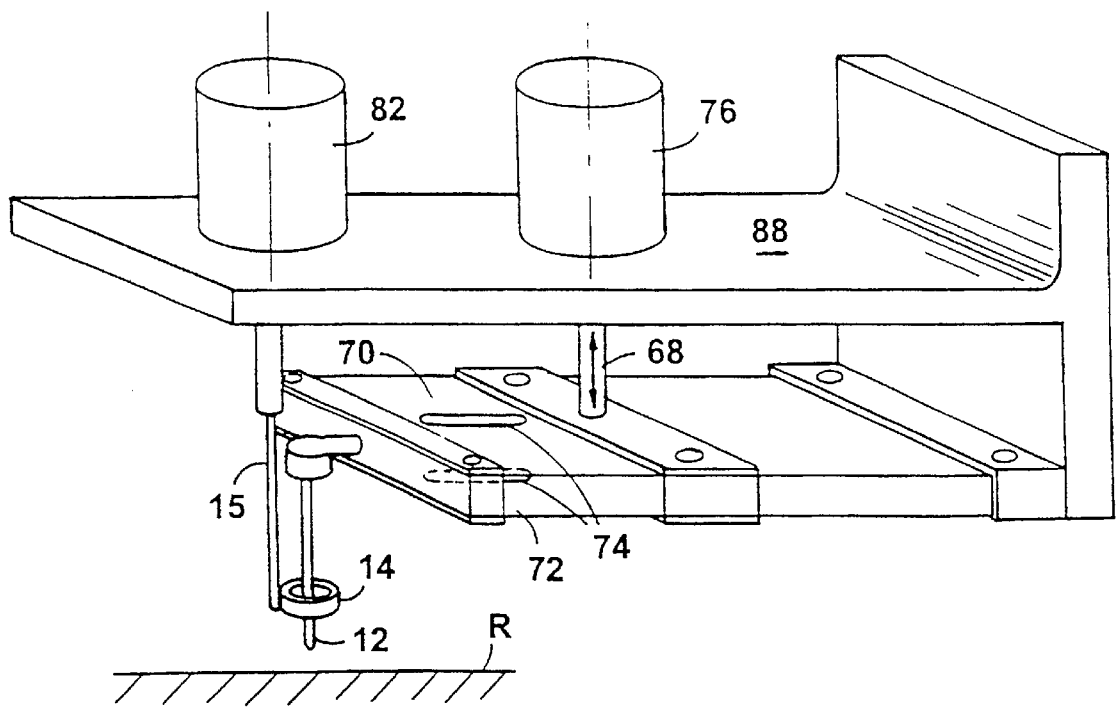
FIG. 23B is a perspective view of the subassembly of FIG. 23 combined with drivers for the pin and the sub-reservoir supply ring.

Referring to FIGS. 23, 23A, and 23B, deposit pin 12 in this case is mounted on a parallelogram, cantilever construction. Spaced-apart planar flexures 60 are mounted in parallel on a mounting block 62, sandwiched by mounting plates 64 and 67 against the intervening block 62. These flexures extend in cantilever fashion to intermediate block 66, arranged to be engaged by pusher rod 68 associated with a prime mover 76, FIG. 23B. Extending further in cantilever fashion from intermediate block 66 are parallel flexures 70 and 72 which include cut-outs 74 that render the flexures weak and highly flexible (compliant). At the end 79 of weak flexures 70 and 72 is mounted deposit pin 12. The condition of no force being applied to the structure is shown in FIG. 23 in which the flexures are horizontal, the weight of the pin being borne by the mounting structure. In FIG. 23A, force applied in the direction of the arrow 68 results in deflection of the stiff flexures 60 to the shape shown, such that block 66 remains parallel to the receiving surface and deposit pin 12 remains in perpendicular position to the receiving surface. (Thus the relatively stiff flexures 60 and the associated driver perform the function of a precision stage.)

The flexures may be comprised of synthetic resin cut to shape, e.g. polyamide resin, available as Kevlar™, from dupont, or etched from thin spring metal such as beryllium copper or stainless steel. Advantageously both the stiff and weak flexures are formed continuously from a single sheet of spring stock.

In FIG. 23B pusher 68 is driven by rotary motor 76 via lead screw, not shown. The sub-reservoir ring 14, mounted on support rod 15, likewise is driven by motor 82 via a lead screw, for vertical motion of the ring.

The motor may advance the pusher 68 a predetermined distance from a home position for each deposition action, or to the level of a position sensor which terminates the motion. The microscope slide or other substrate surface R may lie at slightly different levels due e.g. to permitted manufacturing tolerances. The stop position of pusher 68 involves sufficient overtravel to ensure contact of the deposit pin 12 with a microscope slide or other object of the least thickness within the tolerated range of thicknesses. The compliance provided by weak flexures 70 or 72 (or the other arrangements discussed above), ensure, if the microscope slide or other substrate is considerably thicker than normal, that the deposit force will still not exceed a predetermined value, typically less than 1 gram, preferably less than 0.5 gram, for ensuring precise dot formation and protection of the tip of the pin.

FIG. 24 shows a deposit cluster 28 of independently operated deposit pins, formed by a number of the deposit assemblies described in the FIGS. 1–3 and 4. Cluster 28 includes, not shown, a number of independent drives D and D', one to drive each pin and one to drive each ring in Z direction for picking up and depositing fluid, and sensors to indicate to the control electronics the position of the operative elements. There is a home sensor for each deposit pin 12 and a home sensor for each ring 14. The devices are ganged mechanically for X or X,Y movement, positioned by a common electronic control. (Motion only in the X direction is employed when a stage is provided to advance the receiving substrate in the Y direction).

The cluster 28 may step to a selected X or selected X,Y position, at which a number of different motions under computer control may be caused to occur, picking up and depositing fluid in any order at any location desired. Such a cluster constitutes a particularly versatile tool when employed with conventional microtiter plates.

In such embodiments the aliquot carrier rings 14 and pins 12 are spaced in the cluster at 9 mm center-to-center distances or multiples thereof to facilitate operation with 96 well plates (in which the wells are spaced at 9 mm on center intervals, with 8 rows of 12 holes). Higher density plates also employ this configuration and have the same footprint but employ more holes, 16×24, with hole-to-hole resistance of 9/2 mm, to provide "384 plates". The arrangement of FIG. 24 enables use of the higher density plates with existing automated 96 well plate handling equipment. The system described can be employed with both types of plates, as well as any arbitrary arrangement.

The versatility of the cluster of independently operable deposit pins is illustrated by the following examples.

Sub-reservoir rings, e.g. set at 9 mm center-to-spacing, may be indexed in X,Y direction along with their pins and the rings may be driven down (or dropped) simultaneously for supply or resupply from four wells of a conventional 96 or 384 well plate, in an action similar to the systems previously described.

After suitable indexing, the four pins may be driven down simultaneously to form deposits at four places, in the same format as the supply plate.

Alternatively, during resupply, one sub-reservoir ring may be dropped to pick up material from a selected well while all others remain in their passive positions. Then the cluster may be moved until the next ring arrives at the same well or another selected well, at which point it is dropped to pick up its aliquot, and so on, so that all of the rings may have the same fluid from the same wells or different fluid from any selected wells.

The cluster 28 may be moved in X,Y direction between pickup or deposit actions of successive pins so that, e.g. all of the pins deposit the same or different fluid on a single slide at selectable addresses or each pin addresses a different slide, but at a different location, or two pins address one slide and two another slide, or the deposits are made one on top of another, etc.

The operator may also choose not to have one or more of the devices operating.

Thus it is seen that dense clustering of independently operable deposit pins and rings according to the system of the FIGS. 1–3 and the systems of the FIGS. 4 can enable high speed, versatile operation.

Figure 24D:
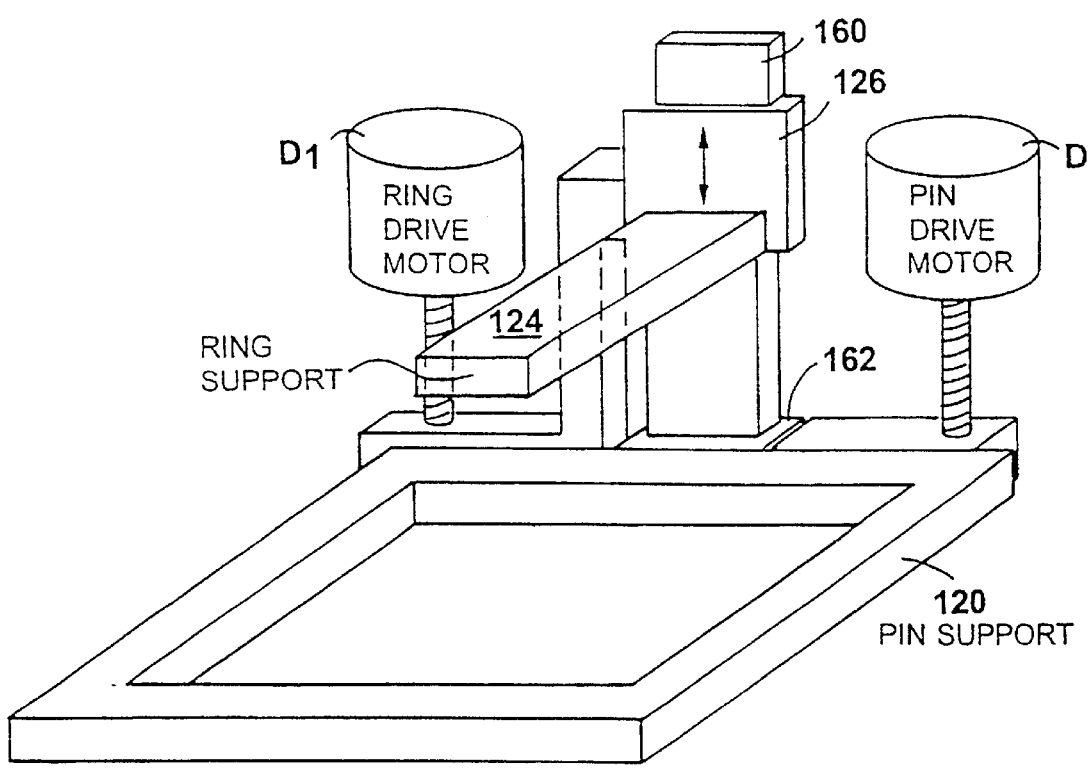
FIG. 24D is a perspective view of the ganged system driven by a linear stage.

Actuation of all aliquot carriers simultaneously by one actuator and all pins actuated by another single actuator, to provide a multiple pin head, realized with flexure-mounted pins, are shown in FIGS. 24A, 24B and 24D. Using linear stage techniques, two rows of four pins 12 at 9 mm spacing in both X and Y directions are all mounted on a frame 120 which is reciprocated along rail 160 via carriage 162 by a single motor D. This causes the eight pins to move simultaneously. Likewise, two rows of four cooperating rings 14 are mounted on ring support 124, with the same spacing. The single support 124 is driven via carriage 126 by one motor $D_1$. In the embodiment shown, both embodiments share the same guide rail 160. The pattern of dots shown in FIG. 24C is formed by a single actuation of motor D, FIGS. 24A and D.

Arrayer

The gantry of an arrayer, now to be described, can carry one deposit head, a cluster of independently operable single pin heads, or a multiple pin head of the various designs described above. Combinations of these are also possible.

Figure 25:
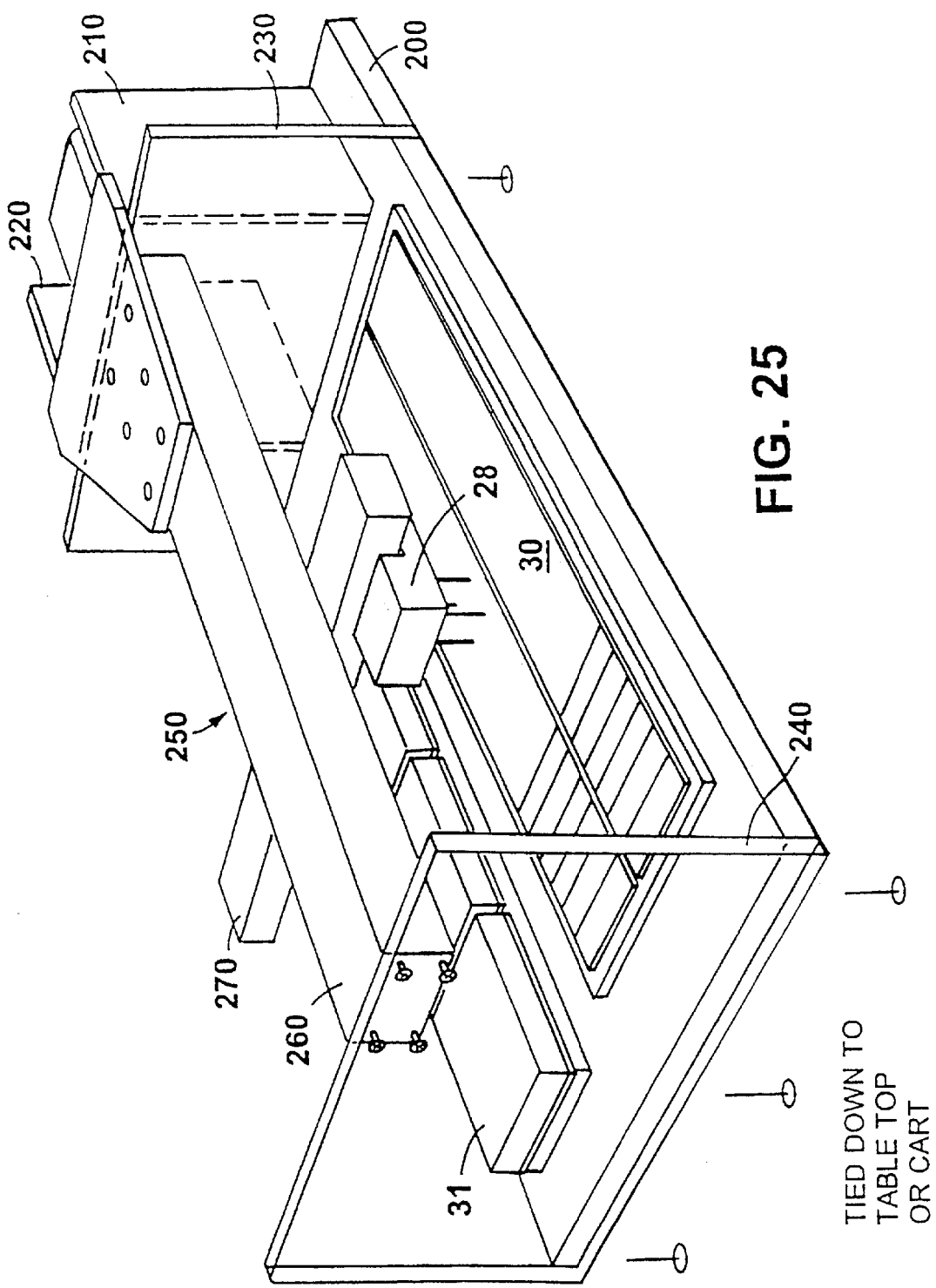
FIG. 25 is a perspective view of a machine for depositing dots of biological fluid in dense array upon a series of microscope slides.

FIG. 25 is a perspective view of a slide preparation machine for preparing microscope slides or other substrates such as delicate soft or porous membranes carried on rigid supports. Its function is to rapidly deposit a high density array of fluid dots of different compositions on a number of identical substrates, employing the microdot technology of the present invention. As shown in FIG. 25, there are four 96 well supply plates 31, serving as the central fluid source for resupply of mobile fluid storage devices.

Horizontal base plate 200 provides a support structure to hold the operating components. Fastened to base plate 200 are vertical sub plates 210, 220, 230 and 240. Fastened to these plates is a dual axis motion system 250, comprising X and Y axis devices 260, 270 for providing X and Y motions, in a parallel plane.

The guide rails of the X and Y axis devices, 260, 270 are parallel to base plate 200, to carry deposit cluster 28 in X,Y motions in a plane parallel to base plate 200.

The X axis device 260 is a commercial device available from Adept of Japan. It moves at a high rate of speed in a controlled manner using a rotary servo motor with a drive screw and a shaft position encoder, employing digital and analog technology. Carried by X-axis device 260 is an orthogonally arrayed Y-axis device 270 which is a smaller version that operates in the same manner as the X-axis device.

The deposit cluster 28 comprises four deposition mechanisms, ganged together on a mounting structure as shown in FIG. 24. These devices may be in accordance with the various structures shown.

After a deposition sequence is complete, the X and Y terminal drives the cluster of depositing elements to a cleaning station. In some embodiments they may be passed over the wells from which the fluid originated or other receptacle and subjected to air blast to dislodge excess fluid, or excess fluid may be removed by abrupt stopping of rapid downward movement to dislodge excess fluid.

In the system of FIG. 25, the array of pins and rings of a cluster 28 may be held over a vessel of water for cleaning, as shown in FIG. 9F. The vessel has water level and a pump constantly replenishes the water. Blotting paper or a cellulose sponge may be provided against which the pin and ring are blotted for fluid removal or drying.

Alternatively a fluid removal station according to FIG. 9G is employed where air flow removes remaining fluid from the pins and rings. The array of 4 pins thus purged of remaining fluid by air blast is then, by warmed air, washed and rinsed by liquid or aerosol streams and dried.

Figure 26:
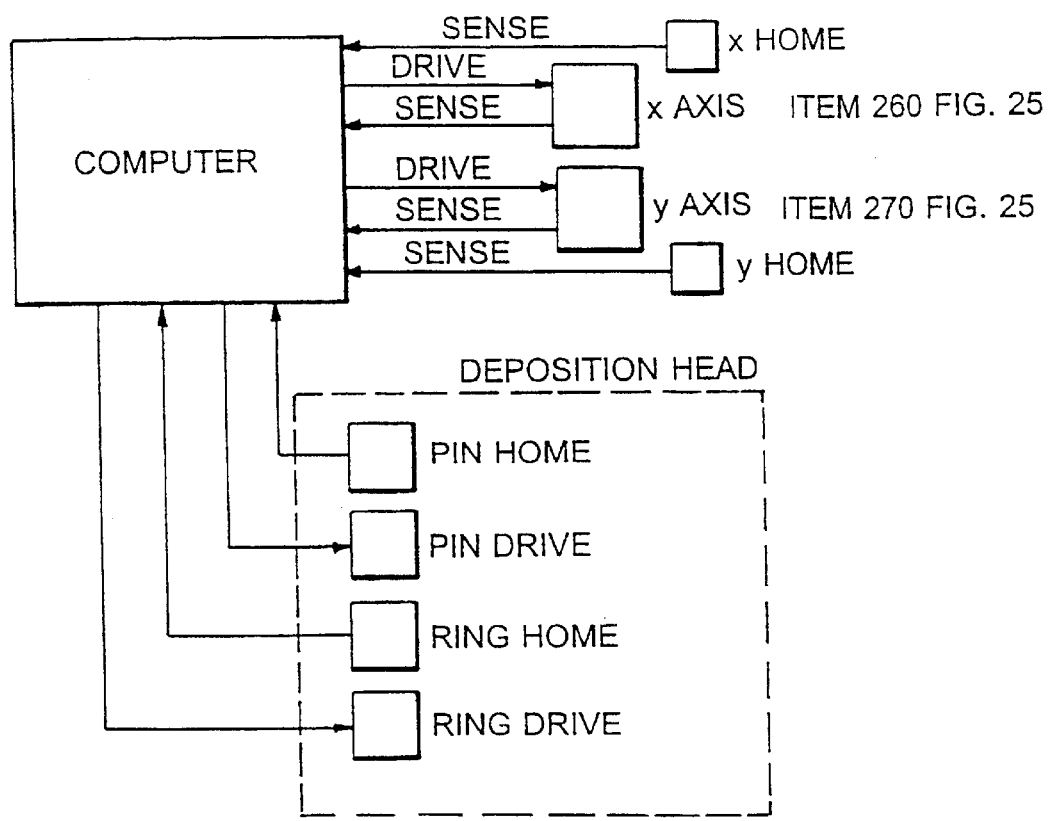
FIGS. 26 and 27 show features of the control system software and method for conducting the deposit action.

FIG. 26 shows the control system of the machine. It shows the controls for the X and Y axis movement and also home center for the X and Y axis. The actual position of the carriage that the lead screw is driving is sensed so the carriage can be driven home and then the counter is initialized so precision motions can be made along both the X and Y axes. Also shown is a schematic of the deposition head, one of many. As previously described, each deposition head has two motors, a pin drive motor and a ring motor, that are commanded from the control computer.

For deposit on microscope slides including slide-like rigid members carrying delicate, soft membranes, the slides are fastened to the table, or placed in register with guides in a known position. Features on the base plate of the machine locate the slides in predetermined orientation.

Figure 25A:
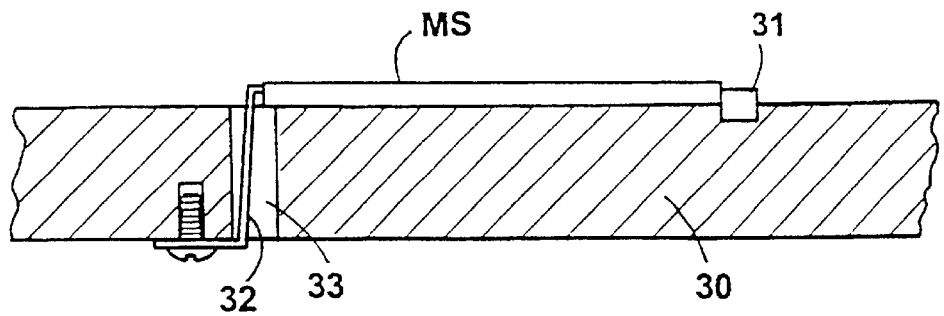
FIG. 25A is a side view of a slide holding arrangement useful in the machine of FIG. 25.

In the preferred embodiment of FIG. 25A, microscope slide MS rests upon slide support 30, having one end engaged with stop 31 and its other end engaged by a spring wire 32. Wire 32 extends from a support screw on the bottom side of support 30, through a hole 33 in support 30, and is biased to the right in the figure to engage the slide MS to urge it against stop 31. The spring pressure is sufficient to hold the slide MS endwise in secure, accurate position despite vibrations that occur during operation of the machine.

Figure 27:
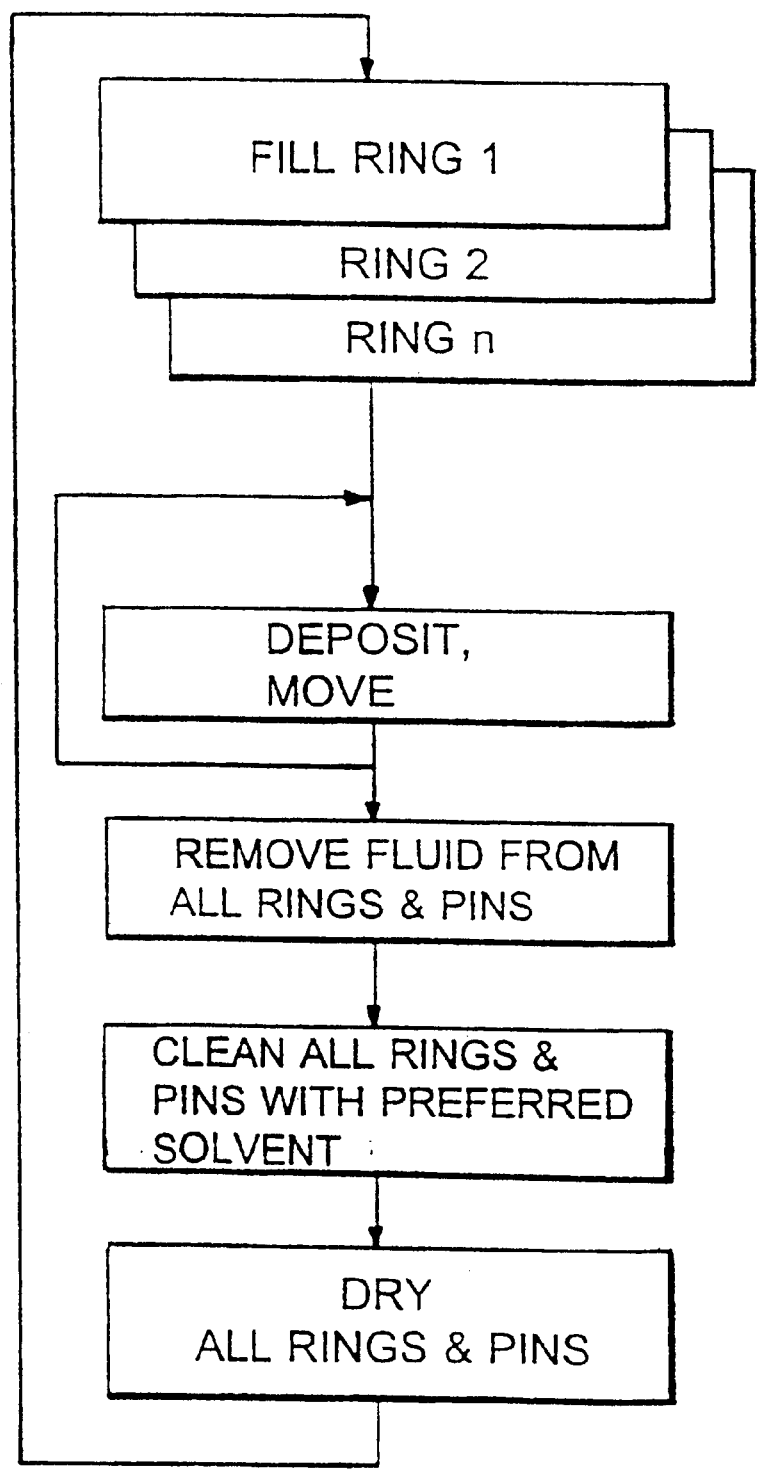

The slides are mounted side-by-side in subgroups of seven slides, with their thin long edges engaged with one another. The seventh slide's position is dependent only upon the tolerances of the preceding six slides. By having such sub groups, one is assured that the array is properly located. The computer is enabled to "talk" to the slide and to record information, as in bar code. The bar code reader is mounted on the servo drive 270 of the Y axis and adjacent to the deposition means 28. The sequence starts with filling the multiplicity of rings of the deposition device, and is carried out according to the control procedure of FIG. 27.

For use in high volume production contexts, the system described in the foregoing FIGS. 1–27 preferably employs a rapidly moving, laterally constrained, axially compliant pin, in a deposit cycle of less than 0.1 second, in which impact and vibration is minimized, with the natural frequency of the system more than 10 Hz, in many cases preferably 20 Hz, a pin contact pressure of less than 1.0 gram, preferably less than 0.5 gram in many cases preferably about 0.3 gram, and the system employing damping.

Pin pressure on the substrate is light, and fluid splatter or separation conditions are thus avoided, despite the high speed of action, so that dots of fluid of uniform shape are consistently formed at precisely controlled positions, even on soft or fragile receiving surfaces.

In the deposit action of the deposit pin, by raising the pin after contact of the drop on the substrate, the combined effects of inertia of the stationary fluid and surface tension (and of gravity, when depositing downwardly, which is normally preferred) act upon the drop of fluid to overcome the force of surface tension exerted by the lifting pin. The fluid drop preferentially stays with the surface of the substrate, and the pin, substantially devoid of fluid, is free to be replenished and move rapidly to its next destination.

As the volume of the fluid is accurately specified by use of standard sizes of pin, and standard conditions, and the position of the pin is precisely constrained, spots, dots and microdots of consistent size and precise location are produced, that enable an improved degree of quantification of observed results.

D. Examples of Novel Methods of Use

The systems described are useful with any native fragment of DNA, or pre-synthesized oligonucleotide of any length. There being no restriction as to chemicals, any non-photoreactive chemical as well as photoreactive chemicals can be employed. Likewise dyes that are useful to detect presence or absence of DNA may be selectively deposited in registry with previously deposited spots or microdots of biological material, and vice versa.

Among the many biological materials that may be spotted at high speed are fragments of nucleic acids, e.g. DNA, RNA or hybrids such as PNA (peptide nucleic acid), PCR (polymerase chain reaction) products, cloned DNA, and isolated genomic RNA or DNA, as well as synthetic analogs.

Also included are restriction enzyme fragments, full or partial length cDNA, mRNA or similar variations thereof, proteins such as protein receptors, enzymes, antibodies, peptides and protein digests; carbohydrates; pharmaceuticals; microbes including bacteria, virus, yeast, fungi, and PPLO; cells and tissue fragments; lipids, lipoproteins, and the like; plastic resin polymers, small particulate solids in suspension, etc.

The deposition system may also be employed to deposit catalysts, reagents and encapsulents upon previously deposited material of any of the types above or, as mentioned below, to create an array of sites or micro-wells for later reaction or growth of such material, or to assist in neutralizing or cleaning the deposit or reaction sites, as in the case of highly toxic or virulent substances.

The most basic use of the arrayer is to create high density arrays of nucleic acid on a porous or solid, flat surface, generally a microscope slide or slide-like support. Deposit on fragile or soft surfaces such as microporous membranes or gels, glass cover slips, plastic surfaces, and wells of a microplate, or any substrate, which may be previously coated or derivatized, may serve as a recipient surface.

In particular, membranes and gels are desirable to enable high density analysis with automatic equipment, using materials familiar to the field, on which much of the important, historical data has previously been acquired. Also, deposit on fragile glass cover slips is desirable as they are thinner than microscope slides, easier to maneuver, and when a beam of light is transmitted through them for transmission microscopy, better light capture occurs because the slip is thinner and less light absorptive. The system has the capability of spotting on plastic surfaces without scarring or deforming the surface.

The avoidance of such surface deformation can be important, enabled by use to low contact forces of the compliant pins. An undeformed surface can facilitate viewing with a confocal microscope, as it assures that the deposit remains in the plane of focus.

Use in wells of microplates is important. As has been mentioned, the narrow lateral dimensions of the deposit pin, and its long length, enable deposit in multiple locations on the bottom of a well, or other fluid containment region. For example the arrayer may be employed to deposit a number of spots in known locations on the bottom of a well to perform clinical tests on an analyte fluid. For instance, each spot in an array in the bottom of a well can be a known nucleotide probe. A sample added to the well will hybridize with spots with which the sample matches. For instance a diagnostic test may employ a 96 well plate to measure binding to as many as a hundred different probes printed in known locations in the bottom of each well. Different patients' samples may be placed in respective wells, to conduct many evaluations at once using a single multiwell plate.

Another use of the system is to deposit, at useful speeds, a statistically determined number of molecules or units into a single well. Employing a suspension of suitable concentration in a supply ring with an appropriately sized pin, thrusting the pin down once per well, statistically, can deposit the desired quantity, which then can interact with nutrient, experimental drug, etc. in the well.

The concept of insertion is extended to include the deposit of particulates in suspension, for example, to deposit cells and then afterwards, deposit a suspension of particles of asbestos or precipitated silica or other solids of interest, to investigate effects of the particles upon the cells. These are examples of inexpensive, highly accurate, micro-controlled experiments that can be conducted at efficient speeds using the dedicated aliquot reservoir and deposit pin.

In many important cases the fluid or liquid carrier of the deposited spot evaporates and the biological or other material carried in the fluid stays in place by adhesive or bonding properties of the dried material. In other cases, the spotting technique is useful to deposit fluid that remains in a fluid state, for instance, as mentioned, to deposit cells into wells with fluid nutrient medium that enables the cells to continue to live.

In many cases it is important to know where a deposit is and that it will stay in the deposited position when covered by a common reagent. Steps can be taken to secure the deposit in position, for instance, with DNA, by exposing the deposit to UV radiation to crosslink the material or to use a derivatized surface that produces crosslinking between e.g. DNA and the surface on which it is deposited. An example is a silenated surface coated with E.S. aminosilene, to provide a positively charged surface which binds, by ionic or electrostatic forces, with negatively charged deposits such as DNA.

In addition to applicability in bioresearch and clinical diagnosis, the deposition system has applicability in the chemical laboratory, e.g. to analyze fluids, such as for water quality, or to experiment with resins, for instance polymerization reactions, to conduct experiments in small quantities of many different varieties, e.g. to determine optimum ratios and optimum selection from a host of slightly varying examples. The range of usefulness is broad with application to small quantities, different temporal sequences, different kinetics of reaction, and different mixtures. In all of these cases, the system is a precise way of manipulating small amounts of liquid, solids in liquid suspension and cells in suspension, under controlled conditions.

Deposition with the systems described leads to rapid and precise observations, reduction in the number of trials for a given experiment and improvement in the statistical significance of the data. Cost savings and improved experimental procedures can be realized. Quantification of results at accuracies heretofore unknown may be attained by consistent and precise dot formation that enables improved signal-to-noise ratio in detection, when sensing the difference between, e.g., the fluorescence of a deposited spot and the immediately adjacent background surface of the substrate.

The system is useful in many environments due to the attributes of the deposit apparatus, and the techniques by which movement and control is effected. The following are further examples.

The system is used to deposit dots of fluids of high volatility such as alcohol-based fluids, upon rigid substrates such as glass or silicon, upon membranes, etc. The relatively large mobile local reservoir ring that travels with the deposit pin to the deposit site presents a relatively small exposed surface-to-mass ratio, which limits evaporation. Transport from that volume of the tiny sample on the tip of the pin, over a short local distance, limits exposure of the tiny sample to evaporating conditions until the dot of fluid is deposited.

Where desired, the operating deposit mechanism is shielded from windage by a protective shield mounted on the head to move in X–Y directions with the deposit mechanism, to further limit evaporative loss. In another case, the environment in which the system operates is controlled, e.g. at high humidity, or high partial pressure of the volatile substance, to limit evaporative loss, or at particular controlled conditions, e.g. controlled temperature and humidity, to favor the deposition process or the operation of the system itself.

Time-based sampling to evaluate chemical reactions or growth stages can be performed automatically without attendance of laboratory personnel. In one example, the fluid carrier ring through which the pin operates is employed as a reaction vessel from which samples of the continuing reaction are periodically taken by an associated deposit pin, and deposited for later inspection.

In this or other examples, at prescribed time intervals, another pin moves through its ring to deposit an inhibiting reagent to halt the reaction or growth that is occurring at a respective location on a substrate. By doing this at timed intervals over different locations on an array of identical reactions, a fixed array that represents the sequence of conditions at the various time intervals is preserved for later examination.

In another method employing the deposit system, an etchant fluid is provided in a local reservoir ring. The pin of the deposit pin distributes the etchant in tiny, precise spots or microdots in a desired array across a reactive substrate surface. For instance, for forming micro-wells for containing fluid, the device deposits an acid such as hydrochloric acid in an array of small dots upon a silicon substrate. An etching reaction occurs, and the substrate is then neutralized and washed, to produce a corresponding array of small wells. These may have advantageous hydrophilic, fluid-retaining surfaces as a result of the etching process. Following this, the same depositing system may be employed to deposit one or more substances precisely in registration with each of the wells for use in reaction or growth processes that are desired. Plates thus prepared may be transferred e.g. to a wide field scanning microscope for observation.

Arrayers as described can also be used for color printing of fabrics, paper etc., where the 96 well plate holds different color inks or dyes. The area to be printed is the entire reach of the gantry less the color source and washing station.

The arrayer can be used to generate a single printed circuit board, e.g., prototype boards, or boards for limited volume production, where the machine is employed to deposit varnish or photoresist or other protective coating material to define the regions of the copper clad or other substance which need to be preserved from acid etching. Likewise the arrayer may be employed to deposit photoactive substance for production of "biological" deposits using lithographic techniques.

E. Combination Arraying and Microscopic Analysis

It is an important further feature of the invention to combine the arrayer of any of the presented embodiments, or its steps of action, or array products of its operation, with a scanning microscope, especially a wide field scanning microscope such as available from applicant. The principles described here enable wide area arrays to be formed of very high density over the mentioned wide range of fluids and conditions, while wide area scanning microscopes enable commensurate accurate and inexpensive reading of the results achieved with such wide arrays. The wide area and precision capabilities of each system and method, in combination, complements the other to achieve an enabling, significant advance in microdot reaction and analysis. Use of an array of flurophor-tagged components, such as is employed in biotechnology, or flurophor-tagged contaminants, followed by reading with a suitable wide field scanning microscope that excites the flurophors is of particular advantage.

F. Useful Additional Features

In one embodiment, an inductive heater station is provided to which the deposit mechanism can travel under computer control. In this case the substance of the reservoir ring and the deposit pin, or at least the surface portions of these devices, are comprised of electrically conductive material capable of having electrical currents induced by an alternating field of the induction heater. Under computer control, the reservoir ring and the pin are delivered for a momentary pause in the heater, for heating based on resistive ($I^2R$) losses by the induced electrical currents, for instance to sterilize the reservoir ring and deposit pin or to stop bioactivity in the fluid material retained on the instruments.

In another instance, a reservoir ring containing a charge of reactant fluid, which is desired to be heated, can be introduced to the inductive heater, and the fluid is heated by heat-transfer to the fluid from the inductively heated ring. Such heating can be employed to initiate a reaction in the fluid, for subsequent deposit.

Another system includes a delivery system for relatively larger quantities of fluid, e.g. to fill a micro-well with nutrient, diluent or reagent after deposit of a spot of the fluid of interest. The delivery system, such as a computer-controlled pipette, may be associated on the same head and X–Y carriage with the deposit pin, or in a separate head or carriage. By functioning under computer control to deliver larger quantities of fluid to reaction sites where dots of fluid have previously been deposited, an entire experiment can be automated. Fluids which may be introduced in this way include, for instance, solvents, etchants, sterilizing agents, cleaning agents, encapsulating coating materials, etc.

In another method the deposit pin is caused to deposit reagents at selected sites in differing amounts at differing locations, to effectively conduct titration, to observe a reaction at different concentrations of the reagent. Thus, at one reaction site (e.g. a flat area or a well on a substrate) the deposit pin may deposit one precise drop of reagent, at a second see two precisely identical drops of the reagent, at a third selected site three precisely identical drops of the reagent, and so on, to provide the full range of concentrations desired for evaluating reaction of the reagent with another substance that has been preapplied to the site or that is subsequently applied.

While such systems are particularly well suited for laboratory experiments, they also can be employed in industrial process control.

A variation of the spotter mechanism employs, in a fashion analogous to that of a modern milling machine, a set of interchangeable heads having different capabilities. Under computer control, an X–Y carriage of the system is moved to select a desired head which is carried across the substrate to perform its function. In some instances the device selected may be a sub-reservoir ring from a set of such rings that have different internal diameter or are formed of different wire or ribbon sizes, or are of different sizes to enter different wells, etc. These provide a variety of carrying capacities for fluids of different viscosities or for use with deposit pins of different sizes. Likewise, different sizes of deposit pins can be selected from a set of pins to vary the size of the spot to be deposited. Heads can also be selected that provide other devices for preparing for or conducting experiments or for the production of reference or diagnostic well plates and slides.

In some cases the selection and use of devices can be conducted under complete computer control to enable automatic performance of a multi-task experiment un-attended by the technician.

In addition to depositing spots of fluid upon a standard microscope slide, and upon porous or soft membranes and other delicate substrates, it is possible and advantageous to deposit spots on substrates of significantly larger area and on other substances and on surfaces having special formations, for instance upon substrates having micro-cavities that have been formed by the instrument itself, by one of the techniques described above. Plates delivered with the micro-cavities preformed in the substrate may also be used, and aligned for deposit of fluid by automatic controls of the instrument, or the control system of the unit is advantageously provided with a vision system that "reads" the location and pattern of the array of microwells, and adjusts itself automatically or under operator control to accurately deposit dots of fluid in wells.

F. Conclusion

In the various ways described, a large array of fluid deposit sites may be established and managed in a precise, repeatable manner that employs the same concentrations or reactions or precisely varied concentrations and reactions. This may be done to enable examination, to promote reaction or growth processes in biotechnology, life sciences, chemistry, pollution detection, process control and in industry in general.

Thus, beyond an instrument for low-cost preparation of microscope slides and membranes for biotechnology research, there has been contributed a universal and widely variable set of systems, instruments, methods and products that can advance research and industry.

Numerous other embodiments not described in detail here can apply the principles described to particular applications and are within the scope of the claims.

What is claimed is:

1. An apparatus for depositing fluid dots on a receiving surface in an array, comprising:

a deposit device cooperatively related a fluid source including biological material;

a drop-carrying element coupled to and displaced by the deposit device;

a fluid-retaining structure, co-operatively arranged with the drop-carrying element, constructed to retain fluid including biological material by surface tension, the fluid-retaining structure being constructed and shaped for at least partial immersion into a well including the biological material;

a transport mechanism for positioning the deposit device and the drop-carrying element at a precisely referenced position over the receiving surface; and a drive mechanism for moving the drop-carrying element, relatively through the fluid-retaining structure to receive the fluid including the biological material, in deposition motion toward and away from the surface.

2. The apparatus of claim 1, wherein the fluid-retaining structure includes a ring constructed to retain the fluid including biological material by surface tension and enable movement of the drop-carrying element therethrough.

3. The apparatus of claim 2, wherein the deposit device includes a pin having the drop carrying elements formed by a tip arranged to linearly move with respect to and through a volume defined by the ring.

4. The apparatus of claim 2, wherein the well forms a portion of a well plate.

5. The apparatus of claim 4, wherein the well plate is a 96 well plate.

6. The apparatus of claim 4 further including a mechanism for transporting the well plate with respect to the receiving surface.

7. The apparatus of claim 1, wherein the fluid-retaining structure includes a helical structure constructed to retain the fluid including biological material by surface tension and enable movement of the drop-carrying element therethrough.

8. The apparatus of claim 7, wherein the receiving surface includes a rigid, smooth substrate.

9. The apparatus of claim 8, wherein the rigid, smooth substrate is a glass slide.

10. The apparatus of claim 7, wherein the receiving surface includes a porous membrane.

11. The apparatus of claim 7, wherein the receiving surface includes a nitrocellulose.

12. The apparatus of claim 11, wherein the receiving surface includes a cellulose acetate, polyvinylidine fluoride (PVDF) or nylon.

13. The apparatus of claim 12, wherein the receiving surface includes a gel.

14. The apparatus of claim 1, wherein the fluid-retaining structure includes a U-shaped structure constructed to retain the fluid including biological material by surface tension and enable movement of the drop-carrying element therethrough.

15. The apparatus of claim 1, wherein the fluid-retaining structure includes a structure having a square, hexagonal, rectangular or oval cross-section and being constructed to retain the fluid including biological material by surface tension and enable movement of the drop-carrying element therethrough.

16. The apparatus of claim 1, Wherein the fluid-retaining structure is formed by a member that has opposed or adjacent surfaces that can hold a mass of fluid between them by surface tension.

17. An apparatus for depositing fluid dots on a receiving surface in an array, comprising:

a multiplicity of deposit devices mounted for motion together in response to a common actuator, each said deposit device including a drop-carrying element;

a multiplicity of fluid-retaining structures associated with said multiplicity of deposit devices, each said fluid-retaining structure being constructed to retain fluid including biological material by surface tension, each said fluid-retaining structure being constructed for immersion inside a well to receive the fluid including biological material; and a drive mechanism associated with said actuator constructed to move said multiplicity of deposit devices including said drop-carrying elements through said fluid-retaining structure to acquire a drop of the liquid onto each said drop-carrying element; said drive mechanism being constructed to displace said deposit devices including said drop-carrying elements toward and away from the receiving surface for deposition.

18. The apparatus of claim 17, wherein said multiplicity of fluid-retaining structures is generally movable together with said multiplicity of deposit devices over an array of deposit locations.

19. The apparatus of claim 18, wherein said multiplicity of deposit devices and said multiplicity of fluid-retaining structures includes four deposit devices and associated four ring-like structures forming said fluid-retaining structures.

20. The apparatus of claim 18, wherein said multiplicity of fluid-retaining structures has a spacing and distribution corresponding to a spacing and distribution of said wells in a well plate.

21. The apparatus of claim 20, wherein the well plate is a 96 well plate.

22. The apparatus of claim 20 further including a mechanism for transporting said well plate with respect to the receiving surface.

23. The apparatus of claim 22, wherein the receiving surface is a surface of a glass slide.

24. The apparatus of claim 22, wherein the receiving surface includes a porous membrane.

25. The apparatus of claim 22, wherein the receiving surface includes a nitrocellulose.

26. The apparatus of claim 20, wherein each said fluid-retaining structure includes a circular-shaped member for said retention of liquid by surface tension.

27. The apparatus of claim 20, wherein each said fluid-retaining structure includes a U-shaped member for said retention of liquid by surface tension.

28. The apparatus of claim 20, wherein said fluid-retaining structure includes a helical member for said retention of liquid by surface tension.

29. The apparatus of claim 20, wherein said fluid-retaining structure includes a closed shape member for said retention of liquid by surface tension.

30. The apparatus of claim 20, wherein said fluid-retaining structure includes a partially closed shape member for said retention of liquid by surface tension.

31. The apparatus of claim 20, wherein said fluid-retaining structure is made of a material proving appropriate surface tension for retaining said liquid including biological material.

32. The apparatus of claim 20, wherein said fluid-retaining structure provides surface energy greater than about 2500 mN/m for retaining said liquid including biological material.

33. The apparatus of claim 18, wherein the receiving surface includes a rigid, smooth substrate.

34. The apparatus of claim 18, wherein the rigid, smooth substrate is a surface of a glass slide.

35. The apparatus of claim 18, wherein the receiving surface includes a porous membrane.

36. The apparatus of claim 18, wherein the receiving surface includes a nitrocellulose.

* * * * *